US009526773B2

(12) United States Patent
Aagaard et al.

(10) Patent No.: US 9,526,773 B2
(45) Date of Patent: Dec. 27, 2016

(54) M. TUBERCULOSIS VACCINES

(71) Applicant: Statens Serum Institut, Copenhagen S (DK)

(72) Inventors: Claus Aagaard, Copenhagen S (DK); Ida Rosenkrands, Vaerlose (DK); Truc Thi Kim Thanh Hoang, Glostrup (DK); Peter Andersen, Bronshoj (DK)

(73) Assignee: Statens Serum Institut, Copenhagen S (DK)

( * ) Notice: Subject to any disclaimer, the term of this patent is extended or adjusted under 35 U.S.C. 154(b) by 0 days.

(21) Appl. No.: 14/437,998

(22) PCT Filed: Oct. 18, 2013

(86) PCT No.: PCT/DK2013/000070
§ 371 (c)(1),
(2) Date: Apr. 23, 2015

(87) PCT Pub. No.: WO2014/063704
PCT Pub. Date: May 1, 2014

(65) Prior Publication Data
US 2015/0290311 A1      Oct. 15, 2015

(30) Foreign Application Priority Data

Oct. 23, 2012  (DK) ................... 2012 00652
Oct. 23, 2012  (DK) ................... 2012 00653
Oct. 23, 2012  (DK) ................... 2012 00654
Aug. 23, 2013  (DK) ................... 2013 00477

(51) Int. Cl.
*A61K 39/04* (2006.01)
*C07K 14/35* (2006.01)
*A61K 39/00* (2006.01)

(52) U.S. Cl.
CPC ............. *A61K 39/04* (2013.01); *C07K 14/35* (2013.01); *A61K 2039/55555* (2013.01); *C07K 2319/00* (2013.01); *C07K 2319/40* (2013.01)

(58) Field of Classification Search
CPC ........ A61K 39/04; A61K 39/00; A61K 38/00; A61K 2039/51; A61K 2039/523; A61K 2039/53; A61K 2039/55555; A61K 39/39; A61K 2039/545; A61K 2039/55511; A61K 2039/55594; A61K 2300/00; A61K 47/186; A61K 47/26
See application file for complete search history.

(56) References Cited

FOREIGN PATENT DOCUMENTS

| EP | 1350839 A1 | 10/2003 |
| WO | WO 99/51748 A2 | 10/1999 |
| WO | WO 2010/121618 A1 | 10/2010 |
| WO | WO 2012/057904 A1 | 5/2012 |

OTHER PUBLICATIONS

Aagaard, C. et al., A multistage tuberculosis vaccine that confers efficient protection before and after exposure, Nature Medicine, Jan. 2011, 17(2): 189-195.
Dietrich, J. et al., Exchanging ESAT6 with TB10.4 in an Ag85B Fusion Molecule-Based Tuberculosis Subunit Vaccine: Efficient Protection and ESAT6-Based Sensitive Monitoring of Vaccine Efficacy1, The Journal of Immunology, Mar. 2005, 174(10): 6332-6339.
Aagaard, C. et al., TB Vaccines: Current Status and Future Perspectives, Immunology and Cell Biology, Apr. 2009, 87(4): 279-286.
Lu, Y. et al., Novel Recombinant BCG Coexpressing Ag85B, ESAT-6 and Rv2608 Elicits Significantly Enhanced Cellular Immune and Antibody Responses in C57BL/6 Mice, Basic Immunology, Sep. 2012, 76(3): 271-277.
Abdallah, M. et al., Type VII secretion—mycobacteria show the way, Perspectives, Nov. 2007, 5: 883-891.
Bahk, Y. et al., Antigens secreted from *Mycobacterium tuberculosis*: Identification by proteomics approach and test for diagnostic marker, Proteomics, Aug. 2004, 4: 3299-3307.
Bold, T.D. et al., Suboptimal Activation of Antigen-Specific CD4+ Effector Cells Enables Persistence of *M. tuberculosis* In Vivo, PLoS Pathogens, May 2011, 7(5): e1002063.
Brodin, P. et al., Dissection of ESAT-6 System 1 of *Mycobacterium tuberculosis* and Impact on Immunogenicity and Virulence, Infection and Immunity, Jan. 2006, 74(1): 88-98.
Champion, P.A.D. et al., C-Terminal Signal Sequence Promotes Virulence Factor Secretion in *Mycobacterium tuberculosis*, Science, Sep. 2006, 313: 1632-1636.
Chen, J.M. et al., EspD Is Critical for the Virulence-Mediating ESX-1 Secretion System in *Mycobacterium tuberculosis*, Journal of Bacteriology, Dec. 2011, 194(4): 884-893.
Cole, S.T. et al., Deciphering the biology of *Mycobacterium tuberculosis* from the complete genome sequence, Nature, Jun. 1998, 393(6685): 537-544.
Das, C. et al., Computational Analysis of the ESX-1 Region of *Mycobacterium tuberculosis*: Insights into the Mechanism of Type VII Secretion System, PLoS One, Nov. 2011, 6(11): e27980.
Egen, J.G. et al., Intravital Imaging Reveals Limited Antigen Presentation and T Cell Effector Function in Mycobacterial Granulomas, Immunity, May 2011, 34(5): 807-819.

(Continued)

*Primary Examiner* — Padma V Baskar
(74) *Attorney, Agent, or Firm* — Howson & Howson, LLP

(57) ABSTRACT

The present invention is directed to fusion proteins, antigen cocktails and immunological compositions such as vaccines against infections caused by virulent mycobacteria, e.g. by *Mycobacterium tuberculosis, Mycobacterium africanum, Mycobacterium bovis, Mycobacterium microti, Mycobacterium canettii, Mycobacterium pinnipedii* or *Mycobacterium mungi*. The fusion proteins or antigen cocktails are based on ESX secreted or associated proteins e.g. proteins secreted by the ESAT-6 secretion system 1 (ESX-1) which are among the most immunodominant *M. tuberculosis* (MTB) antigens.

17 Claims, 15 Drawing Sheets

(56) References Cited

OTHER PUBLICATIONS

Figure 1:
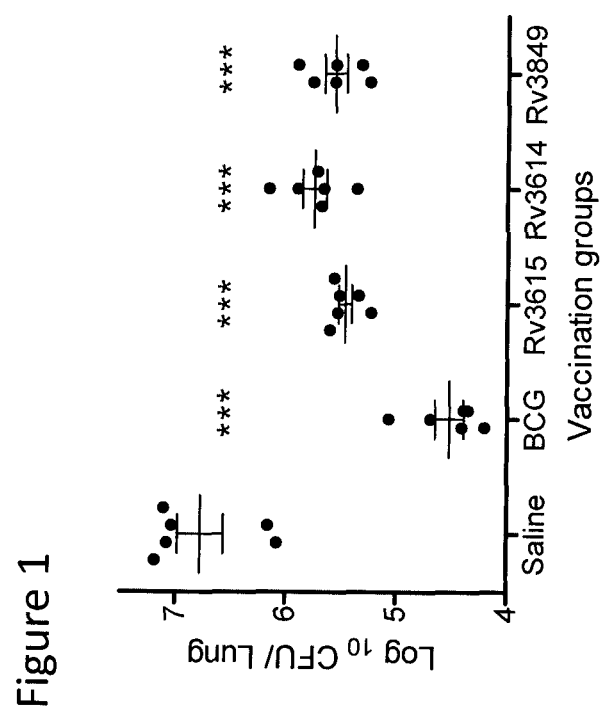

Fortune, S.M. et al., Mutually dependent secretion of proteins required for mycobacterial virulence, PNAS, Jun. 2005, 102(30): 10676-10681.
Gao, L.Y. et al., A mycobacterial virulence gene cluster extending RD1 is required for cytolysis, bacterial spreading and ESAT-6 secretion, Molecular Microbiology, Sep. 2004, 53(6): 1677-1693.
Gordon, S.V. et al., Identification of variable regions in the genomes of tubercle bacilli using bacterial artificial chromosome arrays, Molecular Microbiology, May 1999, 32(3): 643-655.
MacGurn, J.A. et al., A non-RD1 gene cluster is required for Snm secretion in *Mycobacterium tuberculosis*, Molecular Microbiology, Sep. 2005, 57(6):1653-1663.
MacGurn, J.A. et al., A Genetic Screen for *Mycobacterium tuberculosis* Mutants Defective for Phagosome Maturation Arrest Identifies Components of the ESX-1 Secretion System, Infection and Immunity, Jun. 2007, 75(6): 2668-2678.
Ohol, Y.M. et al., *Mycobacterium tuberculosis* MycP1 Protease Plays a Dual Role in Regulation of ESX-1 Secretion and Virulence, Cell Host and Microbe, Mar. 2010, 7(3): 210-220.
Pym, A.S. et al., Recombinant BCG Exporting ESAT-6 Confers Enhanced Protection Against Tuberculosis, Apr. 2003, Nature Medicine, 9(5): 533-539.
Raghavan, S. et al., Secreted transcription factor controls *Mycobacterium tuberculosis* virulence, Nature, Aug. 2008, 454(7205): 717-721.
Stanley, S.A. et al., Acute infection and macrophage subversion by *Mycobacterium tuberculosis* require a specialized secretion system, PNAS, Oct. 2003, 100(22): 13001-13006.
International Search Report issued Apr. 23, 2014 in PCT/DK2013/000070 (international stage of present application).
Written Opinion issued Apr. 23, 2014 in PCT/DK2013/000070 (international stage of present application).

SEQUENCE LISTING

<160> NUMBER OF SEQ ID NOS: 26

<210> SEQ ID NO 1
<211> LENGTH: 95
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 2
<211> LENGTH: 184
<212> TYPE: PRT
<213> ORGANISM: Mycobacterium tuberculosis

<400> SEQUENCE: 2

Val Asp Leu Pro Gly Asn Asp Phe Asp Ser Asn Asp Phe Asp Ala Val
1               5                   10                  15

Asp Leu Trp Gly Ala Asp Gly Ala Glu Gly Trp Thr Ala Asp Pro Ile
            20                  25                  30

Ile Gly Val Gly Ser Ala Ala Thr Pro Asp Thr Gly Pro Asp Leu Asp
        35                  40                  45

Asn Ala His Gly Gln Ala Glu Thr Asp Thr Glu Gln Glu Ile Ala Leu
    50                  55                  60

Phe Thr Val Thr Asn Pro Pro Arg Thr Val Ser Val Ser Thr Leu Met
65                  70                  75                  80

Asp Gly Arg Ile Asp His Val Glu Leu Ser Ala Arg Val Ala Trp Met
                85                  90                  95

Ser Glu Ser Gln Leu Ala Ser Glu Ile Leu Val Ile Ala Asp Leu Ala
            100                 105                 110

Arg Gln Lys Ala Gln Ser Ala Gln Tyr Ala Phe Ile Leu Asp Arg Met
        115                 120                 125

Ser Gln Gln Val Asp Ala Asp Glu His Arg Val Ala Leu Leu Arg Lys
    130                 135                 140

-continued

```
Thr Val Gly Glu Thr Trp Gly Leu Pro Ser Pro Glu Glu Ala Ala Ala
145                 150                 155                 160

Ala Glu Ala Glu Val Phe Ala Thr Arg Tyr Ser Asp Asp Cys Pro Ala
                165                 170                 175

Pro Asp Asp Glu Ser Asp Pro Trp
            180

<210> SEQ ID NO 3
<211> LENGTH: 103
<212> TYPE: PRT
<213> ORGANISM: Mycobacterium tuberculosis

<400> SEQUENCE: 3

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
                20                  25                  30

Ala Ala Gly Leu Gly Glu Ser Val Ala Ile Thr His Gly Pro Tyr Cys
            35                  40                  45

Ser Gln Phe Asn Asp Thr Leu Asn Val Tyr Leu Thr Ala His Asn Ala
        50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95

Ala Ile Asp Gly Leu Phe Thr
            100

<210> SEQ ID NO 4
<211> LENGTH: 103
<212> TYPE: PRT
<213> ORGANISM: Mycobacterium tuberculosis

<400> SEQUENCE: 4

Met Thr Gly Phe Leu Gly Val Val Pro Ser Phe Leu Lys Val Leu Ala
1               5                   10                  15

Gly Met His Asn Glu Ile Val Gly Asp Ile Lys Arg Ala Thr Asp Thr
                20                  25                  30

Val Ala Gly Ile Ser Gly Arg Val Gln Leu Thr His Gly Ser Phe Thr
            35                  40                  45

Ser Lys Phe Asn Asp Thr Leu Gln Glu Phe Glu Thr Thr Arg Ser Ser
        50                  55                  60

Thr Gly Thr Gly Leu Gln Gly Val Thr Gly Leu Ala Asn Asn Leu
65                  70                  75                  80

Leu Ala Ala Ala Gly Ala Tyr Leu Lys Ala Asp Asp Gly Leu Ala Gly
                85                  90                  95

Val Ile Asp Lys Ile Phe Gly
            100

<210> SEQ ID NO 5
<211> LENGTH: 132
<212> TYPE: PRT
<213> ORGANISM: Mycobacterium tuberculosis

<400> SEQUENCE: 5

Met Ser Thr Thr Phe Ala Ala Arg Leu Asn Arg Leu Phe Asp Thr Val
1               5                   10                  15

Tyr Pro Pro Gly Arg Gly Pro His Thr Ser Ala Glu Val Ile Ala Ala
```

```
        20                      25                      30
Leu Lys Ala Glu Gly Ile Thr Met Ser Ala Pro Tyr Leu Ser Gln Leu
            35                      40                      45

Arg Ser Gly Asn Arg Thr Asn Pro Ser Gly Ala Thr Met Ala Ala Leu
        50                      55                      60

Ala Asn Phe Phe Arg Ile Lys Ala Ala Tyr Phe Thr Asp Asp Glu Tyr
65                      70                      75                      80

Tyr Glu Lys Leu Asp Lys Glu Leu Gln Trp Leu Cys Thr Met Arg Asp
                    85                      90                      95

Asp Gly Val Arg Arg Ile Ala Gln Arg Ala His Gly Leu Pro Ser Ala
                100                     105                     110

Ala Gln Gln Lys Val Leu Asp Arg Ile Asp Glu Leu Arg Arg Ala Glu
            115                     120                     125

Gly Ile Asp Ala
        130

<210> SEQ ID NO 6
<211> LENGTH: 99
<212> TYPE: PRT
<213> ORGANISM: Mycobacterium tuberculosis

<400> SEQUENCE: 6

Met Glu Lys Met Ser His Asp Pro Ile Ala Asp Ile Gly Thr Gln
1               5                   10                  15

Val Ser Asp Asn Ala Leu His Gly Val Thr Ala Gly Ser Thr Ala Leu
                    20                      25                  30

Thr Ser Val Thr Gly Leu Val Pro Ala Gly Ala Asp Glu Val Ser Ala
            35                      40                      45

Gln Ala Ala Thr Ala Phe Thr Ser Glu Gly Ile Gln Leu Leu Ala Ser
        50                      55                      60

Asn Ala Ser Ala Gln Asp Gln Leu His Arg Ala Gly Glu Ala Val Gln
65                      70                      75                      80

Asp Val Ala Arg Thr Tyr Ser Gln Ile Asp Asp Gly Ala Ala Gly Val
                    85                      90                      95

Phe Ala Glu

<210> SEQ ID NO 7
<211> LENGTH: 392
<212> TYPE: PRT
<213> ORGANISM: Mycobacterium tuberculosis

<400> SEQUENCE: 7

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
                    20                      25                      30

Tyr Ser Ser Leu Glu Tyr Phe Glu Lys Ala Leu Glu Glu Leu Ala Ala
            35                      40                      45

Ala Phe Pro Gly Asp Gly Trp Leu Gly Ser Ala Ala Asp Lys Tyr Ala
        50                      55                      60

Gly Lys Asn Arg Asn His Val Asn Phe Phe Gln Glu Leu Ala Asp Leu
65                      70                      75                      80

Asp Arg Gln Leu Ile Ser Leu Ile His Asp Gln Ala Asn Ala Val Gln
                    85                      90                      95

Thr Thr Arg Asp Ile Leu Glu Gly Ala Lys Lys Gly Leu Glu Phe Val
                100                     105                     110
```

Arg Pro Val Ala Val Asp Leu Thr Tyr Ile Pro Val Gly His Ala
            115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
            180                 185                 190

Leu Gly Glu Val Trp Glu Phe Ile Thr Asn Ala Leu Asn Gly Leu Lys
        195                 200                 205

Glu Leu Trp Asp Lys Leu Thr Gly Trp Val Thr Gly Leu Phe Ser Arg
    210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
            260                 265                 270

Ser Ala Ser Leu Pro Ala Leu Ala Gly Ile Gly Gly Gly Ser Gly Phe
        275                 280                 285

Gly Gly Leu Pro Ser Leu Ala Gln Val His Ala Ala Ser Thr Arg Gln
    290                 295                 300

Ala Leu Arg Pro Arg Ala Asp Gly Pro Val Gly Ala Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Gly Met His Pro Ser Ser Gly Ala Ser
            340                 345                 350

Lys Gly Thr Thr Thr Lys Lys Tyr Ser Glu Gly Ala Ala Ala Gly Thr
        355                 360                 365

Glu Asp Ala Glu Arg Ala Pro Val Glu Ala Asp Ala Gly Gly Gly Gln
    370                 375                 380

Lys Val Leu Val Arg Asn Val Val
385                 390

<210> SEQ ID NO 8
<211> LENGTH: 460
<212> TYPE: PRT
<213> ORGANISM: Mycobacterium tuberculosis

<400> SEQUENCE: 8

Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Pro Thr Asp Val
            20                  25                  30

Pro Ile Thr Pro Cys Glu Leu Thr Ala Ala Lys Asn Ala Ala Gln Gln
        35                  40                  45

Leu Val Leu Ser Ala Asp Asn Met Arg Glu Tyr Leu Ala Ala Gly Ala
    50                  55                  60

Lys Glu Arg Gln Arg Leu Ala Thr Ser Leu Arg Asn Ala Ala Lys Ala
65                  70                  75                  80

Tyr Gly Glu Val Asp Glu Glu Ala Ala Thr Ala Leu Asp Asn Asp Gly

```
                     85                  90                  95
Glu Gly Thr Val Gln Ala Glu Ser Ala Gly Ala Val Gly Gly Asp Ser
                    100                 105                 110
Ser Ala Glu Leu Thr Asp Thr Pro Arg Val Ala Thr Ala Gly Glu Pro
                115                 120                 125
Asn Phe Met Asp Leu Lys Glu Ala Ala Arg Lys Leu Glu Thr Gly Asp
            130                 135                 140
Gln Gly Ala Ser Leu Ala His Phe Ala Asp Gly Trp Asn Thr Phe Asn
145                 150                 155                 160
Leu Thr Leu Gln Gly Asp Val Lys Arg Phe Arg Gly Phe Asp Asn Trp
                165                 170                 175
Glu Gly Asp Ala Ala Thr Ala Cys Glu Ala Ser Leu Asp Gln Gln Arg
            180                 185                 190
Gln Trp Ile Leu His Met Ala Lys Leu Ser Ala Ala Met Ala Lys Gln
            195                 200                 205
Ala Gln Tyr Val Ala Gln Leu His Val Trp Ala Arg Arg Glu His Pro
        210                 215                 220
Thr Tyr Glu Asp Ile Val Gly Leu Glu Arg Leu Tyr Ala Glu Asn Pro
225                 230                 235                 240
Ser Ala Arg Asp Gln Ile Leu Pro Val Tyr Ala Glu Tyr Gln Gln Arg
                245                 250                 255
Ser Glu Lys Val Leu Thr Glu Tyr Asn Asn Lys Ala Ala Leu Glu Pro
            260                 265                 270
Val Asn Pro Pro Lys Pro Pro Ala Ile Lys Ile Asp Pro Pro Pro
        275                 280                 285
Pro Pro Gln Glu Gln Gly Leu Ile Pro Gly Phe Leu Met Pro Pro Ser
    290                 295                 300
Asp Gly Ser Gly Val Thr Pro Gly Thr Gly Met Pro Ala Ala Pro Met
305                 310                 315                 320
Val Pro Pro Thr Gly Ser Pro Gly Gly Gly Leu Pro Ala Asp Thr Ala
                325                 330                 335
Ala Gln Leu Thr Ser Ala Gly Arg Glu Ala Ala Ala Leu Ser Gly Asp
            340                 345                 350
Val Ala Val Lys Ala Ala Ser Leu Gly Gly Gly Gly Gly Gly Gly Val
        355                 360                 365
Pro Ser Ala Pro Leu Gly Ser Ala Ile Gly Gly Ala Glu Ser Val Arg
    370                 375                 380
Pro Ala Gly Ala Gly Asp Ile Ala Gly Leu Gly Gln Gly Arg Ala Gly
385                 390                 395                 400
Gly Gly Ala Ala Leu Gly Gly Gly Met Gly Met Pro Met Gly Ala
                405                 410                 415
Ala His Gln Gly Gln Gly Gly Ala Lys Ser Lys Gly Ser Gln Gln Glu
            420                 425                 430
Asp Glu Ala Leu Tyr Thr Glu Asp Arg Ala Trp Thr Glu Ala Val Ile
        435                 440                 445
Gly Asn Arg Arg Arg Gln Asp Ser Lys Glu Ser Lys
    450                 455                 460

<210> SEQ ID NO 9
<211> LENGTH: 107
<212> TYPE: PRT
<213> ORGANISM: Mycobacterium tuberculosis

<400> SEQUENCE: 9
```

-continued

Val Ala Asp Thr Ile Gln Val Thr Pro Gln Met Leu Arg Ser Thr Ala
1               5                   10                  15

Asn Asp Ile Gln Ala Asn Met Glu Gln Ala Met Gly Ile Ala Lys Gly
            20                  25                  30

Tyr Leu Ala Asn Gln Glu Asn Val Met Asn Pro Ala Thr Trp Ser Gly
        35                  40                  45

Thr Gly Val Val Ala Ser His Met Thr Ala Thr Glu Ile Thr Asn Glu
    50                  55                  60

Leu Asn Lys Val Leu Thr Gly Gly Thr Arg Leu Ala Glu Gly Leu Val
65                  70                  75                  80

Gln Ala Ala Ala Leu Met Glu Gly His Glu Ala Asp Ser Gln Thr Ala
                85                  90                  95

Phe Gln Ala Leu Phe Gly Ala Ser His Gly Ser
            100                 105

<210> SEQ ID NO 10
<211> LENGTH: 95
<212> TYPE: PRT
<213> ORGANISM: Mycobacterium tuberculosis

<400> SEQUENCE: 10

Met Ser Asp Gln Ile Thr Tyr Asn Pro Gly Ala Val Ser Asp Phe Ala
1               5                   10                  15

Ser Asp Val Gly Ser Arg Ala Gly Gln Leu His Met Ile Tyr Glu Asp
            20                  25                  30

Thr Ala Ser Lys Thr Asn Ala Leu Gln Glu Phe Phe Ala Gly His Gly
        35                  40                  45

Ala Gln Gly Phe Phe Asp Ala Gln Ala Gln Met Leu Ser Gly Leu Gln
    50                  55                  60

Gly Leu Ile Glu Thr Val Gly Gln His Gly Thr Thr Thr Gly His Val
65                  70                  75                  80

Leu Asp Asn Ala Ile Gly Thr Asp Gln Ala Ile Ala Gly Leu Phe
                85                  90                  95

<210> SEQ ID NO 11
<211> LENGTH: 97
<212> TYPE: PRT
<213> ORGANISM: Mycobacterium tuberculosis

<400> SEQUENCE: 11

Met Ser Leu Leu Asp Ala His Ile Pro Gln Leu Val Ala Ser Gln Ser
1               5                   10                  15

Ala Phe Ala Ala Lys Ala Gly Leu Met Arg His Thr Ile Gly Gln Ala
            20                  25                  30

Glu Gln Ala Ala Met Ser Ala Gln Ala Phe His Gln Gly Glu Ser Ser
        35                  40                  45

Ala Ala Phe Gln Ala Ala His Ala Arg Phe Val Ala Ala Ala Ala Lys
    50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ser Thr Tyr Thr Gly
                85                  90                  95

Phe

<210> SEQ ID NO 12
<211> LENGTH: 96
<212> TYPE: PRT

```
<213> ORGANISM: Mycobacterium tuberculosis

<400> SEQUENCE: 12

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95

<210> SEQ ID NO 13
<211> LENGTH: 468
<212> TYPE: PRT
<213> ORGANISM: Mycobacterium tuberculosis

<400> SEQUENCE: 13

Val Phe Ser Ile Thr Thr Leu Arg Asp Trp Thr Pro Asp Pro Gly Ser
1               5                   10                  15

Ile Ile Cys Trp His Ala Ser Pro Thr Ala Lys Ala Lys Ala Arg Gln
            20                  25                  30

Ala Pro Ile Ser Glu Val Pro Pro Ser Tyr Gln Gln Ala Gln His Leu
        35                  40                  45

Arg Arg Tyr Arg Asp His Val Ala Arg Gly Leu Asp Met Ser Arg Leu
    50                  55                  60

Met Ile Phe Thr Trp Asp Leu Pro Gly Arg Cys Asn Ile Arg Ala Met
65                  70                  75                  80

Asn Tyr Ala Ile Asn Ala His Leu Arg Arg His Asp Thr Tyr His Ser
                85                  90                  95

Trp Phe Glu Phe Asp Asn Ala Glu His Ile Val Arg His Thr Ile Ala
            100                 105                 110

Asp Pro Ala Asp Ile Glu Val Val Gln Ala Glu His Gln Asn Met Thr
        115                 120                 125

Ser Ala Glu Leu Arg His His Ile Ala Thr Pro Gln Pro Leu Gln Trp
    130                 135                 140

Asp Cys Phe Leu Phe Gly Ile Ile Gln Ser Asp Asp His Phe Thr Phe
145                 150                 155                 160

Tyr Ala Ser Ile Ala His Leu Cys Val Asp Pro Met Ile Val Gly Val
                165                 170                 175

Leu Phe Ile Glu Ile His Met Met Tyr Ser Ala Leu Val Gly Gly Asp
            180                 185                 190

Pro Pro Ile Glu Leu Pro Pro Ala Gly Arg Tyr Asp Asp His Cys Val
        195                 200                 205

Arg Gln Tyr Ala Asp Thr Ala Ala Leu Thr Leu Asp Ser Ala Arg Val
    210                 215                 220

Arg Arg Trp Val Glu Phe Ala Ala Asn Asn Asp Gly Thr Leu Pro His
225                 230                 235                 240

Phe Pro Leu Pro Leu Gly Asp Leu Ser Val Pro His Thr Gly Lys Leu
                245                 250                 255

Leu Thr Glu Thr Leu Met Asp Glu Gln Gln Gly Glu Arg Phe Glu Ala
```

```
                260                 265                 270
Ala Cys Val Ala Ala Gly Ala Arg Phe Ser Gly Gly Val Phe Ala Cys
            275                 280                 285

Ala Ala Leu Ala Glu Arg Glu Leu Thr Asn Cys Glu Thr Phe Asp Val
        290                 295                 300

Val Thr Thr Thr Asp Thr Arg Arg Thr Pro Thr Glu Leu Arg Thr Thr
305                 310                 315                 320

Gly Trp Phe Thr Gly Leu Val Pro Ile Thr Val Pro Val Ala Ser Gly
                325                 330                 335

Leu Phe Asp Ser Ala Ala Arg Val Ala Gln Ile Ser Phe Asp Ser Gly
                340                 345                 350

Lys Asp Leu Ala Thr Val Pro Phe Asp Arg Val Leu Glu Leu Ala Arg
            355                 360                 365

Pro Glu Thr Gly Leu Arg Pro Arg Pro Gly Asn Phe Val Met Ser
        370                 375                 380

Phe Leu Asp Ala Ser Ile Ala Pro Leu Ser Thr Val Ala Asn Ser Asp
385                 390                 395                 400

Leu Asn Phe Arg Ile Tyr Asp Glu Gly Arg Val Ser His Gln Val Ser
                405                 410                 415

Met Trp Val Asn Arg Tyr Gln His Gln Thr Thr Val Thr Val Leu Phe
                420                 425                 430

Pro Asp Asn Pro Ile Ala Ser Glu Ser Val Ala Asn Tyr Ile Ala Ala
            435                 440                 445

Met Lys Ser Ile Tyr Ile Arg Thr Ala Asp Gly Thr Leu Ala Thr Leu
        450                 455                 460

Lys Pro Gly Thr
465

<210> SEQ ID NO 14
<211> LENGTH: 111
<212> TYPE: PRT
<213> ORGANISM: Mycobacterium tuberculosis

<400> SEQUENCE: 14

Met Met Gln Phe Tyr Asp Asp Gly Val Val Gln Leu Asp Arg Ala Ala
1               5                   10                  15

Leu Thr Leu Arg Arg Tyr His Phe Pro Ser Gly Thr Ala Lys Val Ile
            20                  25                  30

Pro Leu Asp Gln Ile Arg Gly Tyr Gln Ala Glu Ser Leu Gly Phe Leu
        35                  40                  45

Met Ala Arg Phe Asn Ile Trp Gly Arg Pro Asp Leu Arg Arg Trp Leu
    50                  55                  60

Pro Leu Asp Val Tyr Arg Pro Leu Lys Ser Thr Leu Val Thr Leu Asp
65                  70                  75                  80

Val Pro Gly Met Arg Pro Lys Pro Ala Cys Thr Pro Thr Arg Pro Lys
                85                  90                  95

Glu Phe Ile Ala Leu Leu Asp Glu Leu Leu Ala Leu His Arg Thr
            100                 105                 110

<210> SEQ ID NO 15
<211> LENGTH: 285
<212> TYPE: PRT
<213> ORGANISM: Mycobacterium tuberculosis

<400> SEQUENCE: 15

Phe Ser Arg Pro Gly Leu Pro Val Glu Tyr Leu Gln Val Pro Ser Pro
```

```
              1               5              10              15
            Ser Met Gly Arg Asp Ile Lys Val Gln Phe Gln Ser Gly Gly Asn Asn
                             20              25              30

Ser Pro Ala Val Tyr Leu Leu Asp Gly Leu Arg Ala Gln Asp Asp Tyr
                             35              40              45

Asn Gly Trp Asp Ile Asn Thr Pro Ala Phe Glu Trp Tyr Tyr Gln Ser
                             50              55              60

Gly Leu Ser Ile Val Met Pro Val Gly Gly Gln Ser Ser Phe Tyr Ser
             65              70              75              80

Asp Trp Tyr Ser Pro Ala Cys Gly Lys Ala Gly Cys Gln Thr Tyr Lys
                             85              90              95

Trp Glu Thr Phe Leu Thr Ser Glu Leu Pro Gln Trp Leu Ser Ala Asn
                            100             105             110

Arg Ala Val Lys Pro Thr Gly Ser Ala Ala Ile Gly Leu Ser Met Ala
                            115             120             125

Gly Ser Ser Ala Met Ile Leu Ala Ala Tyr His Pro Gln Gln Phe Ile
                            130             135             140

Tyr Ala Gly Ser Leu Ser Ala Leu Leu Asp Pro Ser Gln Gly Met Gly
            145             150             155             160

Pro Ser Leu Ile Gly Leu Ala Met Gly Asp Ala Gly Tyr Lys Ala
                            165             170             175

Ala Asp Met Trp Gly Pro Ser Ser Asp Pro Ala Trp Glu Arg Asn Asp
                            180             185             190

Pro Thr Gln Gln Ile Pro Lys Leu Val Ala Asn Asn Thr Arg Leu Trp
                            195             200             205

Val Tyr Cys Gly Asn Gly Thr Pro Asn Glu Leu Gly Gly Ala Asn Ile
                            210             215             220

Pro Ala Glu Phe Leu Glu Asn Phe Val Arg Ser Ser Asn Leu Lys Phe
            225             230             235             240

Gln Asp Ala Tyr Asn Ala Ala Gly Gly His Asn Ala Val Phe Asn Phe
                            245             250             255

Pro Pro Asn Gly Thr His Ser Trp Glu Tyr Trp Gly Ala Gln Leu Asn
                            260             265             270

Ala Met Lys Gly Asp Leu Gln Ser Ser Leu Gly Ala Gly
                            275             280             285

<210> SEQ ID NO 16
<211> LENGTH: 163
<212> TYPE: PRT
<213> ORGANISM: Mycobacterium tuberculosis

<400> SEQUENCE: 16

Val Thr Val Thr Asp Asp Tyr Leu Ala Asn Asn Val Asp Tyr Ala Ser
             1               5              10              15

Gly Phe Lys Gly Pro Leu Pro Met Pro Pro Ser Lys His Ile Ala Ile
                             20              25              30

Val Ala Cys Met Asp Ala Arg Leu Asp Val Tyr Arg Met Leu Gly Ile
                             35              40              45

Lys Glu Gly Glu Ala His Val Ile Arg Asn Ala Gly Cys Val Val Thr
             50              55              60

Asp Asp Val Ile Arg Ser Leu Ala Ile Ser Gln Arg Leu Leu Gly Thr
             65              70              75              80

Arg Glu Ile Ile Leu Leu His His Thr Asp Cys Gly Met Leu Thr Phe
                             85              90              95
```

```
Thr Asp Asp Asp Phe Lys Arg Ala Ile Gln Asp Glu Thr Gly Ile Arg
            100                 105                 110

Pro Thr Trp Ser Pro Glu Ser Tyr Pro Asp Ala Val Glu Asp Val Arg
        115                 120                 125

Gln Ser Leu Arg Arg Ile Glu Val Asn Pro Phe Val Thr Lys His Thr
    130                 135                 140

Ser Leu Arg Gly Phe Val Phe Asp Val Ala Thr Gly Lys Leu Asn Glu
145                 150                 155                 160

Val Thr Pro

<210> SEQ ID NO 17
<211> LENGTH: 379
<212> TYPE: PRT
<213> ORGANISM: Mycobacterium tuberculosis

<400> SEQUENCE: 17

Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Asn Asn
            20                  25                  30

Ser Pro Ala Val Tyr Leu Leu Asp Gly Leu Arg Ala Gln Asp Asp Tyr
        35                  40                  45

Asn Gly Trp Asp Ile Asn Thr Pro Ala Phe Glu Trp Tyr Tyr Gln Ser
    50                  55                  60

Gly Leu Ser Ile Val Met Pro Val Gly Gly Gln Ser Ser Phe Tyr Ser
65                  70                  75                  80

Asp Trp Tyr Ser Pro Ala Cys Gly Lys Ala Gly Cys Gln Thr Tyr Lys
                85                  90                  95

Trp Glu Thr Phe Leu Thr Ser Glu Leu Pro Gln Trp Leu Ser Ala Asn
            100                 105                 110

Arg Ala Val Lys Pro Thr Gly Ser Ala Ala Ile Gly Leu Ser Met Ala
        115                 120                 125

Gly Ser Ser Ala Met Ile Leu Ala Ala Tyr His Pro Gln Gln Phe Ile
    130                 135                 140

Tyr Ala Gly Ser Leu Ser Ala Leu Leu Asp Pro Ser Gln Gly Met Gly
145                 150                 155                 160

Pro Ser Leu Ile Gly Leu Ala Met Gly Asp Ala Gly Gly Tyr Lys Ala
                165                 170                 175

Ala Asp Met Trp Gly Pro Ser Ser Asp Pro Ala Trp Glu Arg Asn Asp
            180                 185                 190

Pro Thr Gln Gln Ile Pro Lys Leu Val Ala Asn Asn Thr Arg Leu Trp
        195                 200                 205

Val Tyr Cys Gly Asn Gly Thr Pro Asn Glu Leu Gly Gly Ala Asn Ile
    210                 215                 220

Pro Ala Glu Phe Leu Glu Asn Phe Val Arg Ser Ser Asn Leu Lys Phe
225                 230                 235                 240

Gln Asp Ala Tyr Asn Ala Ala Gly Gly His Asn Ala Val Phe Asn Phe
                245                 250                 255

Pro Pro Asn Gly Thr His Ser Trp Glu Tyr Trp Gly Ala Gln Leu Asn
            260                 265                 270

Ala Met Lys Gly Asp Leu Gln Ser Ser Leu Gly Ala Gly Thr Glu Gln
        275                 280                 285

Gln Trp Asn Phe Ala Gly Ile Glu Ala Ala Ala Ser Ala Ile Gln Gly
    290                 295                 300
```

```
Asn Val Thr Ser Ile His Ser Leu Leu Asp Glu Gly Lys Gln Ser Leu
305                 310                 315                 320

Thr Lys Leu Ala Ala Ala Trp Gly Gly Ser Gly Ser Glu Ala Tyr Gln
            325                 330                 335

Gly Val Gln Gln Lys Trp Asp Ala Thr Ala Thr Glu Leu Asn Asn Ala
        340                 345                 350

Leu Gln Asn Leu Ala Arg Thr Ile Ser Glu Ala Gly Gln Ala Met Ala
    355                 360                 365

Ser Thr Glu Gly Asn Val Thr Gly Met Phe Ala
370                 375
```

<210> SEQ ID NO 18
<211> LENGTH: 715
<212> TYPE: PRT
<213> ORGANISM: Mycobacterium tuberculosis

<400> SEQUENCE: 18

```
Thr Glu Gln Gln Trp Asn Phe Ala Gly Ile Glu Ala Ala Ala Ser Ala
1               5                   10                  15

Ile Gln Gly Asn Val Thr Ser Ile His Ser Leu Leu Asp Glu Gly Lys
            20                  25                  30

Gln Ser Leu Thr Lys Leu Ala Ala Ala Trp Gly Gly Ser Gly Ser Glu
        35                  40                  45

Ala Tyr Gln Gly Val Gln Gln Lys Trp Asp Ala Thr Ala Thr Glu Leu
    50                  55                  60

Asn Asn Ala Leu Gln Asn Leu Ala Arg Thr Ile Ser Glu Ala Gly Gln
65                  70                  75                  80

Ala Met Ala Ser Thr Glu Gly Asn Val Thr Gly Met Phe Ala Met Asp
                85                  90                  95

Leu Pro Gly Asn Asp Phe Asp Ser Asn Asp Phe Asp Ala Val Asp Leu
            100                 105                 110

Trp Gly Ala Asp Gly Ala Glu Gly Trp Thr Ala Asp Pro Ile Ile Gly
        115                 120                 125

Val Gly Ser Ala Ala Thr Pro Asp Thr Gly Pro Asp Leu Asp Asn Ala
130                 135                 140

His Gly Gln Ala Glu Thr Asp Thr Glu Gln Glu Ile Ala Leu Phe Thr
145                 150                 155                 160

Val Thr Asn Pro Pro Arg Thr Val Ser Val Ser Thr Leu Met Asp Gly
                165                 170                 175

Arg Ile Asp His Val Glu Leu Ser Ala Arg Val Ala Trp Met Ser Glu
            180                 185                 190

Ser Gln Leu Ala Ser Glu Ile Leu Val Ile Ala Asp Leu Ala Arg Gln
        195                 200                 205

Lys Ala Gln Ser Ala Gln Tyr Ala Phe Ile Leu Asp Arg Met Ser Gln
    210                 215                 220

Gln Val Asp Ala Asp Glu His Arg Val Ala Leu Leu Arg Lys Thr Val
225                 230                 235                 240

Gly Glu Thr Trp Gly Leu Pro Ser Pro Glu Ala Ala Ala Glu
                245                 250                 255

Ala Glu Val Phe Ala Thr Arg Tyr Ser Asp Asp Ser Pro Ala Pro Asp
            260                 265                 270

Asp Glu Ser Asp Pro Trp Met Thr Glu Asn Leu Thr Val Gln Pro Glu
        275                 280                 285

Arg Leu Gly Val Leu Ala Ser His His Asp Asn Ala Ala Val Asp Ala
    290                 295                 300
```

```
Ser Ser Gly Val Glu Ala Ala Gly Leu Gly Glu Ser Val Ala Ile
305                 310                 315                 320

Thr His Gly Pro Tyr Ser Ser Gln Phe Asn Asp Thr Leu Asn Val Tyr
                    325                 330                 335

Leu Thr Ala His Asn Ala Leu Gly Ser Ser Leu His Thr Ala Gly Val
                340                 345                 350

Asp Leu Ala Lys Ser Leu Arg Ile Ala Ala Lys Ile Tyr Ser Glu Ala
                355                 360                 365

Asp Glu Ala Trp Arg Lys Ala Ile Asp Gly Leu Phe Thr Met Thr Gly
                370                 375                 380

Phe Leu Gly Val Val Pro Ser Phe Leu Lys Val Leu Ala Gly Met His
385                 390                 395                 400

Asn Glu Ile Val Gly Asp Ile Lys Arg Ala Thr Asp Thr Val Ala Gly
                405                 410                 415

Ile Ser Gly Arg Val Gln Leu Thr His Gly Ser Phe Thr Ser Lys Phe
                420                 425                 430

Asn Asp Thr Leu Gln Glu Phe Glu Thr Thr Arg Ser Ser Thr Gly Thr
                435                 440                 445

Gly Leu Gln Gly Val Thr Ser Gly Leu Ala Asn Asn Leu Leu Ala Ala
450                 455                 460

Ala Gly Ala Tyr Leu Lys Ala Asp Asp Gly Leu Ala Gly Val Ile Asp
465                 470                 475                 480

Lys Ile Phe Gly Met Ser Thr Thr Phe Ala Ala Arg Leu Asn Arg Leu
                485                 490                 495

Phe Asp Thr Val Tyr Pro Pro Gly Arg Gly Pro His Thr Ser Ala Glu
                500                 505                 510

Val Ile Ala Ala Leu Lys Ala Glu Gly Ile Thr Met Ser Ala Pro Tyr
515                 520                 525

Leu Ser Gln Leu Arg Ser Gly Asn Arg Thr Asn Pro Ser Gly Ala Thr
                530                 535                 540

Met Ala Ala Leu Ala Asn Phe Phe Arg Ile Lys Ala Ala Tyr Phe Thr
545                 550                 555                 560

Asp Asp Glu Tyr Tyr Glu Lys Leu Asp Lys Glu Leu Gln Trp Leu Ser
                565                 570                 575

Thr Met Arg Asp Asp Gly Val Arg Arg Ile Ala Gln Arg Ala His Gly
                580                 585                 590

Leu Pro Ser Ala Ala Gln Gln Lys Val Leu Asp Arg Ile Asp Glu Leu
                595                 600                 605

Arg Arg Ala Glu Gly Ile Asp Ala Met Glu Lys Met Ser His Asp Pro
610                 615                 620

Ile Ala Ala Asp Ile Gly Thr Gln Val Ser Asp Asn Ala Leu His Gly
625                 630                 635                 640

Val Thr Ala Gly Ser Thr Ala Leu Thr Ser Val Thr Gly Leu Val Pro
                645                 650                 655

Ala Gly Ala Asp Glu Val Ser Ala Gln Ala Ala Thr Ala Phe Thr Ser
                660                 665                 670

Glu Gly Ile Gln Leu Leu Ala Ser Asn Ala Ser Ala Gln Asp Gln Leu
                675                 680                 685

His Arg Ala Gly Glu Ala Val Gln Asp Val Ala Arg Thr Tyr Ser Gln
                690                 695                 700

Ile Asp Asp Gly Ala Ala Gly Val Phe Ala Glu
705                 710                 715
```

<210> SEQ ID NO 19
<211> LENGTH: 621
<212> TYPE: PRT
<213> ORGANISM: Mycobacterium tuberculosis

<400> SEQUENCE: 19

```
Met Asp Leu Pro Gly Asn Asp Phe Asp Ser Asn Asp Phe Asp Ala Val
1               5                   10                  15

Asp Leu Trp Gly Ala Asp Gly Ala Glu Gly Trp Thr Ala Asp Pro Ile
            20                  25                  30

Ile Gly Val Gly Ser Ala Ala Thr Pro Asp Thr Gly Pro Asp Leu Asp
        35                  40                  45

Asn Ala His Gly Gln Ala Glu Thr Asp Thr Glu Gln Glu Ile Ala Leu
    50                  55                  60

Phe Thr Val Thr Asn Pro Pro Arg Thr Val Ser Val Ser Thr Leu Met
65                  70                  75                  80

Asp Gly Arg Ile Asp His Val Glu Leu Ser Ala Arg Val Ala Trp Met
                85                  90                  95

Ser Glu Ser Gln Leu Ala Ser Glu Ile Leu Val Ile Ala Asp Leu Ala
            100                 105                 110

Arg Gln Lys Ala Gln Ser Ala Gln Tyr Ala Phe Ile Leu Asp Arg Met
        115                 120                 125

Ser Gln Gln Val Asp Ala Asp Glu His Arg Val Ala Leu Leu Arg Lys
    130                 135                 140

Thr Val Gly Glu Thr Trp Gly Leu Pro Ser Pro Glu Glu Ala Ala Ala
145                 150                 155                 160

Ala Glu Ala Glu Val Phe Ala Thr Arg Tyr Ser Asp Ser Pro Ala
                165                 170                 175

Pro Asp Asp Glu Ser Asp Pro Trp Met Thr Glu Asn Leu Thr Val Gln
            180                 185                 190

Pro Glu Arg Leu Gly Val Leu Ala Ser His His Asp Asn Ala Ala Val
        195                 200                 205

Asp Ala Ser Ser Gly Val Glu Ala Ala Gly Leu Gly Glu Ser Val
    210                 215                 220

Ala Ile Thr His Gly Pro Tyr Ser Ser Gln Phe Asn Asp Thr Leu Asn
225                 230                 235                 240

Val Tyr Leu Thr Ala His Asn Ala Leu Gly Ser Ser Leu His Thr Ala
                245                 250                 255

Gly Val Asp Leu Ala Lys Ser Leu Arg Ile Ala Ala Lys Ile Tyr Ser
            260                 265                 270

Glu Ala Asp Glu Ala Trp Arg Lys Ala Ile Asp Gly Leu Phe Thr Met
        275                 280                 285

Thr Gly Phe Leu Gly Val Val Pro Ser Phe Leu Lys Val Leu Ala Gly
    290                 295                 300

Met His Asn Glu Ile Val Gly Asp Ile Lys Arg Ala Thr Asp Thr Val
305                 310                 315                 320

Ala Gly Ile Ser Gly Arg Val Gln Leu Thr His Gly Ser Phe Thr Ser
                325                 330                 335

Lys Phe Asn Asp Thr Leu Gln Glu Phe Glu Thr Thr Arg Ser Ser Thr
            340                 345                 350

Gly Thr Gly Leu Gln Gly Val Thr Ser Gly Leu Ala Asn Asn Leu Leu
        355                 360                 365

Ala Ala Ala Gly Ala Tyr Leu Lys Ala Asp Asp Gly Leu Ala Gly Val
    370                 375                 380
```

```
Ile Asp Lys Ile Phe Gly Met Ser Thr Thr Phe Ala Ala Arg Leu Asn
385                 390                 395                 400

Arg Leu Phe Asp Thr Val Tyr Pro Pro Gly Arg Gly Pro His Thr Ser
            405                 410                 415

Ala Glu Val Ile Ala Ala Leu Lys Ala Glu Gly Ile Thr Met Ser Ala
        420                 425                 430

Pro Tyr Leu Ser Gln Leu Arg Ser Gly Asn Arg Thr Asn Pro Ser Gly
            435                 440                 445

Ala Thr Met Ala Ala Leu Ala Asn Phe Phe Arg Ile Lys Ala Ala Tyr
        450                 455                 460

Phe Thr Asp Asp Glu Tyr Tyr Glu Lys Leu Asp Lys Glu Leu Gln Trp
465                 470                 475                 480

Leu Ser Thr Met Arg Asp Asp Gly Val Arg Arg Ile Ala Gln Arg Ala
                485                 490                 495

His Gly Leu Pro Ser Ala Ala Gln Gln Lys Val Leu Asp Arg Ile Asp
            500                 505                 510

Glu Leu Arg Arg Ala Glu Gly Ile Asp Ala Met Glu Lys Met Ser His
        515                 520                 525

Asp Pro Ile Ala Ala Asp Ile Gly Thr Gln Val Ser Asp Asn Ala Leu
530                 535                 540

His Gly Val Thr Ala Gly Ser Thr Ala Leu Thr Ser Val Thr Gly Leu
545                 550                 555                 560

Val Pro Ala Gly Ala Asp Glu Val Ser Ala Gln Ala Ala Thr Ala Phe
                565                 570                 575

Thr Ser Glu Gly Ile Gln Leu Leu Ala Ser Asn Ala Ser Ala Gln Asp
            580                 585                 590

Gln Leu His Arg Ala Gly Glu Ala Val Gln Asp Val Ala Arg Thr Tyr
        595                 600                 605

Ser Gln Ile Asp Asp Gly Ala Ala Gly Val Phe Ala Glu
610                 615                 620

<210> SEQ ID NO 20
<211> LENGTH: 1013
<212> TYPE: PRT
<213> ORGANISM: Mycobacterium tuberculosis

<400> SEQUENCE: 20

Met Asp Leu Pro Gly Asn Asp Phe Asp Ser Asn Asp Phe Asp Ala Val
1               5                   10                  15

Asp Leu Trp Gly Ala Asp Gly Ala Glu Gly Trp Thr Ala Asp Pro Ile
            20                  25                  30

Ile Gly Val Gly Ser Ala Ala Thr Pro Asp Thr Gly Pro Asp Leu Asp
        35                  40                  45

Asn Ala His Gly Gln Ala Glu Thr Asp Thr Glu Gln Glu Ile Ala Leu
    50                  55                  60

Phe Thr Val Thr Asn Pro Pro Arg Thr Val Ser Val Ser Thr Leu Met
65                  70                  75                  80

Asp Gly Arg Ile Asp His Val Glu Leu Ser Ala Arg Val Ala Trp Met
                85                  90                  95

Ser Glu Ser Gln Leu Ala Ser Glu Ile Leu Val Ile Ala Asp Leu Ala
            100                 105                 110

Arg Gln Lys Ala Gln Ser Ala Gln Tyr Ala Phe Ile Leu Asp Arg Met
        115                 120                 125

Ser Gln Gln Val Asp Ala Asp Glu His Arg Val Ala Leu Leu Arg Lys
```

-continued

```
            130                 135                 140
Thr Val Gly Glu Thr Trp Gly Leu Pro Ser Pro Glu Ala Ala Ala
145                 150                 155                 160

Ala Glu Ala Glu Val Phe Ala Thr Arg Tyr Ser Asp Ser Pro Ala
                165                 170                 175

Pro Asp Asp Glu Ser Asp Pro Trp Met Thr Glu Asn Leu Thr Val Gln
            180                 185                 190

Pro Glu Arg Leu Gly Val Leu Ala Ser His His Asp Asn Ala Ala Val
            195                 200                 205

Asp Ala Ser Ser Gly Val Glu Ala Ala Ala Gly Leu Gly Glu Ser Val
210                 215                 220

Ala Ile Thr His Gly Pro Tyr Ser Ser Gln Phe Asn Asp Thr Leu Asn
225                 230                 235                 240

Val Tyr Leu Thr Ala His Asn Ala Leu Gly Ser Ser Leu His Thr Ala
                245                 250                 255

Gly Val Asp Leu Ala Lys Ser Leu Arg Ile Ala Ala Lys Ile Tyr Ser
                260                 265                 270

Glu Ala Asp Glu Ala Trp Arg Lys Ala Ile Asp Gly Leu Phe Thr Met
            275                 280                 285

Ser Arg Ala Phe Ile Ile Asp Pro Thr Ile Ser Ala Ile Asp Gly Leu
290                 295                 300

Tyr Asp Leu Leu Gly Ile Gly Ile Pro Asn Gln Gly Gly Ile Leu Tyr
305                 310                 315                 320

Ser Ser Leu Glu Tyr Phe Glu Lys Ala Leu Glu Glu Leu Ala Ala Ala
                325                 330                 335

Phe Pro Gly Asp Gly Trp Leu Gly Ser Ala Ala Asp Lys Tyr Ala Gly
            340                 345                 350

Lys Asn Arg Asn His Val Asn Phe Phe Gln Glu Leu Ala Asp Leu Asp
            355                 360                 365

Arg Gln Leu Ile Ser Leu Ile His Asp Gln Ala Asn Ala Val Gln Thr
            370                 375                 380

Thr Arg Asp Ile Leu Glu Gly Ala Lys Lys Gly Leu Glu Phe Val Arg
385                 390                 395                 400

Pro Val Ala Val Asp Leu Thr Tyr Ile Pro Val Val Gly His Ala Leu
                405                 410                 415

Ser Ala Ala Phe Gln Ala Pro Phe Cys Ala Gly Ala Met Ala Val Val
                420                 425                 430

Gly Gly Ala Leu Ala Tyr Leu Val Val Lys Thr Leu Ile Asn Ala Thr
            435                 440                 445

Gln Leu Leu Lys Leu Leu Ala Lys Leu Ala Glu Leu Val Ala Ala Ala
450                 455                 460

Ile Ala Asp Ile Ile Ser Asp Val Ala Asp Ile Lys Gly Thr Leu
465                 470                 475                 480

Gly Glu Val Trp Glu Phe Ile Thr Asn Ala Leu Asn Gly Leu Lys Glu
                485                 490                 495

Leu Trp Asp Lys Leu Thr Gly Trp Val Thr Gly Leu Phe Ser Arg Gly
            500                 505                 510

Trp Ser Asn Leu Glu Ser Phe Phe Ala Gly Val Pro Gly Leu Thr Gly
            515                 520                 525

Ala Thr Ser Gly Leu Ser Gln Val Thr Gly Leu Phe Gly Ala Ala Gly
            530                 535                 540

Leu Ser Ala Ser Ser Gly Leu Ala His Ala Asp Ser Leu Ala Ser Ser
545                 550                 555                 560
```

```
Ala Ser Leu Pro Ala Leu Ala Gly Ile Gly Gly Ser Gly Phe Gly
            565                 570                 575

Gly Leu Pro Ser Leu Ala Gln Val His Ala Ala Ser Thr Arg Gln Ala
            580                 585                 590

Leu Arg Pro Arg Ala Asp Gly Pro Val Gly Ala Ala Glu Gln Val
            595                 600                 605

Gly Gly Gln Ser Gln Leu Val Ser Ala Gln Gly Ser Gln Gly Met Gly
            610                 615                 620

Gly Pro Val Gly Met Gly Gly Met His Pro Ser Ser Gly Ala Ser Lys
625                 630                 635                 640

Gly Thr Thr Thr Lys Lys Tyr Ser Glu Gly Ala Ala Gly Thr Glu
            645                 650                 655

Asp Ala Glu Arg Ala Pro Val Glu Ala Asp Ala Gly Gly Gln Lys
            660                 665                 670

Val Leu Val Arg Asn Val Val Met Thr Gly Phe Leu Gly Val Val Pro
            675                 680                 685

Ser Phe Leu Lys Val Leu Ala Gly Met His Asn Glu Ile Val Gly Asp
            690                 695                 700

Ile Lys Arg Ala Thr Asp Thr Val Ala Gly Ile Ser Gly Arg Val Gln
705                 710                 715                 720

Leu Thr His Gly Ser Phe Thr Ser Lys Phe Asn Asp Thr Leu Gln Glu
            725                 730                 735

Phe Glu Thr Thr Arg Ser Ser Thr Gly Thr Gly Leu Gln Gly Val Thr
            740                 745                 750

Ser Gly Leu Ala Asn Asn Leu Leu Ala Ala Gly Ala Tyr Leu Lys
            755                 760                 765

Ala Asp Asp Gly Leu Ala Gly Val Ile Asp Lys Ile Phe Gly Met Ser
            770                 775                 780

Thr Thr Phe Ala Ala Arg Leu Asn Arg Leu Phe Asp Thr Val Tyr Pro
785                 790                 795                 800

Pro Gly Arg Gly Pro His Thr Ser Ala Glu Val Ile Ala Ala Leu Lys
            805                 810                 815

Ala Glu Gly Ile Thr Met Ser Ala Pro Tyr Leu Ser Gln Leu Arg Ser
            820                 825                 830

Gly Asn Arg Thr Asn Pro Ser Gly Ala Thr Met Ala Ala Leu Ala Asn
            835                 840                 845

Phe Phe Arg Ile Lys Ala Ala Tyr Phe Thr Asp Glu Tyr Tyr Glu
            850                 855                 860

Lys Leu Asp Lys Glu Leu Gln Trp Leu Ser Thr Met Arg Asp Asp Gly
865                 870                 875                 880

Val Arg Arg Ile Ala Gln Arg Ala His Gly Leu Pro Ser Ala Ala Gln
            885                 890                 895

Gln Lys Val Leu Asp Arg Ile Asp Glu Leu Arg Arg Ala Glu Gly Ile
            900                 905                 910

Asp Ala Met Glu Lys Met Ser His Asp Pro Ile Ala Ala Asp Ile Gly
            915                 920                 925

Thr Gln Val Ser Asp Asn Ala Leu His Gly Val Thr Ala Gly Ser Thr
            930                 935                 940

Ala Leu Thr Ser Val Thr Gly Leu Val Pro Ala Gly Ala Asp Glu Val
945                 950                 955                 960

Ser Ala Gln Ala Ala Thr Ala Phe Thr Ser Glu Gly Ile Gln Leu Leu
            965                 970                 975
```

Ala Ser Asn Ala Ser Ala Gln Asp Gln Leu His Arg Ala Gly Glu Ala
            980                 985                 990

Val Gln Asp Val Ala Arg Thr Tyr  Ser Gln Ile Asp Asp  Gly Ala Ala
        995                 1000                1005

Gly Val  Phe Ala Glu
    1010

<210> SEQ ID NO 21
<211> LENGTH: 1473
<212> TYPE: PRT
<213> ORGANISM: Mycobacterium tuberculosis

<400> SEQUENCE: 21

Met Asp Leu Pro Gly Asn Asp Phe Asp Ser Asn Asp Phe Asp Ala Val
1               5                   10                  15

Asp Leu Trp Gly Ala Asp Gly Ala Glu Gly Trp Thr Ala Asp Pro Ile
            20                  25                  30

Ile Gly Val Gly Ser Ala Ala Thr Pro Asp Thr Gly Pro Asp Leu Asp
        35                  40                  45

Asn Ala His Gly Gln Ala Glu Thr Asp Thr Glu Gln Glu Ile Ala Leu
    50                  55                  60

Phe Thr Val Thr Asn Pro Pro Arg Thr Val Ser Val Ser Thr Leu Met
65                  70                  75                  80

Asp Gly Arg Ile Asp His Val Glu Leu Ser Ala Arg Val Ala Trp Met
                85                  90                  95

Ser Glu Ser Gln Leu Ala Ser Glu Ile Leu Val Ile Ala Asp Leu Ala
            100                 105                 110

Arg Gln Lys Ala Gln Ser Ala Gln Tyr Ala Phe Ile Leu Asp Arg Met
        115                 120                 125

Ser Gln Gln Val Asp Ala Asp Glu His Arg Val Ala Leu Leu Arg Lys
    130                 135                 140

Thr Val Gly Glu Thr Trp Gly Leu Pro Ser Pro Glu Glu Ala Ala Ala
145                 150                 155                 160

Ala Glu Ala Glu Val Phe Ala Thr Arg Tyr Ser Asp Ser Pro Ala
                165                 170                 175

Pro Asp Asp Glu Ser Asp Pro Trp Met Thr Glu Asn Leu Thr Val Gln
            180                 185                 190

Pro Glu Arg Leu Gly Val Leu Ala Ser His His Asp Asn Ala Ala Val
        195                 200                 205

Asp Ala Ser Ser Gly Val Glu Ala Ala Ala Gly Leu Gly Glu Ser Val
    210                 215                 220

Ala Ile Thr His Gly Pro Tyr Ser Ser Gln Phe Asn Asp Thr Leu Asn
225                 230                 235                 240

Val Tyr Leu Thr Ala His Asn Ala Leu Gly Ser Ser Leu His Thr Ala
                245                 250                 255

Gly Val Asp Leu Ala Lys Ser Leu Arg Ile Ala Ala Lys Ile Tyr Ser
            260                 265                 270

Glu Ala Asp Glu Ala Trp Arg Lys Ala Ile Asp Gly Leu Phe Thr Met
        275                 280                 285

Ser Arg Ala Phe Ile Ile Asp Pro Thr Ile Ser Ala Ile Asp Gly Leu
    290                 295                 300

Tyr Asp Leu Leu Gly Ile Gly Ile Pro Asn Gln Gly Gly Ile Leu Tyr
305                 310                 315                 320

Ser Ser Leu Glu Tyr Phe Glu Lys Ala Leu Glu Glu Leu Ala Ala Ala
                325                 330                 335

```
Phe Pro Gly Asp Gly Trp Leu Gly Ser Ala Ala Asp Lys Tyr Ala Gly
            340                 345                 350

Lys Asn Arg Asn His Val Asn Phe Gln Glu Leu Ala Asp Leu Asp
        355                 360                 365

Arg Gln Leu Ile Ser Leu Ile His Asp Gln Ala Asn Ala Val Gln Thr
    370                 375                 380

Thr Arg Asp Ile Leu Glu Gly Ala Lys Lys Gly Leu Glu Phe Val Arg
385                 390                 395                 400

Pro Val Ala Val Asp Leu Thr Tyr Ile Pro Val Val Gly His Ala Leu
                405                 410                 415

Ser Ala Ala Phe Gln Ala Pro Phe Cys Ala Gly Ala Met Ala Val Val
            420                 425                 430

Gly Gly Ala Leu Ala Tyr Leu Val Val Lys Thr Leu Ile Asn Ala Thr
        435                 440                 445

Gln Leu Leu Lys Leu Leu Ala Lys Leu Ala Glu Leu Val Ala Ala Ala
    450                 455                 460

Ile Ala Asp Ile Ile Ser Asp Val Ala Asp Ile Ile Lys Gly Thr Leu
465                 470                 475                 480

Met Thr Gln Ser Gln Thr Val Thr Val Asp Gln Gln Glu Ile Leu Asn
                485                 490                 495

Arg Ala Asn Glu Val Glu Ala Pro Met Ala Asp Pro Pro Thr Asp Val
            500                 505                 510

Pro Ile Thr Pro Cys Glu Leu Thr Ala Ala Lys Asn Ala Ala Gln Gln
        515                 520                 525

Leu Val Leu Ser Ala Asp Asn Met Arg Glu Tyr Leu Ala Ala Gly Ala
    530                 535                 540

Lys Glu Arg Gln Arg Leu Ala Thr Ser Leu Arg Asn Ala Ala Lys Ala
545                 550                 555                 560

Tyr Gly Glu Val Asp Glu Glu Ala Ala Thr Ala Leu Asp Asn Asp Gly
                565                 570                 575

Glu Gly Thr Val Gln Ala Glu Ser Ala Gly Ala Val Gly Gly Asp Ser
            580                 585                 590

Ser Ala Glu Leu Thr Asp Thr Pro Arg Val Ala Thr Ala Gly Glu Pro
        595                 600                 605

Asn Phe Met Asp Leu Lys Glu Ala Ala Arg Lys Leu Glu Thr Gly Asp
    610                 615                 620

Gln Gly Ala Ser Leu Ala His Phe Ala Asp Gly Trp Asn Thr Phe Asn
625                 630                 635                 640

Leu Thr Leu Gln Gly Asp Val Lys Arg Phe Arg Gly Phe Asp Asn Trp
                645                 650                 655

Glu Gly Asp Ala Ala Thr Ala Cys Glu Ala Ser Leu Asp Gln Gln Arg
            660                 665                 670

Gln Trp Ile Leu His Met Ala Lys Leu Ser Ala Ala Met Ala Lys Gln
        675                 680                 685

Ala Gln Tyr Val Ala Gln Leu His Val Trp Ala Arg Arg Glu His Pro
    690                 695                 700

Thr Tyr Glu Asp Ile Val Gly Leu Glu Arg Leu Tyr Ala Glu Asn Pro
705                 710                 715                 720

Ser Ala Arg Asp Gln Ile Leu Pro Val Tyr Ala Glu Tyr Gln Gln Arg
                725                 730                 735

Ser Glu Lys Val Leu Thr Glu Tyr Asn Asn Lys Ala Ala Leu Glu Pro
            740                 745                 750
```

-continued

```
Val Asn Pro Pro Lys Pro Pro Ala Ile Lys Ile Asp Pro Pro
        755                 760                 765

Pro Pro Gln Glu Gln Gly Leu Ile Pro Gly Phe Leu Met Pro Pro Ser
770                 775                 780

Asp Gly Ser Gly Val Thr Pro Gly Thr Gly Met Pro Ala Ala Pro Met
785                 790                 795                 800

Val Pro Pro Thr Gly Ser Pro Gly Gly Leu Pro Ala Asp Thr Ala
                805                 810                 815

Ala Gln Leu Thr Ser Ala Gly Arg Glu Ala Ala Leu Ser Gly Asp
            820                 825                 830

Val Ala Val Lys Ala Ala Ser Leu Gly Gly Gly Gly Gly Gly Val
                835                 840                 845

Pro Ser Ala Pro Leu Gly Ser Ala Ile Gly Gly Ala Glu Ser Val Arg
    850                 855                 860

Pro Ala Gly Ala Gly Asp Ile Ala Gly Leu Gly Gln Gly Arg Ala Gly
865                 870                 875                 880

Gly Gly Ala Ala Leu Gly Gly Gly Met Gly Met Pro Met Gly Ala
                885                 890                 895

Ala His Gln Gly Gln Gly Gly Ala Lys Ser Lys Gly Ser Gln Gln Glu
                900                 905                 910

Asp Glu Ala Leu Tyr Thr Glu Asp Arg Ala Trp Thr Glu Ala Val Ile
            915                 920                 925

Gly Asn Arg Arg Arg Gln Asp Ser Lys Glu Ser Lys Gly Glu Val Trp
    930                 935                 940

Glu Phe Ile Thr Asn Ala Leu Asn Gly Leu Lys Glu Leu Trp Asp Lys
945                 950                 955                 960

Leu Thr Gly Trp Val Thr Gly Leu Phe Ser Arg Gly Trp Ser Asn Leu
                965                 970                 975

Glu Ser Phe Phe Ala Gly Val Pro Gly Leu Thr Gly Ala Thr Ser Gly
            980                 985                 990

Leu Ser Gln Val Thr Gly Leu Phe  Gly Ala Ala Gly Leu  Ser Ala Ser
            995                 1000                1005

Ser Gly  Leu Ala His Ala Asp  Ser Leu Ala Ser Ser  Ala Ser Leu
    1010                1015                1020

Pro Ala  Leu Ala Gly Ile Gly  Gly Gly Ser Gly Phe  Gly Gly Leu
    1025                1030                1035

Pro Ser  Leu Ala Gln Val His  Ala Ala Ser Thr Arg  Gln Ala Leu
    1040                1045                1050

Arg Pro  Arg Ala Asp Gly Pro  Val Gly Ala Ala Ala  Glu Gln Val
    1055                1060                1065

Gly Gly  Gln Ser Gln Leu Val  Ser Ala Gln Gly Ser  Gln Gly Met
    1070                1075                1080

Gly Gly  Pro Val Gly Met Gly  Gly Met His Pro Ser  Ser Gly Ala
    1085                1090                1095

Ser Lys  Gly Thr Thr Thr Lys  Lys Tyr Ser Glu Gly  Ala Ala Ala
    1100                1105                1110

Gly Thr  Glu Asp Ala Glu Arg  Ala Pro Val Glu Ala  Asp Ala Gly
    1115                1120                1125

Gly Gly  Gln Lys Val Leu Val  Arg Asn Val Val Met  Thr Gly Phe
    1130                1135                1140

Leu Gly  Val Val Pro Ser Phe  Leu Lys Val Leu Ala  Gly Met His
    1145                1150                1155

Asn Glu  Ile Val Gly Asp Ile  Lys Arg Ala Thr Asp  Thr Val Ala
```

1160                1165                1170

Gly Ile Ser Gly Arg Val Gln Leu Thr His Gly Ser Phe Thr Ser
        1175                1180                1185

Lys Phe Asn Asp Thr Leu Gln Glu Phe Glu Thr Thr Arg Ser Ser
        1190                1195                1200

Thr Gly Thr Gly Leu Gln Gly Val Thr Ser Gly Leu Ala Asn Asn
        1205                1210                1215

Leu Leu Ala Ala Ala Gly Ala Tyr Leu Lys Ala Asp Asp Gly Leu
        1220                1225                1230

Ala Gly Val Ile Asp Lys Ile Phe Gly Met Ser Thr Thr Phe Ala
        1235                1240                1245

Ala Arg Leu Asn Arg Leu Phe Asp Thr Val Tyr Pro Pro Gly Arg
        1250                1255                1260

Gly Pro His Thr Ser Ala Glu Val Ile Ala Ala Leu Lys Ala Glu
        1265                1270                1275

Gly Ile Thr Met Ser Ala Pro Tyr Leu Ser Gln Leu Arg Ser Gly
        1280                1285                1290

Asn Arg Thr Asn Pro Ser Gly Ala Thr Met Ala Ala Leu Ala Asn
        1295                1300                1305

Phe Phe Arg Ile Lys Ala Ala Tyr Phe Thr Asp Asp Glu Tyr Tyr
        1310                1315                1320

Glu Lys Leu Asp Lys Glu Leu Gln Trp Leu Ser Thr Met Arg Asp
        1325                1330                1335

Asp Gly Val Arg Arg Ile Ala Gln Arg Ala His Gly Leu Pro Ser
        1340                1345                1350

Ala Ala Gln Gln Lys Val Leu Asp Arg Ile Asp Glu Leu Arg Arg
        1355                1360                1365

Ala Glu Gly Ile Asp Ala Met Glu Lys Met Ser His Asp Pro Ile
        1370                1375                1380

Ala Ala Asp Ile Gly Thr Gln Val Ser Asp Asn Ala Leu His Gly
        1385                1390                1395

Val Thr Ala Gly Ser Thr Ala Leu Thr Ser Val Thr Gly Leu Val
        1400                1405                1410

Pro Ala Gly Ala Asp Glu Val Ser Ala Gln Ala Ala Thr Ala Phe
        1415                1420                1425

Thr Ser Glu Gly Ile Gln Leu Leu Ala Ser Asn Ala Ser Ala Gln
        1430                1435                1440

Asp Gln Leu His Arg Ala Gly Glu Ala Val Gln Asp Val Ala Arg
        1445                1450                1455

Thr Tyr Ser Gln Ile Asp Asp Gly Ala Ala Gly Val Phe Ala Glu
        1460                1465                1470

<210> SEQ ID NO 22
<211> LENGTH: 1081
<212> TYPE: PRT
<213> ORGANISM: Mycobacterium tuberculosis

<400> SEQUENCE: 22

Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Thr Asp Val
            20                  25                  30

Pro Ile Thr Pro Cys Glu Leu Thr Ala Ala Lys Asn Ala Ala Gln Gln
        35                  40                  45

```
Leu Val Leu Ser Ala Asp Asn Met Arg Glu Tyr Leu Ala Ala Gly Ala
     50                   55                      60

Lys Glu Arg Gln Arg Leu Ala Thr Ser Leu Arg Asn Ala Ala Lys Ala
 65                  70                   75                   80

Tyr Gly Glu Val Asp Glu Ala Ala Thr Ala Leu Asp Asn Asp Gly
                 85                   90                   95

Glu Gly Thr Val Gln Ala Glu Ser Ala Gly Val Gly Gly Asp Ser
                100                  105                 110

Ser Ala Glu Leu Thr Asp Thr Pro Arg Val Ala Thr Ala Gly Glu Pro
             115                 120                 125

Asn Phe Met Asp Leu Lys Glu Ala Arg Lys Leu Glu Thr Gly Asp
130                 135                 140

Gln Gly Ala Ser Leu Ala His Phe Ala Asp Gly Trp Asn Thr Phe Asn
145             150                 155                     160

Leu Thr Leu Gln Gly Asp Val Lys Arg Phe Arg Gly Phe Asp Asn Trp
                165                 170                 175

Glu Gly Asp Ala Ala Thr Ala Cys Glu Ala Ser Leu Asp Gln Gln Arg
             180                 185                 190

Gln Trp Ile Leu His Met Ala Lys Leu Ser Ala Met Ala Lys Gln
             195                 200                 205

Ala Gln Tyr Val Ala Gln Leu His Val Trp Ala Arg Arg Glu His Pro
             210                 215                 220

Thr Tyr Glu Asp Ile Val Gly Leu Glu Arg Leu Tyr Ala Glu Asn Pro
225                 230                 235                 240

Ser Ala Arg Asp Gln Ile Leu Pro Val Tyr Ala Glu Tyr Gln Gln Arg
                245                 250                 255

Ser Glu Lys Val Leu Thr Glu Tyr Asn Asn Lys Ala Ala Leu Glu Pro
             260                 265                 270

Val Asn Pro Pro Lys Pro Pro Ala Ile Lys Ile Asp Pro Pro
         275                 280                 285

Pro Pro Gln Glu Gln Gly Leu Ile Pro Gly Phe Leu Met Pro Pro Ser
     290                 295                 300

Asp Gly Ser Gly Val Thr Pro Gly Thr Gly Met Pro Ala Ala Pro Met
305                 310                 315                 320

Val Pro Pro Thr Gly Ser Pro Gly Gly Leu Pro Ala Asp Thr Ala
                 325                 330                 335

Ala Gln Leu Thr Ser Ala Gly Arg Glu Ala Ala Leu Ser Gly Asp
             340                 345                 350

Val Ala Val Lys Ala Ala Ser Leu Gly Gly Gly Gly Gly Val
             355                 360                 365

Pro Ser Ala Pro Leu Gly Ser Ala Ile Gly Gly Ala Glu Ser Val Arg
370                 375                 380

Pro Ala Gly Ala Gly Asp Ile Ala Gly Leu Gly Gln Gly Arg Ala Gly
385                 390                 395                 400

Gly Gly Ala Ala Leu Gly Gly Gly Met Gly Met Pro Met Gly Ala
                405                 410                 415

Ala His Gln Gly Gln Gly Gly Ala Lys Ser Lys Gly Ser Gln Gln Glu
             420                 425                 430

Asp Glu Ala Leu Tyr Thr Glu Asp Arg Ala Trp Thr Glu Ala Val Ile
             435                 440                 445

Gly Asn Arg Arg Gln Asp Ser Lys Glu Ser Lys Met Asp Leu Pro
450                 455                 460

Gly Asn Asp Phe Asp Ser Asn Asp Phe Asp Ala Val Asp Leu Trp Gly
```

```
            465                 470                 475                 480
        Ala Asp Gly Ala Glu Gly Trp Thr Ala Asp Pro Ile Ile Gly Val Gly
                        485                 490                 495

Ser Ala Ala Thr Pro Asp Thr Gly Pro Asp Leu Asp Asn Ala His Gly
                    500                 505                 510

Gln Ala Glu Thr Asp Thr Glu Gln Glu Ile Ala Leu Phe Thr Val Thr
                    515                 520                 525

Asn Pro Pro Arg Thr Val Ser Val Ser Thr Leu Met Asp Gly Arg Ile
                    530                 535                 540

Asp His Val Glu Leu Ser Ala Arg Val Ala Trp Met Ser Glu Ser Gln
        545                 550                 555                 560

Leu Ala Ser Glu Ile Leu Val Ile Ala Asp Leu Ala Arg Gln Lys Ala
                        565                 570                 575

Gln Ser Ala Gln Tyr Ala Phe Ile Leu Asp Arg Met Ser Gln Gln Val
                    580                 585                 590

Asp Ala Asp Glu His Arg Val Ala Leu Leu Arg Lys Thr Val Gly Glu
                    595                 600                 605

Thr Trp Gly Leu Pro Ser Pro Glu Ala Ala Ala Glu Ala Glu
                610                 615                 620

Val Phe Ala Thr Arg Tyr Ser Asp Asp Ser Pro Ala Pro Asp Asp Glu
        625                 630                 635                 640

Ser Asp Pro Trp Met Thr Glu Asn Leu Thr Val Gln Pro Glu Arg Leu
                        645                 650                 655

Gly Val Leu Ala Ser His His Asp Asn Ala Ala Val Asp Ala Ser Ser
                    660                 665                 670

Gly Val Glu Ala Ala Ala Gly Leu Gly Glu Ser Val Ala Ile Thr His
                    675                 680                 685

Gly Pro Tyr Ser Ser Gln Phe Asn Asp Thr Leu Asn Val Tyr Leu Thr
                    690                 695                 700

Ala His Asn Ala Leu Gly Ser Ser Leu His Thr Ala Gly Val Asp Leu
        705                 710                 715                 720

Ala Lys Ser Leu Arg Ile Ala Ala Lys Ile Tyr Ser Glu Ala Asp Glu
                        725                 730                 735

Ala Trp Arg Lys Ala Ile Asp Gly Leu Phe Thr Met Thr Gly Phe Leu
                    740                 745                 750

Gly Val Val Pro Ser Phe Leu Lys Val Leu Ala Gly Met His Asn Glu
                    755                 760                 765

Ile Val Gly Asp Ile Lys Arg Ala Thr Asp Thr Val Ala Gly Ile Ser
        770                 775                 780

Gly Arg Val Gln Leu Thr His Gly Ser Phe Thr Ser Lys Phe Asn Asp
        785                 790                 795                 800

Thr Leu Gln Glu Phe Glu Thr Thr Arg Ser Ser Thr Gly Thr Gly Leu
                        805                 810                 815

Gln Gly Val Thr Ser Gly Leu Ala Asn Asn Leu Leu Ala Ala Ala Gly
                    820                 825                 830

Ala Tyr Leu Lys Ala Asp Asp Gly Leu Ala Gly Val Ile Asp Lys Ile
                    835                 840                 845

Phe Gly Met Ser Thr Thr Phe Ala Ala Arg Leu Asn Arg Leu Phe Asp
        850                 855                 860

Thr Val Tyr Pro Pro Gly Arg Gly Pro His Thr Ser Ala Glu Val Ile
        865                 870                 875                 880

Ala Ala Leu Lys Ala Glu Gly Ile Thr Met Ser Ala Pro Tyr Leu Ser
                        885                 890                 895
```

```
Gln Leu Arg Ser Gly Asn Arg Thr Asn Pro Ser Gly Ala Thr Met Ala
            900                 905                 910

Ala Leu Ala Asn Phe Phe Arg Ile Lys Ala Ala Tyr Phe Thr Asp Asp
            915                 920                 925

Glu Tyr Tyr Glu Lys Leu Asp Lys Glu Leu Gln Trp Leu Ser Thr Met
930                 935                 940

Arg Asp Asp Gly Val Arg Ile Ala Gln Arg Ala His Gly Leu Pro
945                 950                 955                 960

Ser Ala Ala Gln Gln Lys Val Leu Asp Arg Ile Asp Glu Leu Arg Arg
            965                 970                 975

Ala Glu Gly Ile Asp Ala Met Glu Lys Met Ser His Asp Pro Ile Ala
            980                 985                 990

Ala Asp Ile Gly Thr Gln Val Ser Asp Asn Ala Leu His Gly Val Thr
            995                1000                1005

Ala Gly Ser Thr Ala Leu Thr Ser Val Thr Gly Leu Val Pro Ala
           1010                1015                1020

Gly Ala Asp Glu Val Ser Ala Gln Ala Ala Thr Ala Phe Thr Ser
           1025                1030                1035

Glu Gly Ile Gln Leu Leu Ala Ser Asn Ala Ser Ala Gln Asp Gln
           1040                1045                1050

Leu His Arg Ala Gly Glu Ala Val Gln Asp Val Ala Arg Thr Tyr
           1055                1060                1065

Ser Gln Ile Asp Asp Gly Ala Ala Gly Val Phe Ala Glu
           1070                1075                1080

<210> SEQ ID NO 23
<211> LENGTH: 653
<212> TYPE: PRT
<213> ORGANISM: Mycobacterium tuberculosis

<400> SEQUENCE: 23

Ala Asp Thr Ile Gln Val Thr Pro Gln Met Leu Arg Ser Thr Ala Asn
1               5                   10                  15

Asp Ile Gln Ala Asn Met Glu Gln Ala Met Gly Ile Ala Lys Gly Tyr
            20                  25                  30

Leu Ala Asn Gln Glu Asn Val Met Asn Pro Ala Thr Trp Ser Gly Thr
        35                  40                  45

Gly Val Val Ala Ser His Met Thr Ala Thr Glu Ile Thr Asn Glu Leu
    50                  55                  60

Asn Lys Val Leu Thr Gly Gly Thr Arg Leu Ala Glu Gly Leu Val Gln
65                  70                  75                  80

Ala Ala Ala Leu Met Glu Gly His Glu Ala Asp Ser Gln Thr Ala Phe
                85                  90                  95

Gln Ala Leu Phe Gly Ala Ser His Gly Ser Gly Leu Val Pro Arg Gly
            100                 105                 110

Ser Thr Gly Met Ser Asp Gln Ile Thr Tyr Asn Pro Gly Ala Val Ser
        115                 120                 125

Asp Phe Ala Ser Asp Val Gly Ser Arg Ala Gly Gln Leu His Met Ile
    130                 135                 140

Tyr Glu Asp Thr Ala Ser Lys Thr Asn Ala Leu Gln Glu Phe Phe Ala
145                 150                 155                 160

Gly His Gly Ala Gln Gly Phe Phe Asp Ala Gln Ala Gln Met Leu Ser
                165                 170                 175

Gly Leu Gln Gly Leu Ile Glu Thr Val Gly Gln His Gly Thr Thr Thr
```

-continued

```
                180                 185                 190
Gly His Val Leu Asp Asn Ala Ile Gly Thr Asp Gln Ala Ile Ala Gly
            195                 200                 205

Leu Phe Leu Ile Gly Ala His Pro Arg Ala Leu Asn Val Val Lys Phe
    210                 215                 220

Gly Gly Ala Ala Phe Leu Met Ser Leu Leu Asp Ala His Ile Pro Gln
225                 230                 235                 240

Leu Val Ala Ser Gln Ser Ala Phe Ala Ala Lys Ala Gly Leu Met Arg
                245                 250                 255

His Thr Ile Gly Gln Ala Glu Gln Ala Ala Met Ser Ala Gln Ala Phe
            260                 265                 270

His Gln Gly Glu Ser Ser Ala Ala Phe Gln Ala Ala His Ala Arg Phe
        275                 280                 285

Val Ala Ala Ala Lys Val Asn Thr Leu Leu Asp Val Ala Gln Ala
    290                 295                 300

Asn Leu Gly Glu Ala Ala Gly Thr Tyr Val Ala Ala Asp Ala Ala Ala
305                 310                 315                 320

Ala Ser Thr Tyr Thr Gly Phe Gly Leu Val Pro Arg Gly Ser Thr Gly
                325                 330                 335

Met Ser Gln Ile Met Tyr Asn Tyr Pro Ala Met Leu Gly His Ala Gly
            340                 345                 350

Asp Met Ala Gly Tyr Ala Gly Thr Leu Gln Ser Leu Gly Ala Glu Ile
        355                 360                 365

Ala Val Glu Gln Ala Ala Leu Gln Ser Ala Trp Gln Gly Asp Thr Gly
    370                 375                 380

Ile Thr Tyr Gln Ala Trp Gln Ala Gln Trp Asn Gln Ala Met Glu Asp
385                 390                 395                 400

Leu Val Arg Ala Tyr His Ala Met Ser Ser Thr His Glu Ala Asn Thr
                405                 410                 415

Met Ala Met Met Ala Arg Asp Thr Ala Glu Ala Ala Lys Trp Gly Gly
            420                 425                 430

Leu Gly Phe Gly Ala Gly Arg Leu Arg Gly Leu Phe Thr Asn Pro Gly
        435                 440                 445

Ser Trp Arg Ile Met Thr Ser Arg Phe Met Thr Asp Pro His Ala Met
    450                 455                 460

Arg Asp Met Ala Gly Arg Phe Glu Val His Ala Gln Thr Val Glu Asp
465                 470                 475                 480

Glu Ala Arg Arg Met Trp Ala Ser Ala Gln Asn Ile Ser Gly Ala Gly
                485                 490                 495

Trp Ser Gly Met Ala Glu Ala Thr Ser Leu Asp Thr Met Thr Gln Met
            500                 505                 510

Asn Gln Ala Phe Arg Asn Ile Val Asn Met Leu His Gly Val Arg Asp
        515                 520                 525

Gly Leu Val Arg Asp Ala Asn Asn Tyr Glu Gln Gln Glu Gln Ala Ser
    530                 535                 540

Gln Gln Ile Leu Ser Ser Gly Leu Val Pro Arg Gly Ser Thr Gly Met
545                 550                 555                 560

Thr Ile Asn Tyr Gln Phe Gly Asp Val Asp Ala His Gly Ala Met Ile
                565                 570                 575

Arg Ala Gln Ala Gly Ser Leu Glu Ala Glu His Gln Ala Ile Ile Ser
            580                 585                 590

Asp Val Leu Thr Ala Ser Asp Phe Trp Gly Gly Ala Gly Ser Ala Ala
        595                 600                 605
```

```
Ser Gln Gly Phe Ile Thr Gln Leu Gly Arg Asn Phe Gln Val Ile Tyr
        610                 615                 620

Glu Gln Ala Asn Ala His Gly Gln Lys Val Gln Ala Ala Gly Asn Asn
625                 630                 635                 640

Met Ala Gln Thr Asp Ser Ala Val Gly Ser Ser Trp Ala
                645                 650

<210> SEQ ID NO 24
<211> LENGTH: 1267
<212> TYPE: PRT
<213> ORGANISM: Mycobacterium tuberculosis

<400> SEQUENCE: 24

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
        35                  40                  45

Ala Phe Pro Gly Asp Gly Trp Leu Gly Ser Ala Asp Lys Tyr Ala
    50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
        115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
            180                 185                 190

Leu Gly Glu Val Trp Glu Phe Ile Thr Asn Ala Leu Asn Gly Leu Lys
        195                 200                 205

Glu Leu Trp Asp Lys Leu Thr Gly Trp Val Thr Gly Leu Phe Ser Arg
    210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
            260                 265                 270

Ser Ala Ser Leu Pro Ala Leu Ala Gly Ile Gly Gly Ser Gly Phe
        275                 280                 285

Gly Gly Leu Pro Ser Leu Ala Gln Val His Ala Ala Ser Thr Arg Gln
    290                 295                 300

Ala Leu Arg Pro Arg Ala Asp Gly Pro Val Gly Ala Ala Ala Glu Gln
305                 310                 315                 320

Val Gly Gly Gln Ser Gln Leu Val Ser Ala Gln Gly Ser Gln Gly Met
```

```
                    325                 330                 335
Gly Gly Pro Val Gly Met Gly Met His Pro Ser Ser Gly Ala Ser
                340                 345                 350
Lys Gly Thr Thr Thr Lys Lys Tyr Ser Glu Gly Ala Ala Gly Thr
                355                 360                 365
Glu Asp Ala Glu Arg Ala Pro Val Glu Ala Asp Ala Gly Gly Gln
            370                 375                 380
Lys Val Leu Val Arg Asn Val Val Met Thr Glu Asn Leu Thr Val Gln
385                 390                 395                 400
Pro Glu Arg Leu Gly Val Leu Ala Ser His His Asp Asn Ala Ala Val
                405                 410                 415
Asp Ala Ser Ser Gly Val Glu Ala Ala Ala Gly Leu Gly Glu Ser Val
                420                 425                 430
Ala Ile Thr His Gly Pro Tyr Cys Ser Gln Phe Asn Asp Thr Leu Asn
                435                 440                 445
Val Tyr Leu Thr Ala His Asn Ala Leu Gly Ser Ser Leu His Thr Ala
            450                 455                 460
Gly Val Asp Leu Ala Lys Ser Leu Arg Ile Ala Ala Lys Ile Tyr Ser
465                 470                 475                 480
Glu Ala Asp Glu Ala Trp Arg Lys Ala Ile Asp Gly Leu Phe Thr Val
                485                 490                 495
Phe Ser Ile Thr Thr Leu Arg Asp Trp Thr Pro Asp Pro Gly Ser Ile
                500                 505                 510
Ile Cys Trp His Ala Ser Pro Thr Ala Lys Ala Lys Ala Arg Gln Ala
                515                 520                 525
Pro Ile Ser Glu Val Pro Pro Ser Tyr Gln Gln Ala Gln His Leu Arg
            530                 535                 540
Arg Tyr Arg Asp His Val Ala Arg Gly Leu Asp Met Ser Arg Leu Met
545                 550                 555                 560
Ile Phe Thr Trp Asp Leu Pro Gly Arg Cys Asn Ile Arg Ala Met Asn
                565                 570                 575
Tyr Ala Ile Asn Ala His Leu Arg Arg His Asp Thr Tyr His Ser Trp
            580                 585                 590
Phe Glu Phe Asp Asn Ala Glu His Ile Val Arg His Thr Ile Ala Asp
            595                 600                 605
Pro Ala Asp Ile Glu Val Val Gln Ala Glu His Gln Asn Met Thr Ser
        610                 615                 620
Ala Glu Leu Arg His His Ile Ala Thr Pro Gln Pro Leu Gln Trp Asp
625                 630                 635                 640
Cys Phe Leu Phe Gly Ile Ile Gln Ser Asp Asp His Phe Thr Phe Tyr
                645                 650                 655
Ala Ser Ile Ala His Leu Cys Val Asp Pro Met Ile Val Gly Val Leu
            660                 665                 670
Phe Ile Glu Ile His Met Met Tyr Ser Ala Leu Val Gly Gly Asp Pro
            675                 680                 685
Pro Ile Glu Leu Pro Pro Ala Gly Arg Tyr Asp Asp His Cys Val Arg
        690                 695                 700
Gln Tyr Ala Asp Thr Ala Ala Leu Thr Leu Asp Ser Ala Arg Val Arg
705                 710                 715                 720
Arg Trp Val Glu Phe Ala Ala Asn Asn Asp Gly Thr Leu Pro His Phe
                725                 730                 735
Pro Leu Pro Leu Gly Asp Leu Ser Val Pro His Thr Gly Lys Leu Leu
            740                 745                 750
```

```
Thr Glu Thr Leu Met Asp Glu Gln Gln Gly Glu Arg Phe Glu Ala Ala
            755                 760                 765

Cys Val Ala Ala Gly Ala Arg Phe Ser Gly Gly Val Phe Ala Cys Ala
770                 775                 780

Ala Leu Ala Glu Arg Glu Leu Thr Asn Cys Glu Thr Phe Asp Val Val
785                 790                 795                 800

Thr Thr Thr Asp Thr Arg Arg Thr Pro Thr Glu Leu Arg Thr Thr Gly
                805                 810                 815

Trp Phe Thr Gly Leu Val Pro Ile Thr Val Pro Val Ala Ser Gly Leu
            820                 825                 830

Phe Asp Ser Ala Ala Arg Val Ala Gln Ile Ser Phe Asp Ser Gly Lys
                835                 840                 845

Asp Leu Ala Thr Val Pro Phe Asp Arg Val Leu Glu Leu Ala Arg Pro
            850                 855                 860

Glu Thr Gly Leu Arg Pro Pro Arg Pro Gly Asn Phe Val Met Ser Phe
865                 870                 875                 880

Leu Asp Ala Ser Ile Ala Pro Leu Ser Thr Val Ala Asn Ser Asp Leu
                885                 890                 895

Asn Phe Arg Ile Tyr Asp Glu Gly Arg Val Ser His Gln Val Ser Met
            900                 905                 910

Trp Val Asn Arg Tyr Gln His Gln Thr Thr Val Thr Val Leu Phe Pro
            915                 920                 925

Asp Asn Pro Ile Ala Ser Glu Ser Val Ala Asn Tyr Ile Ala Ala Met
930                 935                 940

Lys Ser Ile Tyr Ile Arg Thr Ala Asp Gly Thr Leu Ala Thr Leu Lys
945                 950                 955                 960

Pro Gly Thr Met Met Gln Phe Tyr Asp Asp Gly Val Val Gln Leu Asp
                965                 970                 975

Arg Ala Ala Leu Thr Leu Arg Arg Tyr His Phe Pro Ser Gly Thr Ala
            980                 985                 990

Lys Val Ile Pro Leu Asp Gln Ile Arg Gly Tyr Gln Ala Glu Ser Leu
            995                 1000                1005

Gly Phe Leu Met Ala Arg Phe Asn Ile Trp Gly Arg Pro Asp Leu
    1010                1015                1020

Arg Arg Trp Leu Pro Leu Asp Val Tyr Arg Pro Leu Lys Ser Thr
    1025                1030                1035

Leu Val Thr Leu Asp Val Pro Gly Met Arg Pro Lys Pro Ala Cys
    1040                1045                1050

Thr Pro Thr Arg Pro Lys Glu Phe Ile Ala Leu Leu Asp Glu Leu
    1055                1060                1065

Leu Ala Leu His Arg Thr Met Ser Leu Leu Asp Ala His Ile Pro
    1070                1075                1080

Gln Leu Val Ala Ser Gln Ser Ala Phe Ala Ala Lys Ala Gly Leu
    1085                1090                1095

Met Arg His Thr Ile Gly Gln Ala Glu Gln Ala Ala Met Ser Ala
    1100                1105                1110

Gln Ala Phe His Gln Gly Glu Ser Ser Ala Ala Phe Gln Ala Ala
    1115                1120                1125

His Ala Arg Phe Val Ala Ala Ala Lys Val Asn Thr Leu Leu
    1130                1135                1140

Asp Val Ala Gln Ala Asn Leu Gly Glu Ala Ala Gly Thr Tyr Val
    1145                1150                1155
```

```
Ala Ala Asp Ala Ala Ala Ala Ser Thr Tyr Thr Gly Phe Met Ser
    1160                1165                1170

Gln Ile Met Tyr Asn Tyr Pro Ala Met Leu Gly His Ala Gly Asp
    1175                1180                1185

Met Ala Gly Tyr Ala Gly Thr Leu Gln Ser Leu Gly Ala Glu Ile
    1190                1195                1200

Ala Val Glu Gln Ala Ala Leu Gln Ser Ala Trp Gln Gly Asp Thr
    1205                1210                1215

Gly Ile Thr Tyr Gln Ala Trp Gln Ala Gln Trp Asn Gln Ala Met
    1220                1225                1230

Glu Asp Leu Val Arg Ala Tyr His Ala Met Ser Ser Thr His Glu
    1235                1240                1245

Ala Asn Thr Met Ala Met Met Ala Arg Asp Thr Ala Glu Ala Ala
    1250                1255                1260

Lys Trp Gly Gly
    1265

<210> SEQ ID NO 25
<211> LENGTH: 1727
<212> TYPE: PRT
<213> ORGANISM: Mycobacterium tuberculosis

<400> SEQUENCE: 25

Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Thr Asp Val
            20                  25                  30

Pro Ile Thr Pro Cys Glu Leu Thr Ala Ala Lys Asn Ala Ala Gln Gln
        35                  40                  45

Leu Val Leu Ser Ala Asp Asn Met Arg Glu Tyr Leu Ala Ala Gly Ala
    50                  55                  60

Lys Glu Arg Gln Arg Leu Ala Thr Ser Leu Arg Asn Ala Ala Lys Ala
65                  70                  75                  80

Tyr Gly Glu Val Asp Glu Glu Ala Ala Thr Ala Leu Asp Asn Asp Gly
                85                  90                  95

Glu Gly Thr Val Gln Ala Glu Ser Ala Gly Ala Val Gly Gly Asp Ser
            100                 105                 110

Ser Ala Glu Leu Thr Asp Thr Pro Arg Val Ala Thr Ala Gly Glu Pro
        115                 120                 125

Asn Phe Met Asp Leu Lys Glu Ala Ala Arg Lys Leu Glu Thr Gly Asp
    130                 135                 140

Gln Gly Ala Ser Leu Ala His Phe Ala Asp Gly Trp Asn Thr Phe Asn
145                 150                 155                 160

Leu Thr Leu Gln Gly Asp Val Lys Arg Phe Arg Gly Phe Asp Asn Trp
                165                 170                 175

Glu Gly Asp Ala Ala Thr Ala Cys Glu Ala Ser Leu Asp Gln Gln Arg
            180                 185                 190

Gln Trp Ile Leu His Met Ala Lys Leu Ser Ala Ala Met Ala Lys Gln
        195                 200                 205

Ala Gln Tyr Val Ala Gln Leu His Val Trp Ala Arg Arg Glu His Pro
    210                 215                 220

Thr Tyr Glu Asp Ile Val Gly Leu Glu Arg Leu Tyr Ala Glu Asn Pro
225                 230                 235                 240

Ser Ala Arg Asp Gln Ile Leu Pro Val Tyr Ala Glu Tyr Gln Gln Arg
                245                 250                 255
```

```
Ser Glu Lys Val Leu Thr Glu Tyr Asn Asn Lys Ala Ala Leu Glu Pro
            260                 265                 270

Val Asn Pro Pro Lys Pro Pro Ala Ile Lys Ile Asp Pro Pro Pro
        275                 280                 285

Pro Pro Gln Glu Gln Gly Leu Ile Pro Gly Phe Leu Met Pro Pro Ser
    290                 295                 300

Asp Gly Ser Gly Val Thr Pro Gly Thr Gly Met Pro Ala Ala Pro Met
305                 310                 315                 320

Val Pro Pro Thr Gly Ser Pro Gly Gly Leu Pro Ala Asp Thr Ala
                325                 330                 335

Ala Gln Leu Thr Ser Ala Gly Arg Glu Ala Ala Ala Leu Ser Gly Asp
            340                 345                 350

Val Ala Val Lys Ala Ala Ser Leu Gly Gly Gly Gly Gly Gly Val
            355                 360                 365

Pro Ser Ala Pro Leu Gly Ser Ala Ile Gly Gly Ala Glu Ser Val Arg
    370                 375                 380

Pro Ala Gly Ala Gly Asp Ile Ala Gly Leu Gly Gln Gly Arg Ala Gly
385                 390                 395                 400

Gly Gly Ala Ala Leu Gly Gly Gly Met Gly Met Pro Met Gly Ala
            405                 410                 415

Ala His Gln Gly Gln Gly Gly Ala Lys Ser Lys Gly Ser Gln Gln Glu
            420                 425                 430

Asp Glu Ala Leu Tyr Thr Glu Asp Arg Ala Trp Thr Glu Ala Val Ile
            435                 440                 445

Gly Asn Arg Arg Arg Gln Asp Ser Lys Glu Ser Lys Met Ser Arg Ala
        450                 455                 460

Phe Ile Ile Asp Pro Thr Ile Ser Ala Ile Asp Gly Leu Tyr Asp Leu
465                 470                 475                 480

Leu Gly Ile Gly Ile Pro Asn Gln Gly Gly Ile Leu Tyr Ser Ser Leu
                485                 490                 495

Glu Tyr Phe Glu Lys Ala Leu Glu Glu Leu Ala Ala Ala Phe Pro Gly
            500                 505                 510

Asp Gly Trp Leu Gly Ser Ala Ala Asp Lys Tyr Ala Gly Lys Asn Arg
        515                 520                 525

Asn His Val Asn Phe Phe Gln Glu Leu Ala Asp Leu Asp Arg Gln Leu
        530                 535                 540

Ile Ser Leu Ile His Asp Gln Ala Asn Ala Val Gln Thr Thr Arg Asp
545                 550                 555                 560

Ile Leu Glu Gly Ala Lys Lys Gly Leu Glu Phe Val Arg Pro Val Ala
                565                 570                 575

Val Asp Leu Thr Tyr Ile Pro Val Val Gly His Ala Leu Ser Ala Ala
            580                 585                 590

Phe Gln Ala Pro Phe Cys Ala Gly Ala Met Ala Val Gly Gly Ala
            595                 600                 605

Leu Ala Tyr Leu Val Val Lys Thr Leu Ile Asn Ala Thr Gln Leu Leu
        610                 615                 620

Lys Leu Leu Ala Lys Leu Ala Glu Leu Val Ala Ala Ile Ala Asp
625                 630                 635                 640

Ile Ile Ser Asp Val Ala Asp Ile Ile Lys Gly Thr Leu Gly Glu Val
                645                 650                 655

Trp Glu Phe Ile Thr Asn Ala Leu Asn Gly Leu Lys Glu Leu Trp Asp
            660                 665                 670
```

-continued

```
Lys Leu Thr Gly Trp Val Thr Gly Leu Phe Ser Arg Gly Trp Ser Asn
            675                 680                 685
Leu Glu Ser Phe Phe Ala Gly Val Pro Gly Leu Thr Gly Ala Thr Ser
        690                 695                 700
Gly Leu Ser Gln Val Thr Gly Leu Phe Gly Ala Ala Gly Leu Ser Ala
705                 710                 715                 720
Ser Ser Gly Leu Ala His Ala Asp Ser Leu Ala Ser Ser Ala Ser Leu
                725                 730                 735
Pro Ala Leu Ala Gly Ile Gly Gly Ser Gly Phe Gly Gly Leu Pro
            740                 745                 750
Ser Leu Ala Gln Val His Ala Ala Ser Thr Arg Gln Ala Leu Arg Pro
        755                 760                 765
Arg Ala Asp Gly Pro Val Gly Ala Ala Glu Gln Val Gly Gly Gln
    770                 775                 780
Ser Gln Leu Val Ser Ala Gln Gly Ser Gln Gly Met Gly Gly Pro Val
785                 790                 795                 800
Gly Met Gly Gly Met His Pro Ser Ser Gly Ala Ser Lys Gly Thr Thr
                805                 810                 815
Thr Lys Lys Tyr Ser Glu Gly Ala Ala Ala Gly Thr Glu Asp Ala Glu
            820                 825                 830
Arg Ala Pro Val Glu Ala Asp Ala Gly Gly Gly Gln Lys Val Leu Val
        835                 840                 845
Arg Asn Val Val Met Thr Glu Asn Leu Thr Val Gln Pro Glu Arg Leu
    850                 855                 860
Gly Val Leu Ala Ser His His Asp Asn Ala Ala Val Asp Ala Ser Ser
865                 870                 875                 880
Gly Val Glu Ala Ala Ala Gly Leu Gly Glu Ser Val Ala Ile Thr His
                885                 890                 895
Gly Pro Tyr Cys Ser Gln Phe Asn Asp Thr Leu Asn Val Tyr Leu Thr
            900                 905                 910
Ala His Asn Ala Leu Gly Ser Ser Leu His Thr Ala Gly Val Asp Leu
        915                 920                 925
Ala Lys Ser Leu Arg Ile Ala Ala Lys Ile Tyr Ser Glu Ala Asp Glu
    930                 935                 940
Ala Trp Arg Lys Ala Ile Asp Gly Leu Phe Thr Val Phe Ser Ile Thr
945                 950                 955                 960
Thr Leu Arg Asp Trp Thr Pro Asp Pro Gly Ser Ile Ile Cys Trp His
                965                 970                 975
Ala Ser Pro Thr Ala Lys Ala Lys Ala Arg Gln Ala Pro Ile Ser Glu
            980                 985                 990
Val Pro Pro Ser Tyr Gln Gln Ala Gln His Leu Arg Arg Tyr Arg Asp
        995                1000                1005
His Val Ala Arg Gly Leu Asp Met Ser Arg Leu Met Ile Phe Thr
   1010                1015                1020
Trp Asp Leu Pro Gly Arg Cys Asn Ile Arg Ala Met Asn Tyr Ala
   1025                1030                1035
Ile Asn Ala His Leu Arg Arg His Asp Thr Tyr His Ser Trp Phe
   1040                1045                1050
Glu Phe Asp Asn Ala Glu His Ile Val Arg His Thr Ile Ala Asp
   1055                1060                1065
Pro Ala Asp Ile Glu Val Val Gln Ala Glu His Gln Asn Met Thr
   1070                1075                1080
Ser Ala Glu Leu Arg His His Ile Ala Thr Pro Gln Pro Leu Gln
```

```
                        1085                    1090                    1095
Trp Asp Cys Phe Leu Phe Gly Ile Ile Gln Ser Asp Asp His Phe
            1100                    1105                    1110
Thr Phe Tyr Ala Ser Ile Ala His Leu Cys Val Asp Pro Met Ile
            1115                    1120                    1125
Val Gly Val Leu Phe Ile Glu Ile His Met Met Tyr Ser Ala Leu
            1130                    1135                    1140
Val Gly Gly Asp Pro Pro Ile Glu Leu Pro Pro Ala Gly Arg Tyr
            1145                    1150                    1155
Asp Asp His Cys Val Arg Gln Tyr Ala Asp Thr Ala Ala Leu Thr
            1160                    1165                    1170
Leu Asp Ser Ala Arg Val Arg Arg Trp Val Glu Phe Ala Ala Asn
            1175                    1180                    1185
Asn Asp Gly Thr Leu Pro His Phe Pro Leu Pro Leu Gly Asp Leu
            1190                    1195                    1200
Ser Val Pro His Thr Gly Lys Leu Leu Thr Glu Thr Leu Met Asp
            1205                    1210                    1215
Glu Gln Gln Gly Glu Arg Phe Glu Ala Ala Cys Val Ala Ala Gly
            1220                    1225                    1230
Ala Arg Phe Ser Gly Gly Val Phe Ala Cys Ala Ala Leu Ala Glu
            1235                    1240                    1245
Arg Glu Leu Thr Asn Cys Glu Thr Phe Asp Val Val Thr Thr Thr
            1250                    1255                    1260
Asp Thr Arg Arg Thr Pro Thr Glu Leu Arg Thr Thr Gly Trp Phe
            1265                    1270                    1275
Thr Gly Leu Val Pro Ile Thr Val Pro Val Ala Ser Gly Leu Phe
            1280                    1285                    1290
Asp Ser Ala Ala Arg Val Ala Gln Ile Ser Phe Asp Ser Gly Lys
            1295                    1300                    1305
Asp Leu Ala Thr Val Pro Phe Asp Arg Val Leu Glu Leu Ala Arg
            1310                    1315                    1320
Pro Glu Thr Gly Leu Arg Pro Pro Arg Pro Gly Asn Phe Val Met
            1325                    1330                    1335
Ser Phe Leu Asp Ala Ser Ile Ala Pro Leu Ser Thr Val Ala Asn
            1340                    1345                    1350
Ser Asp Leu Asn Phe Arg Ile Tyr Asp Glu Gly Arg Val Ser His
            1355                    1360                    1365
Gln Val Ser Met Trp Val Asn Arg Tyr Gln His Gln Thr Thr Val
            1370                    1375                    1380
Thr Val Leu Phe Pro Asp Asn Pro Ile Ala Ser Glu Ser Val Ala
            1385                    1390                    1395
Asn Tyr Ile Ala Ala Met Lys Ser Ile Tyr Ile Arg Thr Ala Asp
            1400                    1405                    1410
Gly Thr Leu Ala Thr Leu Lys Pro Gly Thr Met Met Gln Phe Tyr
            1415                    1420                    1425
Asp Asp Gly Val Val Gln Leu Asp Arg Ala Ala Leu Thr Leu Arg
            1430                    1435                    1440
Arg Tyr His Phe Pro Ser Gly Thr Ala Lys Val Ile Pro Leu Asp
            1445                    1450                    1455
Gln Ile Arg Gly Tyr Gln Ala Glu Ser Leu Gly Phe Leu Met Ala
            1460                    1465                    1470
Arg Phe Asn Ile Trp Gly Arg Pro Asp Leu Arg Arg Trp Leu Pro
            1475                    1480                    1485
```

-continued

```
Leu Asp Val Tyr Arg Pro Leu Lys Ser Thr Leu Val Thr Leu Asp
    1490                1495                1500

Val Pro Gly Met Arg Pro Lys Pro Ala Cys Thr Pro Thr Arg Pro
1505                1510                1515

Lys Glu Phe Ile Ala Leu Leu Asp Glu Leu Leu Ala Leu His Arg
    1520                1525                1530

Thr Met Ser Leu Leu Asp Ala His Ile Pro Gln Leu Val Ala Ser
    1535                1540                1545

Gln Ser Ala Phe Ala Ala Lys Ala Gly Leu Met Arg His Thr Ile
    1550                1555                1560

Gly Gln Ala Glu Gln Ala Ala Met Ser Ala Gln Ala Phe His Gln
    1565                1570                1575

Gly Glu Ser Ser Ala Ala Phe Gln Ala Ala His Ala Arg Phe Val
    1580                1585                1590

Ala Ala Ala Ala Lys Val Asn Thr Leu Leu Asp Val Ala Gln Ala
    1595                1600                1605

Asn Leu Gly Glu Ala Ala Gly Thr Tyr Val Ala Ala Asp Ala Ala
    1610                1615                1620

Ala Ala Ser Thr Tyr Thr Gly Phe Met Ser Gln Ile Met Tyr Asn
    1625                1630                1635

Tyr Pro Ala Met Leu Gly His Ala Gly Asp Met Ala Gly Tyr Ala
    1640                1645                1650

Gly Thr Leu Gln Ser Leu Gly Ala Glu Ile Ala Val Glu Gln Ala
    1655                1660                1665

Ala Leu Gln Ser Ala Trp Gln Gly Asp Thr Gly Ile Thr Tyr Gln
    1670                1675                1680

Ala Trp Gln Ala Gln Trp Asn Gln Ala Met Glu Asp Leu Val Arg
    1685                1690                1695

Ala Tyr His Ala Met Ser Ser Thr His Glu Ala Asn Thr Met Ala
    1700                1705                1710

Met Met Ala Arg Asp Thr Ala Glu Ala Ala Lys Trp Gly Gly
    1715                1720                1725

<210> SEQ ID NO 26
<211> LENGTH: 541
<212> TYPE: PRT
<213> ORGANISM: Mycobacterium tuberculosis

<400> SEQUENCE: 26

Phe Ser Arg Pro Gly Leu Pro Val Glu Tyr Leu Gln Val Pro Ser
1               5                   10                  15

Ser Met Gly Arg Asp Ile Lys Val Gln Phe Gln Ser Gly Asn Asn
                20                  25                  30

Ser Pro Ala Val Tyr Leu Leu Asp Gly Leu Arg Ala Gln Asp Tyr
        35                  40                  45

Asn Gly Trp Asp Ile Asn Thr Pro Ala Phe Glu Trp Tyr Tyr Gln Ser
    50                  55                  60

Gly Leu Ser Ile Val Met Pro Val Gly Gly Gln Ser Ser Phe Tyr Ser
65                  70                  75                  80

Asp Trp Tyr Ser Pro Ala Cys Gly Lys Ala Gly Cys Gln Thr Tyr Lys
                85                  90                  95

Trp Glu Thr Phe Leu Thr Ser Glu Leu Pro Gln Trp Leu Ser Ala Asn
                100                 105                 110

Arg Ala Val Lys Pro Thr Gly Ser Ala Ala Ile Gly Leu Ser Met Ala
```

```
                115                 120                 125
        Gly Ser Ser Ala Met Ile Leu Ala Ala Tyr His Pro Gln Gln Phe Ile
            130                 135                 140

Tyr Ala Gly Ser Leu Ser Ala Leu Leu Asp Pro Ser Gln Gly Met Gly
        145                 150                 155                 160

Pro Ser Leu Ile Gly Leu Ala Met Gly Asp Ala Gly Tyr Lys Ala
                        165                 170                 175

Ala Asp Met Trp Gly Pro Ser Ser Asp Pro Ala Trp Glu Arg Asn Asp
                    180                 185                 190

Pro Thr Gln Gln Ile Pro Lys Leu Val Ala Asn Asn Thr Arg Leu Trp
                    195                 200                 205

Val Tyr Cys Gly Asn Gly Thr Pro Asn Glu Leu Gly Gly Ala Asn Ile
                210                 215                 220

Pro Ala Glu Phe Leu Glu Asn Phe Val Arg Ser Ser Asn Leu Lys Phe
        225                 230                 235                 240

Gln Asp Ala Tyr Asn Ala Ala Gly Gly His Asn Ala Val Phe Asn Phe
                        245                 250                 255

Pro Pro Asn Gly Thr His Ser Trp Glu Tyr Trp Gly Ala Gln Leu Asn
                    260                 265                 270

Ala Met Lys Gly Asp Leu Gln Ser Ser Leu Gly Ala Gly Thr Glu Gln
                275                 280                 285

Gln Trp Asn Phe Ala Gly Ile Glu Ala Ala Ser Ala Ile Gln Gly
                290                 295                 300

Asn Val Thr Ser Ile His Ser Leu Leu Asp Glu Gly Lys Gln Ser Leu
        305                 310                 315                 320

Thr Lys Leu Ala Ala Ala Trp Gly Gly Ser Gly Ser Glu Ala Tyr Gln
                        325                 330                 335

Gly Val Gln Gln Lys Trp Asp Ala Thr Ala Thr Glu Leu Asn Asn Ala
                    340                 345                 350

Leu Gln Asn Leu Ala Arg Thr Ile Ser Glu Ala Gly Gln Ala Met Ala
                    355                 360                 365

Ser Thr Glu Gly Asn Val Thr Gly Met Phe Ala Thr Val Thr Asp Asp
                370                 375                 380

Tyr Leu Ala Asn Asn Val Asp Tyr Ala Ser Gly Phe Lys Gly Pro Leu
        385                 390                 395                 400

Pro Met Pro Pro Ser Lys His Ile Ala Ile Val Ala Cys Met Asp Ala
                        405                 410                 415

Arg Leu Asp Val Tyr Arg Met Leu Gly Ile Lys Glu Gly Glu Ala His
                    420                 425                 430

Val Ile Arg Asn Ala Gly Cys Val Val Thr Asp Val Ile Arg Ser
                435                 440                 445

Leu Ala Ile Ser Gln Arg Leu Leu Gly Thr Arg Glu Ile Ile Leu Leu
                450                 455                 460

His His Thr Asp Cys Gly Met Leu Thr Phe Thr Asp Asp Phe Lys
        465                 470                 475                 480

Arg Ala Ile Gln Asp Glu Thr Gly Ile Arg Pro Thr Trp Ser Pro Glu
                        485                 490                 495

Ser Tyr Pro Asp Ala Val Glu Asp Val Arg Gln Ser Leu Arg Arg Ile
                    500                 505                 510
```

```
Glu Val Asn Pro Phe Val Thr Lys His Thr Ser Leu Arg Gly Phe Val
        515                 520                 525

Phe Asp Val Ala Thr Gly Lys Leu Asn Glu Val Thr Pro
        530                 535                 540
```

M. TUBERCULOSIS VACCINES

FIELD OF INVENTION

The present invention discloses new immunogenic compositions based on Esx-1 associated and esx family polypeptides derived from *M. tuberculosis*

GENERAL BACKGROUND

Immunity to *M. tuberculosis* is characterized by some basic features; specifically sensitized T lymphocytes mediates protection, and the most important mediator molecule seems to be interferon gamma (IFN-γ).

*M. tuberculosis* holds, as well as secretes, several proteins of potential relevance for the generation of a new TB vaccine. In 1998 Cole et al. published the complete genome sequence of *M. tuberculosis* and predicted the presence of approximately 4000 open reading frames[1]. However importantly, this sequence information cannot be used to predict if the DNA is translated and expressed as proteins in vivo. The genome sequence has been used extensively to design DNA arrays for RNA expression analysis and in proteome studies to identify expressed proteins. Even with the vaste amount of expression data and the significant improvement of in silico prediction tools it is still not possible to predictic with certainty that a given sequence will encode an immunogenic molecule. The only way to determine if a molecule is recognized by the immune system during or after an infection with *M. tuberculosis* is to produce the given molecule and test it in an appropriate assay as described herein.

Currently there are several new TB vaccines in clinical trials. However, they are primarily classical preventive vaccines based on a limited number of antigens expressed in the early stage of infection. As a direct consequence of the expression dynamic the epitope pattern that is presented to T cells changes radically over time—implicating how new vaccines should be designed. E.g. for the transiently expressed early antigen, Ag85B, two independent T cell transfer studies have shown that 3-4 weeks after infection, Ag85B is no longer being presented to T cells and as a result there is no Ag85B specific production of cytokine's, chemokine's etc. at this or later time points of the infection[2,3]. Thus, it is of limited value for a chronic disease that establish long-term co-existence with the host to vaccinate and induce memory T cells specific for epitopes in proteins that are only expressed during a brief period of the infection.

For vaccine development it is therefore vital to identify antigens that are highly expressed in the later stage of infection and among these select those that are immunogenic and can contribute to protection and include this special subset of proteins in TB vaccines. By doing so it is not only possible to improve vaccine potency and epitope coverage but also target latent infections.

Mycobacteria secretion systems are responsible for the export of proteins into the extracellular environment. *Mycobacterium tuberculosis* has several different types of secretion systems of which the ESX secretion system (type VII) is relevant for this invention. *Mycobacterium tuberculosis* has five of these systems, termed ESX-1 to ESX-5. The 6-kDa early secretory antigenic target of *Mycobacterium tuberculosis* (ESAT-6) and the 10-kDa culture filtrate antigen (CFP-10), are proteins secreted by the ESAT-6 secretion system 1 (ESX-1) and are among the most immunodominant *M. tuberculosis* (MTB) antigens. These attributes makes them important for tuberculosis (TB) vaccine development. Based upon this knowledge we tested other ESX-1 associated proteins as potential TB vaccine antigens.

SUMMARY OF THE INVENTION

The invention is related to preventing and treating infections caused by species of the tuberculosis complex (*M. tuberculosis, M. bovis, M. africanum, M. microti, M. canettii, M. pinnipedii, Mycobacterium mungi*) by the use of a fusion protein or antigen cocktail comprising *M. tuberculosis* antigens selected from ESX-1 associated and esx family polypeptides possibly including latency polypeptides. The fusion proteins or antigen cocktails are used in vaccines preferably together with an adjuvant and/or an immunemodulator.

DETAILED DISCLOSURE OF THE INVENTION

The invention discloses a fusion protein or antigen cocktail, which comprises the amino acid sequence selected from
(a) SEQ ID NO.1 (ESAT6), SEQ ID NO 2 (Rv3614c), SEQ ID NO 3 (Rv3615c), SEQ ID NO 4 (Rv3865), SEQ ID NO 5 (Rv3849) and SEQ ID NO 6 (Rv3872), or
(b) SEQ ID NO 2 (Rv3614c), SEQ ID NO 3 (Rv3615c), SEQ ID NO 4 (Rv3865), SEQ ID NO 5 (Rv3849) and SEQ ID NO 6 (Rv3872) or
(c) SEQ ID NO 2 (Rv3614c), SEQ ID NO 3 (Rv3615c), SEQ ID NO 4 (Rv3865), SEQ ID NO 5 (Rv3849), SEQ ID NO 6 (Rv3872) and SEQ ID NO 7 (Rv3616), or
(d) SEQ ID NO 2 (Rv3614c), SEQ ID NO 3 (Rv3615c), SEQ ID NO 4 (Rv3865), SEQ ID NO 5 (Rv3849), SEQ ID NO 6 (Rv3872) SEQ ID NO 7 (Rv3616) and SEQ ID NO 8 (Rv3881c), or
(e) SEQ ID NO 2 (Rv3614c), SEQ ID NO 3 (Rv3615c), SEQ ID NO 4 (Rv3865), SEQ ID NO 5 (Rv3849), SEQ ID NO 6 (Rv3872) and SEQ ID NO 8 (Rv3881c), or
(f) SEQ ID NO 9 (Rv3891c), SEQ ID NO 10 (Rv3890), SEQ ID NO 11 (Rv0287), SEQ ID NO 12 (Rv0288), SEQ ID NO 13 (Rv3620c) and SEQ ID NO 14 (Rv3619), or
(g) SEQ ID NO 11 (Rv0287), SEQ ID NO 12 (Rv0288), SEQ ID NO 13 (Rv3620c), SEQ ID NO 14 (Rv3619), NO 7 (Rv3616c) and SEQ ID NO 3 (Rv3615c) or
(h) SEQ ID NO 11 (Rv0287), SEQ ID NO 12 (Rv0288), SEQ ID NO 13 (Rv3620c), SEQ ID NO 14 (Rv3619), NO 7 (Rv3616c), SEQ ID NO 3 (Rv3615c) and SEQ ID 9 (Rv3881c), or
(i) SEQ ID NO 1 (ESAT6), SEQ ID NO 15 (Ag85B) and SEQ ID NO 16 (Rv1284), or
(j) an amino acid sequence analogue having at least 80% sequence identity to any-one of the sequences in (a)-(i) and at the same time being immunogenic;

The cysteines in the fusion protein according to the invention have preferably been replaced by another amino acid to avoid sulhur-bridge formation and protein aggregation. A preferred replacement amino acid is serine.

The fusion partners of the fusion protein according to the invention is preferably linked with a linker molecule to allow for protein folding and dimer formation.

Preferred fusion proteins according to the invention are suggested as SEQ ID NO 18 (H64), SEQ ID NO 19 (H68), SEQ ID NO 20 (H69), SEQ ID NO 21 (H70), SEQ ID NO 22 (H71), SEQ ID NO 23 (H65), SEQ ID NO 24 (H72), SEQ ID NO 25 (H73) or SEQ ID NO 26 (H67).

Another embodiment of the invention is using an antigen cocktail according to the invention e.g. the above mentioned amino acid sequences (a)-(i) (comprising SEQ ID NO 1, 2, 3, 4, 5, 6, 7, 8, 9, 10, 11, 12, 13, 14, 15 and 16) without fusing the polypeptides together.

A preferred antigen cocktail comprises SEQ ID NO 16 and H1 (SEQ ID NO 17) where H1 is a fusion between SEQ ID NO 1 and SEQ ID NO 15.

In a still further embodiment, the invention discloses an immunogenic composition or pharmaceutical composition comprising a fusion protein or antigen cocktail as defined above, preferably in the form of a vaccine.

In another embodiment, the invention discloses a method for immunising an animal, including a human being, against tuberculosis caused by virulent mycobacteria, e.g. by *Mycobacterium tuberculosis, Mycobacterium africanum, Mycobacterium bovis M. microti, M. canettii, M. pinnipedii* or *Mycobacterium mungi*, comprising administering to the animal the polypeptide as defined above, the immunogenic composition according to the invention, or the vaccine according to the invention.

The vaccine, immunogenic composition and pharmaceutical composition according to the invention can be used prophylactically in a subject not infected with a virulent *mycobacterium* or therapeutically in a subject already infected with a virulent *mycobacterium*.

Definitions

Polypeptides

The word "polypeptide" in the present invention should have its usual meaning. That is an amino acid chain of any length, including a full-length protein, oligopeptides, short peptides and fragments thereof, wherein the amino acid residues are linked by covalent peptide bonds.

The polypeptide may be chemically modified by being glycosylated, by being lipidated (e.g. by chemical lipidation with palmitoyloxy succinimide as described by Mowat et al. 1991 or with dodecanoyl chloride as described by Lustig et al. 1976), by comprising prosthetic groups, or by containing additional amino acids such as e.g. a purification tag (e.g. his-tag) or a signal peptide. Purification tag's are used to obtain highly pure protein preparations and for e.g the His-tag comprises a methionine as the first amino acid followed by 6-8 histidines if used N-terminal, and 6-8 histidines followed by a STOP-codon if used C-terminal. When used N-terminal the methionine start codon in the gene coding for the polypeptide fusion can be deleted to avoid false translational start sites. The same is true if the gene contains one of the alternative start codons GUG or UUG which normally codes for valine and leucine, respectively, but, as a start codon, they are translated as methionine or formylmethionine.

Each polypeptide is encoded by a specific nucleic acid sequence. It will be understood that such sequences include analogues and variants hereof wherein such nucleic acid sequences have been modified by substitution, insertion, addition or deletion of one or more nucleic acid. Substitutions are preferably silent substitutions in the codon usage which will not lead to any change in the amino acid sequence, but may be introduced to enhance the expression of the protein.

Secretion Systems

Type VII secretion system (T7SS) is a recent discovery in bacterial secretion systems that was first identified in *Mycobacterium tuberculosis*. The corresponding gene clusters were referred to as the ESX (ESAT-6 Secretion System) regions[4-6]. The genome of *M. tuberculosis* H37Rv contains five gene clusters that have evolved through gene duplication events and include components of the T7SS secretion machinery. These clusters are called ESAT-6 secretion system (ESX) 1 through 5. The ESX systems have been shown to secrete proteins lacking classical signal peptides. Furthermore, most of the proteins secreted by ESX1-5 follow a pairwise dependency for secretion[7].

Esx-Family

Except for Rv3017c (esxR) the genes encoding the ESAT-6 family proteins are arranged in tandem pairs at 11 loci on the *M. tuberculosis* H37Rv chromosome and are often preceded by a pe-ppe gene pair. They encode proteins that are approximately 100 amino acids in length and are secreted by the ESX1-5 systems Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

An immunogenic polypeptide is defined as a polypeptide that induces an immune response in a biological sample or an individual currently or previously infected with a virulent *mycobacterium*.

The immune response may be monitored by one of the following methods:

An in vitro cellular response is determined by release of a relevant cytokine such as IFN-γ, from lymphocytes withdrawn from an animal or human being currently or previously infected with virulent mycobacteria, or by detection of proliferation of these T cells. The induction being performed by the addition of the polypeptide or the immunogenic portion to a suspension comprising from $1 \times 10^5$ cells to $3 \times 10^5$ cells per well. The cells being isolated from either the blood, the spleen, the liver or the lung and the addition of the polypeptide or the immunogenic portion resulting in a concentration of not more than 20 μg per ml suspension and the stimulation being performed from two to five days. For monitoring cell proliferation the cells are pulsed with radioactive labeled Thymidine and after 16-22 hours of incubation detecting the proliferation by liquid scintillation counting. A positive response being a response more than background plus two standard deviations. The release of IFN-γ can be determined by the ELISA method, which is well known to a person skilled in the art. A positive response being a response more than background plus two standard deviations. Other cytokines than IFN-γ could be relevant when monitoring the immunological response to the polypeptide, such as IL-12, TNF-α, IL-4, IL-5, IL-10, IL-6, TGF-β. Another and more sensitive method for determining the presence of a cytokine (e.g. IFN-γ) is the ELISPOT method where the cells isolated from either the blood, the spleen, the liver or the lung are diluted to a concentration of preferable of 1 to $4 \times 10^6$ cells/ml and incubated for 18-22 hrs in the presence of of the polypeptide or the immunogenic portion resulting in a concentration of not more than 20 μg per ml. The cell suspensions are hereafter diluted to 1 to $2 \times 10^6$/ml and transferred to Maxisorp plates coated with anti-IFN-γ and incubated for preferably 4 to 16 hours. The IFN-γ producing cells are determined by the use of labelled secondary anti-IFN-γ antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or an *M. tuberculosis* infected person where the T cell lines have been driven with either live mycobacteria, extracts from the bacterial cell or culture filtrate for 10 to 20 days with the addition of IL-2. The induction being performed by addition of not more than 20 μg polypeptide per ml suspension to the T cell lines containing from $1\times10^5$ cells to $3\times10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both assays a positive response being a response more than background plus two standard deviations.

An in vivo cellular response which may be determined as a positive DTH response after intradermal injection or local application patch of at most 100 μg of the polypeptide or the immunogenic portion to an individual who is clinically or subclinically infected with a virulent *Mycobacterium*, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the OD e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of a virulent *Mycobacterium*. Readout for induced protection could be decrease of the bacterial load in target organs compared to non-vaccinated animals, prolonged survival times compared to non-vaccinated animals and diminished weight loss compared to non-vaccinated animals.

Immunogenic Portion

In a preferred embodiment of the invention, the polypeptide comprises an immunogenic portion of the polypeptide, such as an epitope for a B-cell or T-cell. The immunogenic portion of a polypeptide is a part of the polypeptide, which elicits an immune response in an animal or a human being, and/or in a biological sample determined by any of the biological assays described herein. The immunogenic portion of a polypeptide may be a T-cell epitope or a B-cell epitope. Immunogenic portions can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence (Ravn et al 1999).

In order to identify relevant T-cell epitopes which are recognised during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-γ assay described herein. Another method utilises overlapping oligopeptides for the detection of MHC class II epitopes, preferably synthetic, having a length of e.g. 20 amino acid residues derived from the polypeptide. These peptides can be tested in biological assays (e.g. the IFN-γ assay as described herein) and some of these will give a positive response (and thereby be immunogenic) as evidence for the presence of a T cell epitope in the peptide. For the detection of MHC class I epitopes it is possible to predict peptides that will bind (Stryhn et al. 1996) and hereafter produce these peptides synthetic and test them in relevant biological assays e.g. the IFN-γ assay as described herein. The peptides preferably having a length of e.g. 8 to 11 amino acid residues derived from the polypeptide. B-cell epitopes can be determined by analysing the B cell recognition to overlapping peptides covering the polypeptide of interest as e.g. described in Harboe et al 1998.

Although the minimum length of a T-cell epitope has been shown to be at least 6 amino acids, it is normal that such epitopes are constituted of longer stretches of amino acids. Immunogenic portions of polypeptides may be recognised by a broad part (high frequency) or by a minor part (low frequency) of the genetically heterogenic human population. In addition some immunogenic portions induce high immunological responses (dominant), whereas others induce lower, but still significant, responses (subdominant). High frequency><low frequency can be related to the immunogenic portion binding to widely distributed MHC molecules (HLA type) or even by multiple MHC molecules (Kilgus et al. 1991, Sinigaglia et al 1988).

In the context of providing candidate molecules for a new vaccine against tuberculosis, the subdominat epitopes are however as relevant as are the dominant epitopes since it has been show (WO2008000261) that such epitopes can induce protection regardless of being subdominant.

A common feature of the polypeptides of the invention is their capability to induce an immunological response as illustrated in the examples. It is understood that a variant of a polypeptide of the invention produced by substitution, insertion, addition or deletion is also immunogenic determined by any of the assays described herein.

Fusion Proteins

By the term "fusion protein" is understood a random order of two or more immunogenic polypeptides from *M. tuberculosis* or analogues thereof fused together with or without an amino acid linker/spacer(s) of arbitrary length and sequence. To avoid protein aggregation in the down-stream production all cysteines in the fusion protein can be replaced with any amino acid but serine is the preferred substitute because of its high structural similarity with cysteine Linkers Linkers or spacers are short peptide sequences that occur between polypeptide partners in a fusion protein. Linkers are often composed of flexible residues like glycine and serine so that the adjacent protein domains are free to move relative to one another and for independent proper folding during secretion/manufacturing. Longer linkers are used when it is necessary to ensure that two adjacent domains do not sterically interfere with one another.

Paralogue, Ortologue and Homologue

By the term "paralogue" is understood proteins or genes that share some degree of homology because of shared ancestry followed by one or more duplication event(s). Paralogues are genes related by duplication within a genome while orthologs, which are homologous genes in different species that evolved from a common ancestral gene by speciation, The term, homologue apply to the relationship between genes separated by the event of speciation (ortholog) or to the relationship between genes separated by the event of genetic duplication (paralog).

Analogue

By the term sequence analogue is meant polypeptides which are structurally and immunogenically similar to each other but differs in amino acid composition Vaccine Another part of the invention pertains to a vaccine composition comprising a fusion protein according to the invention. An effective vaccine, wherein a fusion protein the invention is recognized by the animal, will in an animal model be able to decrease bacterial load in target organs, prolong survival times and/or diminish weight loss after challenge with a virulent *Mycobacterium*, compared to non-vaccinated animals In order to ensure optimum performance of such a vaccine composition it is preferred that it comprises an immunologically and pharmaceutically acceptable carrier, vehicle or adjuvant.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of cationic liposomes (e.g. dimethyldioctadecylammonium bromide (DDA)), Quil A, poly I:C, aluminium hydroxide, Freund's incomplete adjuvant, IFN-γ, IL-2, IL-12, monophosphoryl lipid A (MPL), Trehalose Dimycolate (TDM), Trehalose Dibehenate (TDB), Muramyl Dipeptide (MDP) and monomycolyl glycerol (MMG) or combinations hereof.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-γ inducers such as poly I:C in combination with the above-mentioned adjuvants.

Another interesting possibility for achieving adjuvant effect is to employ the technique described in Gosselin et al., 1992 (which is hereby incorporated by reference herein). In brief, a relevant antigen such as an antigen of the present invention can be conjugated to an antibody (or antigen binding antibody fragment) against the Fcγ receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 µg to 1000 µg, such as in the range from about 1 µg to 300 µg, and especially in the range from about 10 µg to 50 µg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

In many instances, it will be necessary to have multiple administrations of the vaccine. Especially, vaccines can be administered to prevent an infection with virulent mycobacteria and/or to treat established mycobacterial infection. When administered to prevent an infection, the vaccine is given prophylactically, before definitive clinical signs or symptoms of an infection are present.

The invention also pertains to a method for immunising an animal, including a human being, against TB caused by virulent mycobacteria, comprising administering to the animal the polypeptide of the invention, or a vaccine composition of the invention as described above, or a living vaccine described above.

Therapeutic Vaccine.

The invention also relates to the use of a fusion protein of the invention for use as therapeutic vaccines based on their ability to diminish the severity of *M. tuberculosis* infection in experimental animals or prevent reactivation of previous infection, when administered as a vaccine. The composition used for therapeutic vaccines can be prepared as described above for vaccines.

H64, H68, H69, H70 and H71: Fusion Proteins Comprising ESX-1 Associated Polypeptides Mycobacteria secretion systems are responsible for the export of virulence factors either to extracellular environment or directly into the host cell and thus, play a vital role in the virulence and survival of the bacteria. Part of the ESX-1 secretion system was identified during the comparative genomic analysis of attenuated *M. bovis* BCG and pathogenic mycobacterial species[8]. One of the main genome differences was a major deletion in the *M. bovis* genome that included the region encoding the secreted antigens CFP10 and ESAT-6. This region was observed to be especially responsible for virulence and restoration of the region not only enabled the secretion of ESAT-6, but also led to increased virulence in *M. bovis* BCG[4].

The ESX-1 secretion system is conserved among slow growing mycobacteria including all pathogenic mycobacteria within the *M. tuberculosis* complex and is required for survival of mycobacteria in vivo. The functions of the secreted effector molecules are required for initiation of granuloma formation and phagosome maturation, essential for escape from phagosomes, cell lysis and cell-to-cell spreading, apoptosis through caspase activation and immune modulation by interfering with TLR2 signaling[6,9].

Today we know that the ESX-1 secretion system is encoded by three different loci, the ESX-1 locus, the espA operon and the locus for the transcriptional regulator EspR[10,11]. The exact number of components that are involved in ESX-1 secretion is still debated and seems to vary between different mycobacterial species. Currently the following *Mycobacterium tuberculosis* genes have shown relation to the ESX-1 system: espR, espA; espB; espC espD, espF esxA; esxB; mycP1; PE35; Rv3862 (WhiB6), Rv3866, Rv3868; Rv3869; Rv3870; Rv3871; Rv3876; Rv3877; Rv3879c; Rv3881c Rv3882c and the MCE1 proteins Mce1B, Mce1C MCe1F and Rv0177[12,13].

The six experimentally verified ESX-1 substrates, Rv3616c (EspA), Rv3615c (EspC), Rv3849 (EspR), ESAT-6, CFP-10 and Rv3881c (EspB) are mutually dependent on each other for secretion[7].

All known ESX-1 secreted substrates are strong antigens that are highly expressed in different stages of infection—in contrast to eg. Ag85 and other metabolic related antigens that are downregulated shortly after infection.

Given the high expression at various time point during infection and the high immunogenicity of many ESX-1 associated proteins we made the H64 backbone fusion protein based on six of the ESX-1 associated proteins and from this backbone the H68, H69, H70 and H71 fusion proteins were made.

The H64 fusion protein consist of three experimentally proven ESX-1 substrates (ESAT-6, EspR, EspC) plus three secreted proteins associated with ESX-1 (EspD, PE35 and EspF). The order of proteins in the H64 fusion is: ESAT-6, EspD, EspC, EspF, EspR, PE35 but any other order can be used. H64 consists of 716 amino acids, the theoretical molecular weight is 75698 g/mol and the isoelectric point 4,56. In the wild type sequence encoded from the *Mycobacterium tuberculosis* chromosome there is one cysteine in EspD, EspC and EspR. To avoid problems with sulphurbridge formation and protein aggregation during refolding all three cysteines have been replaced with the amino acid serine.

Info on the individual proteins in H64:

ESAT-6 (Rv3875) is, together with CFP10, secreted via ESX-1 as a heterologous dimer[14].

EspR (Rv3849) is a transcriptional activator of its own expression and an operon that includes EspA (Rv3616c), C and D. The EspR protein is secreted via ESX-1[15].

EspC (Rv3615c) gene expression is regulated by EspR. EspC is secreted by ESX-1[11].

EspD (Rv3614c) gene expression is regulated by EspR. EspD is co-transcribed with espC. EspD expression but not secretion is required for EsxA secretion. EspD stabilizes the EspA-EspC complex. EspD secretion does not exclusively require the ESX-1 system[16].

PE35 (Rv3872) is a secreted PE protein. Inactivation of gene pe35 (Rv3872) impaired expression of CFP-10 and ESAT-6, suggesting a role in regulation.

EspF (Rv3865) is a secreted protein. The amino acid sequence of EspF is 36% identical to EspC. Inactivation of EspF protein leads to attenuation of mycobacteria confirming its importance for survival. The attenuation of *M. tuberculosis* EspF mutants is not caused by the lack of ESAT-6 secretion but, rather, by the interruption of another, yet-unknown function of the ESX-1 system[17].

The H68 fusion protein comprises the same proteins as H64 except that ESAT-6 is omiited in this constructs due to its importance in the diagnosis of tuberculosis: Rv3614c-Rv3615c-Rv3865-Rv3849-PE35

The H69 fusion protein comprises the same proteins as H68 but with the addition of EspC (Rv3616c): Rv3614c-Rv3615c-Rv3616c-Rv3865-Rv3849-PE35

Info on the additional protein in H69

EspC (Rv3616c) gene expression is regulated by EspR. EspC is secreted by ESX-1[11].

The H70 fusion protein comprises the same proteins as H69 but with the addition of EspB (Rv3881c): Rv3881c-Rv3614c-Rv3615c-Rv3616c-Rv3865-Rv3849-PE35.

Info on the additional protein in H70

EspB (Rv3881c) is secreted by the ESX-1 secretion system. During the secretion process it is cleaved by the membrane anchored proteinase MycP1[18].

The H71 fusion protein comprises the same proteins as H68 but with the addition of EspB (Rv3881c): Rv3881-Rv3614-Rv3615-Rv3865-Rv3849-PE35.

H65, H72 and H73: A Fusion Protein Comprising ESAT-6 Family Polypeptides

Several secreted proteins from mycobacteria have been shown to induce strong cellular immune responses[18]. Two of the most frequently recognized T cell antigens from *M. tuberculosis* are the small secreted proteins ESAT-6 (early secretory antigenic target of 6 kDa) and CFP-10 (culture filtrate protein of 10 kDa), the prototypes of the Esx family[19]. Genes encoding ESAT-6 and CFP-10 are located directly adjacent to each other and cotranscribed[20]. Analysis of the *M. tuberculosis* H37Rv genome sequence revealed 11 pairs of tandem genes encoding paralogous ESAT-6 family proteins[1].

The ESAT-6 (esx) family has 23 members (11 gene pairs and a singleton, Rv0287, Rv0288, Rv1037c, Rv1038c, Rv1197, Rv1198, Rv1792, Rv1793, Rv2346c, Rv2347c, Rv3017c, Rv3019c, Rv3020c, Rv3444c, Rv3445c, Rv3619c, Rv3620c, Rv3874, Rv3875, Rv3890c, Rv3891c, Rv3904c and Rv3905c). The sequence identity varies between the Esx proteins from 35% to 98% but all of them belong to the WXG100 family, characterized by a size of ~100 amino acids and the presence of a Trp-Xaa-Gly (W-X-G) motif[21]. Thus, far the precise biological function of the ESAT-6 family members are unknown but they are virulence factors.

ESAT-6 and CFP10 interact to form a 1:1 heterodimer, that is essential for their secretion via the ESX-1 secretion system[22]. Proteins encoded by two other paralogous gene pairs, EsxR-EsxS and EsxH-EsxG, also form 1:1 complexes, suggesting that this may be typical of all Esx protein couplets[23,24].

The EsxH-EsxG complex is secreted by ESX-3. They are essential for in vitro growth, involved in iron/zinc homeostasis[25,26] and regulated by the iron-dependent transcriptional repressor IdeR and the zinc-uptake regulator Zur[27,28].

ESX-5 is known to be necessary for the secretion of PE and PPE proteins in *Mycobacterium marinum* and for macrophage subversion[29,30]. Most likely it is also responsisble for the secretion of the five ESAT-6 paralogues esx1 (rv1037c), esxL (rv1198), esxO, (rv2346c), esxV (rv3619c) and the five CFP10 paralogues esxJ (rv1038c), esxK (rv1197), esxP (rv2347c), esxW, (rv3620c). In *M. marinum* the function of ESX-5 mediated protein secretion is to establish a moderate and persistent infection[31]. ESX-5 deficient *Mycobacterium marinum* is hypervirulent, ESX-5 is also found in *M. tuberculosis*.

The functions of ESX-2 and ESX-4 remain unknown but based on functional and physical homology to the other ESX secretion systems they are likety to secrete the esxC-esxD and esxT-esxU complexes, respectively.

Because the ESAT-6 family proteins are highly expressed during an *Mycobacterium tuberculosis* infection, are highly immunogenic and experimental data support their protective efficacy following vaccination[32,33], we constructed the H65 fusion protein based on six ESAT-6 family proteins. To make the vaccine compatible with the current diagnostic test the most prominent family members—ESAT-6 and CFP10—where not included.

The order of the ESAT-6 proteins in the H65 fusion is: Rv3891c-Rv3890c-Rv0287-Rv0288-Rv3620c-Rv3619c, but any order can be used. Between each of the 3 protein couples the 9 amino acid GLVPRGSTG linker sequence is inserted to allow for protein-folding and dimer-formation. Between Rv3890c and Rv0287 the 20 amino acid LIGAHPRALNWKFGGAAFL linker is inserted and between Rv0288 and Rv3630c the 20 amino acid LGFGAGRLRGLFTNPGSWRI linker. The sequences of both 20 amino acid linkers are from the Rv1886 *M. tuberlosis* HRv37 protein sequence and corresponds to amino acid postions 61-80 and 161-180 in this protein[34]. The linkers were included becaused they have been shown to be human epitopes and because T cells responding to these secrete large amounts of cytokine IL-2. IL-2 is necessary for the growth, proliferation, and differentiation of T cells to become effector T cells. In addition to increase the diversity of the vaccine induced T cell pool these IL-2 secreting T cells may provide cytokine help to other T cells in their differentiation from naïve to effector T cells.

The order of the ESAT-6 proteins in the H72 fusion is: Rv3616c-Rv3615c-Rv3620c-Rv3619c-Rv0287-Rv0288-, but any order can be used.

The order of the ESAT-6 proteins in the H73 fusion is: Rv3881c-Rv3616c-Rv3615c-Rv3620c-Rv3619c-Rv0287-Rv0288-, but any order can be used.

H67: A Fusion Protein Comprising a Latency Polypeptide Ag85B-ESAT6-Rv1284

The H1 vaccine, a protein fusion of Ag85B and ESAT-6 (Ag85B-ESAT6), is a very efficient vaccine against a primary infection but due to the expression profile of the two antigens it has its primary effect during the earlier stages of infection. To develop a vaccine that is effective in both early and late stage infection (persistence and reactivation from latency) the H1 fusion protein was enriched with Rv1284. Expression studies have shown that Rv1284 is strongly expressed under in vitro conditions simulating late stage infection. It should therefore be possible not only to increase the protective efficacy of H1 in the early infection stages but also extending the efficacy to the later stages of infection by the addition of Rv1284.

We designed the H67 fusion protein based on Ag85B, ESAT-6 and R1284 which reflects the order of the proteins, but any order of the polypeptides may be used. H67 consists of 549 amino acids, the theoretical molecular weight is 59548 g/mol and the isoelectric point 5,36. In the wild type sequence encoded from the *M. tuberculosis* chromosome there are three cysteines in Ag85B, and three cysteines in Rv1284. To avoid problems with sulphurbridge formation and protein aggregation during refolding all three cysteines have been replaced with the amino acid serine.

Info on the individual proteins in H67:

Aq85B (Rv1886c) is mycolyl transferase 85B, an extracellular protein, and is selected as the most immunogenic protein in the fusion protein characterized by an an initial transient increase in Ag85B expression but already after 10 days infection the level of bacterial Ag85B expression had dropped approx. 15 times per CFU and this low level is maintained at least up to 100 days post infection[35].

ESAT-6 (Rv3875) is, together with CFP10, secreted via ESX-1 as a heterologous dimer. The ESX-1 substrate ESAT-6 shows high expression at various time point during infection and display high immunogenicity.

Rv1284 is encoding a beta-carbonic anhydrase, and the gene has been shown to be essential for *M. tuberculosis*. The expression of the gene has previously been reported to be 14- to 40-fold increased in nutrient-starved cultures[36]

| SEQ ID NO | Amino acid sequence |
|---|---|
| 1 | MTEQQWNFAG IEAAASAIQG NVTSIHSLLD EGKQSLTKLA AAWGGSGSEA YQGVQQKWDA TATELNNALQ NLARTISEAG QAMASTEGNV TGMFA |
| 2 | VDLPGNDFDS NDFDAVDLWG ADGAEGWTAD PIIGVGSAAT PDTGPDLDNA HGQAETDTEQ EIALFTVTNP PRTVSVSTLM DGRIDHVELS ARVAWMSESQ LASEILVIAD LARQKAQSAQ YAFILDRMSQ QVDADEHRVA LLRKTVGETW GLPSPEEAAA AEAEVFATRY SDDCPAPDDE SDPW |
| 3 | MTENLTVQPE RLGVLASHHD NAAVDASSGV EAAAGLGESV AITHGPYCSQ FNDTLNVYLT AHNALGSSLH TAGVDLAKSL RIAAKIYSEA DEAWRKAIDG LFT |
| 4 | MTGFLGVVPS FLKVLAGMHN EIVGDIKRAT DTVAGISGRV QLTHGSFTSK FNDTLQEFET TRSSTGTGLQ GVTSGLANNL LAAAGAYLKA DDGLAGVIDK IFG |
| 5 | MSTTFAARLN RLFDTVYPPG RGPHTSAEVI AALKAEGITM SAPYLSQLRS GNRTNPSGAT MAALANFFRI KAAYFTDDEY YEKLDKELQW LCTMRDDGVR RIAQRAHGLP SAAQQKVLDR IDELRRAEGI DA |
| 6 | MEKMSHDPIA ADIGTQVSDN ALHGVTAGST ALTSVTGLVP AGADEVSAQA ATAFTSEGIQ LLASNASAQD QLHRAGEAVQ DVARTYSQID DGAAGVFAE |
| 7 | MSRAFIIDPT ISAIDGLYDL LGIGIPNQGG ILYSSLEYFE KALEELAAAF PGDGWLGSAA DKYAGKNRNH VNFFQELADL DRQLISLIHD QANAVQTTRD ILEGAKKGLE FVRPVAVDLT YIPVVGHALS AAFQAPFCAG AMAVVGGALA YLVVKTLINA TQLLKLLAKL AELVAAAIAD IISDVADIIK GTLGEVWEFI TNALNGLKEL WDKLTGWVTG LFSRGWSNLE SFFAGVPGLT GATSGLSQVT GLFGAAGLSA SSGLAHADSL ASSASLPALA GIGGGSGFGG LPSLAQVHAA STRQALRPRA DGPVGAAAEQ VGGQSQLVSA QGSQGMGGPV GMGGMHPSSG ASKGTTTKKY SEGAAAGTED AERAPVEADA GGGQKVLVRN VV |
| 8 | MTQSQTVTVD QQEILNRANE VEAPMADPPT DVPITPCELT AAKNAAQQLV LSADNMREYL AAGAKERQRL ATSLRNAAKA |

| SEQ ID NO | Amino acid sequence |
|---|---|
| | YGEVDEEAAT ALDNDGEGTV QAESAGAVGG DSSAELTDTP RVATAGEPNF MDLKEAARKL ETGDQGASLA HFADGWNTFN LTLQGDVKRF RGFDNWEGDA ATACEASLDQ QRQWILHMAK LSAAMAKQAQ YVAQLHVWAR REHFTYEDIV GLERLYAENP SARDQILPVY AEYQQRSEKV LTEYNNKAAL EPVNPPKPPP AIKIDPPPPP QEQGLIPGFL MPPSDGSGVT PGTGMPAAPM VPPTGSPGGG LPADTAAQLT SAGREAAALS GDVAVKAASL GGGGGGGVPS APLGSAIGGA ESVRPAGAGD IAGLGQGRAG GGAALGGGGM GMPMGAAHQG QGGAKSKGSQ QEDEALYTED RAWTEAVIGN RRRQDSKESK |
| 9 | VADTIQVTPQ MLRSTANDIQ ANMEQAMGIA KGYLANQENV MNPATWSGTG VVASHMTATE ITNELNKVLT GGTRLAEGLV QAAALMEGHE ADSQTAFQAL FGASHGS |
| 10 | MSDQITYNPG AVSDFASDVG SRAGQLHMIY EDTASKTNAL QEFFAGHGAQ GFFDAQAQML SGLQGLIETV GQHGTTTGHV LDNAIGTDQA IAGLF |
| 11 | MSLLDAHIPQ LVASQSAFAA KAGLMRHTIG QAEQAAMSAQ AFHQGESSAA FQAAHARFVA AAAKVNTLLD VAQANLGEAA GTYVAADAAA ASTYTGF |
| 12 | MSQIMYNYPA MLGHAGDMAG YAGTLQSLGA EIAVEQAALQ SAWQGDTGIT YQAWQAQWNQ AMEDLVRAYH AMSSTHEANT MAMMARDTAE AAKWGG |
| 13 | VFSITTLRDW TPDPGSIICW HASPTAKAKA RQAPISEVPP SYQQAQHLRR YRDHVARGLD MSRLMIFTWD LPGRCNIRAM NYAINAHLRR HDTYHSWFEF DNAEHIVRHT IADPADIEVV QAEHQNMTSA ELRRHHIATPQ PLQWDCFLFG IIQSDDHFTF YASIAHLCVD PMIVGVLFIE IHMMYSALVG GDPPIELPPA GRYDDHCVRQ YADTAALTLD SARVRRWVEF AANNDGTLPH FPLPLGDSV PHTGKLLTET LMDEQQGERF EAACVAAGAR FSGGVFACAA LAERELTNCE TFDVVTTTDT RRTPTELRRT GWFTGLVPIT VPVASGLFDS AARVAQISFD SGKDLATVPF DRVLELARPE TGLRPPRPGN FVMSFLDASI APLSTVANSD LNFRIYDEGR VSHQVSMWVN RYQHQTTVTV LFPDNPIASE SVANYIAAMK SIYIRTADGT LATLKPGT |
| 14 | MMQFYDDGVV QLDRAALTLR RYHFPSGTAK VIPLDQIRGY QAESLGFLMA RFNIWGRPDL RRWLPLDVYR PLKSTLVTLD VPGMRPKPAC TPTRPKEFIA LLDELLALHR T |
| 15 | FSRPGLPVEY LQVPSPSMGR DIKVQFQSGG NNSPAVYLLD GLRAQDDYNG WDINTPAFEW YYQSGLSIVM PVGGQSSFYS DWYSPACGKA GCQTYKWETF LTSELPQWLS ANRAVKPTGS AAIGLSMAGS SAMILAAYHP QQFIYAGSLS ALLDPSQGMG PSLIGLAMGD AGGYKAADMW GPSSDPAWER NDPTQQIPKL VANNTRLWVY CGNGTPNELG GANIPAEFLE NFVRSSNLKF QDAYNAAGGH NAVFNFPPNG THSWEYWGAQ LNAMKGDLQS SLGAG |
| 16 | VTVTDDYLAN NVDYASGFKG PLPMPPSKHI AIVACMDARL DVYRMLGIKE GEAHVIRNAG CVVTDDVIRS LAISQRLLGT REIILLHHTD CGMLTFTDDD FKRAIQDETG IRPTWSPESY PDAVEDVRQS LRRIEVNPFV TKHTSLRGFV FDVATGKLNE VTP |
| 17 | FSRPGLPVEY LQVPSPSMGR DIKVQFQSGG NNSPAVYLLD GLRAQDDYNG WDINTPAFEW YYQSGLSIVM PVGGQSSFYS DWYSPACGKA GCQTYKWETF LTSELPQWLS ANRAVKPTGS AAIGLSMAGS SAMILAAYHP QQFIYAGSLS ALLDPSQGMG PSLIGLAMGD AGGYKAADMW GPSSDPAWER NDPTQQIPKL VANNTRLWVY CGNGTPNELG GANIPAEFLE NFVRSSNLKF QDAYNAAGGH NAVFNFPPNG THSWEYWGAQ LNAMKGDLQS SLGAGTEQQW NFAGIEAAAS AIQGNVTSIH SLLDEGKQSL TKLAAAWGGS GSEAYQGVQQ KWDATATELN NALQNLARTI SEAGQAMAST EGNVTGMFA |
| 18 | TEQQWNFAGI EAAASAIQGN VTSIHSLLDE GKQSLTKLAA AWGGSGSEAY QGVQQKWDAT ATELNNALQN LARTISEAGQ AMASTEGNVT GMFAMDLPGN DFDSNDFDAV DLWGADGAEG WTADPIIGVG SAATPDTGPD LDNAHGQAET DTEQEIALFT VTNPPRTVSV STLMDGRIDH VELSARVAWM SESQLASEIL VIADLARQKA QSAQYAFILD RMSQQVDADE HRVALLRKTV |

| SEQ ID NO | Amino acid sequence |
|---|---|
| | GETWGLPSPE EAAAAEAEVF ATRYSDDSPA PDDESDPWMT ENLTVQPERL GVLASHHDNA AVDASSGVEA AAGLGESVAI THGPYSSQFN DTLNVYLTAH NALGSSLHTA GVDLAKSLRI AAKIYSEADE AWRKAIDGLF TMTGFLGVVP SFLKVLAGMH NEIVGDIKRA TDTVAGISGR VQLTHGSFTS KFNDTLQEFE TTRSSTGTGL QGVTSGLANN LLAAAGAYLK ADDGLAGVID KIFGMSTTFA ARLNRLFDTV YPPGRGPHTS AEVIAALKAE GITMSAPYLS QLRSGNRTNP SGATMAALAN FFRIKAAYFT DDEYYEKLDK ELQWLSTMRD DGVRRIAQRA HGLPSAAQQK VLDRIDELRR AEGIDAMEKM SHDPIAADIG TQVSDNALHG VTAGSTALTS VTGLVPAGAD EVSAQAATAF TSEGIQLLAS NASAQDQLHR AGEAVQDVAR TYSQIDDGAA GVFAE |
| 19 | MDLPGNDFDS NDFDAVDLWG ADGAEGWTAD PIIGVGSAAT PDTGPDLDNA HGQAETDTEQ EIALFTVTNP PRTVSVSTLM DGRIDHVELS ARVAWMSESQ LASEILVIAD LARQKAQSAQ YAFILDRMSQ QVDADEHRVA LLRKTVGETW GLPSPEEAAA AEAEVFATRY SDDSPAPDDE SDPWMTENLT VQPERLGVLA SHHDNAAVDA SSGVEAAAGL GESVAITHGP YSSQFNDTLN VYLTAHNALG SSLHTAGVDL AKSLRIAAKI YSEADEAWRK AIDGLFTMTG FLGVVPSFLK VLAGMHNEIV GDIKRATDTV AGISGRVQLT HGSFTSKFND TLQEFETTRS STGTGLQGVT SGLANNLLAA AGAYLKADDG LAGVIDKIFG MSTTFAARLN RLFDTVYPPG RGPHTSAEVI AALKAEGITM SAPYLSQLRS GNRTNPSGAT MAALANFFRI KAAYFTDDEY YEKLDKELQW LSTMRDDGVR RIAQRAHGLP SAAQQKVLDR IDELRRAEGI DAMEKMSHDP IAADIGTQVS DNALHGVTAG STALTSVTGL VPAGADEVSA QAATAFTSEG IQLLASNASA QDQLHRAGEA VQDVARTYSQ IDDGAAGVFA E |
| 20 | MDLPGNDFDS NDFDAVDLWG ADGAEGWTAD PIIGVGSAAT PDTGPDLDNA HGQAETDTEQ EIALFTVTNP PRTVSVSTLM DGRIDHVELS ARVAWMSESQ LASEILVIAD LARQKAQSAQ YAFILDRMSQ QVDADEHRVA LLRKTVGETW GLPSPEEAAA AEAEVFATRY SDDSPAPDDE SDPWMTENLT VQPERLGVLA SHHDNAAVDA SSGVEAAAGL GESVAITHGP YSSQFNDTLN VYLTAHNALG SSLHTAGVDL AKSLRIAAKI YSEADEAWRK AIDGLFTMSR AFIIDPTISA IDGLYDLLGI GIPNQGGILY SSLEYFEKAL EELAAAFPGD GWLGSAADKY AGKNRNHVNF FQELADLDRQ LISLIHDQAN AVQTTRDILE GAKKGLEFVR PVAVDLTYIP VVGHALSAAF QAPPFCAGAMA VVGGALAYLV VKTLINATQL LKLLAKLAEL VAAAIADIIS DVADIIKGTL GEVWEFITNA LNGLKELWDK LTGWVTGLFS RGWSNLESFF AGVPGLTGAT SGLSQVTGLF GAAGLSASSG LAHADSLASS ASLPALAGIG GGSGFGGLPS LAQVHAASTR QALRPRADGP VGAAAEQVGG QSQLVSAQGS QGMGGPVGMG GMHPSSGASK GTTTKKYSEG AAAGTEDAER APVEADAGGG QKVLVRNVVM TGFLGVVPSF LKVLAGMHNE IVGDIKRATD TVAGISGRVQ LTHGSFTSKF NDTLQEFETT RSSTGTGLQG VTSGLANNLL AAAGAYLKAD DGLAGVIDKI FGMSTTFAAR LNRLFDTVYP PGRGPHTSAE VIAALKAEGI TMSAPYLSQL RSGNRTNPSG ATMAALANFF RIKAAYFTDD EYYEKLDKEL QWLSTMRDDG VRRIAQRAHG LPSAAQQKVL DRIDELRRAE GIDAMEKMSH DPIAADIGTQ VSDNALHGVT AGSTALTSVT GLVPAGADEV SAQAATAFTS EGIQLLASNA SAQDQLHRAG EAVQDVARTY SQIDDGAAGV FAE |
| 21 | MDLPGNDFDS NDFDAVDLWG ADGAEGWTAD PIIGVGSAAT PDTGPDLDNA HGQAETDTEQ EIALFTVTNP PRTVSVSTLM DGRIDHVELS ARVAWMSESQ LASEILVIAD LARQKAQSAQ YAFILORMSQ QVDADEHRVA LLRKTVGETW GLPSPEEAAA AEAEVFATRY SDDSPAPDDE SDPWMTENLT VQPERLGVLA SHHDNAAVDA SSGVEAAAGL GESVAITHGP YSSQFNDTLN VYLTAHNALG SSLHTAGVDL AKSLRIAAKI YSEADEAWRK AIDGLFTMSR AFIIDPTISA IDGLYDLLGI GIPNQGGILY SSLEYFEKAL EELAAAFPGD GWLGSAADKY AGKNRNHVNF FQELADLDRQ LISLIHDQAN AVQTTRDILE GAKKGLEFVR PVAVDLTYIP VVGHALSAAF QAPPFCAGAMA VVGGALAYLV VKTLINATQL LKLLAKLAEL VAAAIADIIS DVADIIKGTL MTQGTVTVD QQEILNRANE VEAPMADPPT DVPITPCELT AAKNAAQQLV LSADNMREYL AAGAKERQRL ATSLRNAAKA YGEVDEEAAT ALDNDGEGTV QAESAGAVGG DSSAELTDTP RVATAGEPNF MDLKEAARKL ETGDQGASLA HFADGWNTFN LTLQGDVKRF RGFDNWEGDA ATACEASLDQ QRQWILHMAK LSAAMAKQAQ YVAQLHVWAR REHPTYEDIV GLERLYAENP SARDQILPVY AEYQQRSEKV LTEYNNKAAL EPVNPPKPPP |

| SEQ ID NO | Amino acid sequence |
|---|---|
| | AIKIDPPPPP QEQGLIPGFL MPPSDGSGVT PGTGMPAAPM VPPTGSPGGG LPADTAAQLT SAGREAAALS GDVAVKAASL GGGGGGGVPS APLGSAIGGA ESVRPAGAGD IAGLGQGRAG GGAALGGGGM GMPMGAAHQG QGGAKSKGSQ QEDEALYTED RAWTEAVIGN RRRQDSKESK GEVWEFITNA LNGLKELWDK LTGWVTGLFS RGWSNLESFF AGVPGLTGAT SGLSQVTGLF GAAGLSASSG LAHADSLASS ASLPALAGIG GGSGFGGLPS LAQVHAASTR QALRPRADGP VGAAAEQVGG QSQLVSAQGS QGMGGPVGMG GMHPSSGASK EITTKKYSEG AAAGTEDAER APVEADAGGG QKVLVRNVVM TGFLGVVPSF LKVLAGMHNE IVGDIKRATD TVAGISGRVQ LTHGSFTSKF NDTLQEFETT RSSTGTGLQG VTSGLANNLL AAAGAYLKAD DGLAGVIDKI FGMSTTFAAR LNRLFDTVYP PGRGPHTSAE VIAALKAEGI TMSAPYLSQL RSGNRTNPSG ATMAALANFF RIKAAYFTDD EYYEKLDKEL QWLSTMRDDG VRRIAQRAHG LPSAAQQKVL DRIDELRRAE GIDAMEKMSH DPIAADIGTQ VSDNALHGVT AGSTALTSVT GLVPAGADEV SAQAATAFTS EGIQLLASNA SAQDQLHRAG EAVQDVARTY SQIDDGAAGV FAE |
| 22 | MTQSQTVTVD QQEILNRANE VEAPMADPPT DVPITPCELT AAKNAAQQLV LSADNMREYL AAGAKERQRL ATSLRNAAKA YGEVDEEAAT ALDNDGEGTV QAESAGAVGG DSSAELTDTP RVATAGEPNF MDLKEAARKL ETGDQGASLA HFADGWNTFN LTLQGDVKRF RGFDNWEGDA ATACEASLDQ QRQWILHMAK LSAAMAKQAQ YVAQLHVWAR REHPTYEDIV GLERLYAENP SARDQILPVY AEYQQRSEKV LTEYNNKAAL EPVNPPKPPP AIKIDPPPPP QEQGLIPGFL MPPSDGSGVT PGTGMPAAPM VPPTGSPGGG LPADTAAQLT SAGREAAALS GDVAVKAASL GGGGGGGVPS APLGSAIGGA ESVRPAGAGD IAGLGQGRAG GGAALGGGGM GMPMGAAHQG QGGAKSKGSQ QEDEALYTED RAWTEAVIGN RRRQDSKESK MDLPGNDFDS NDFDAVDLWG ADGAEGWTAD PIIGVGSAAT PDTGPDLDNA HGQAETDTEQ EIALFTVTNP PRTVSVSTLM DGRIDHVELS ARVAWMSESQ LASEILVIAD LARQKAQSAQ YAFILDRMSQ QVDADEHRVA LLRKTVGETW GLPSPEEAAA AEAEVFATRY SDDSPAPDDE SDPWMTENLT VQPERLGVLA SHHDNAAVDA SSGVEAAAGL GESVAITHGP YSSQFNDTLN VYLTAHNALG SSLHTAGVDL AKSLRIAAKI YSEADEAWRK AIDGLFTMTG FLGVVPSFLK VLAGMHNEIV GDIKRATDTV AGISGRVQLT HGSFTSKFND TLQEFETTRS STGTGLQGVT SGLANNLLAA AAGAYLKADD GLAGVIDKIF GMSTTFAARLN RLFDTVYPPG RGPHTSAEVI AALKAEGITM SAPYLSQLRS GNRTNPSGAT MAALANFFRI KAAYFTDDEY YEKLDKELQW LSTMRDDGVR RIAQRAHGLP SAAQQKVLDR IDELRRAEGI DAMEKMSHDP IAADIGTQVS DNALHGVTAG STALTSVTGL VPAGADEVSA QAATAFTSEG IQLLASNASA QDQLHRAGEA VQDVARTYSQ IDDGAAGVFA E |
| 23 | ADTIQVTPQM LRSTANDIQA NMEQAMGIAK GYLANQENVM NPATWSGTGV VASHMTATEI TNELNKVLTG GTRLAEGLVQ AAALMEGHEA DSQTAFQALF GASHGSGLVP RGSTGMSDQI TYNPGAVSDF ASDVGSRAGQ LHMIYEDTAS KTNALQEFFA GHGAQGFFDA QAQMLSGLQG LIETVGQHGT TTGHVLDNAI GTDQAIAGLF LIGAHPRALN VVKFGGAAFL MSLLDAHIPQ LVASQSAFAA KAGLMRHTIG QAEQAAMSAQ AFHQGESSAA FQAAHARFVA AAKVNTLLD VAQANLGEAA GTYVAADAAS ASTYTGFGLV PRGSTGMSQI MYNYPAMLGH AGDMAGYAGT LQSLGAEIAV EQAALQSAWQ GDTGITYQAW QAQWNQAMED LVRAYHAMSS THEANTMAMM ARDTAEAAKW GGLGFGAGRL RGLFTNPGSW RIMTSRFMTD PHAMRDMAGR FEVHAQTVED EARRMWASAQ NISGAGWSGM AEATSLDTMT QMNQAFRNIV NMLHGVRDGL VRDANNYEQQ EQASQQILSS GLVPRGSTGM TINYQFGDVD AHGAMIRAQA GSLEAEHQAI ISDVLTASDF WGGAGSAASQ GFITQLGRNF QVIYEQANAH GQKVQAAGNN MAQTDSAVGS SWA |
| 24 | MSRAFIIDPT ISAIDGLYDL LGIGIPNQGG ILYSSLEYFE KALEELAAAF PGDGWLGSAA DKYAGKNRNH VNFFQELADL DRQLISLIHD QANAVQTTRD ILEGAKKGLE FVRPVAVDLT YIPVVGHALS AAFQAPFCAG AMAVVGGALA YLVVKTLINA TQLLKLLAKL AELVAAAIAD IISDVADIIK GTLGEVWEFI TNALNGLKEL WDKLTGWVTG LFSRGWSNLE SFFAGVPGLT GATSGLSQVT GLFGAAGLSA SSGLAHADSL ASSASLPALA GIGGGSGFGG LPSLAQVHAA STRQALRPRA DGPVGAAAEQ VGGQSQLVSA QGSQGMGGPV GMGGMHPSSG ASKGTTTKKY SEGAAAGTED AERAPVEADA GGGQKVLVRN VVMTENLTVQ |
| | PERLGVLASH HDNAAVDASS GVEAAAGLGE SVAITHGPYC SQFNDTLNVY LTAHNALGSS LHTAGVDLAK SLRIAAKIYS EADEAWRKAI DGLFTVFSIT TLRDWTPDPG SIICWHASPT AKAKARQAPI SEVPPSYQQA QHLRRYRDHV ARGLDMSRLM IFTWDLPGRC NIRAMNYAIN AHLRRHDTYH SWFEFDNAEH IVRHTIADPA DIEVVQAEHQ NMTSAELRHH IATPQPLQWD CFLFGIIQSD DHFTFYASIA HLCVDPMIVG VLFIEIHMMY SALVGGDPPI ELPPAGRYDD HCVRQYADTA ALTLDSARVR RWVEFAANND GTLPHFPLPL GDLSVPHTGK LLTETLMDEQ QGERFEAACV AAGARFSGGV FACAALAERE LTNCETFDVV TTTDTRRTPT ELRTTGWFTG LVPITVPVAS GLFDSAARVA QISFDSGKDL ATVPFDRVLE LARPETGLRP PRPGNFVMSF LDASIAPLST VANSDLNFRI YDEGRVSHQV SMWVNRYQHQ TTVTVLFPDN PIASESVANY IAAMKSIYIR TADGTLATLK PGTMMQFYDD GVVQLDRAAL TLRRYHFPSG TAKVIPLDQI RGYQAESLGF LMARFNIWGR PDLRRWLPLD VYRPLKSTLV TLDVPGMRPK PACTPTRPKE FIALLDELLA LHRTMSLLDA HIPQLVASQS AFAAKAGLMR HTIGQAEQAA MSAQAFHQGE SSAAFQAAHA RFVAAAAKVN TLLDVAQANL GEAAGTYVAA DAAAASTYTG FMSQIMYNYP AMLGHAGDMA GYAGTLQSLG AEIAVEQAAL QSAWQGDTGI TYQAWQAQWN QAMEDLVRAY HAMSSTHEAN TMAMMARDTA EAAKWGG |
| 25 | MTQSQTVTVD QQEILNRANE VEAPMADPPT DVPITPCELT AAKNAAQQLV LSADNMREYL AAGAKERQRL ATSLRNAAKA YGEVDEEAAT ALDNDGEGTV QAESAGAVGG DSSAELTDTP RVATAGEPNF MDLKEAARKL ETGDQGASLA HFADGWNTFN LTLQGDVKRF RGFDNWEGDA ATACEASLDQ QRQWILHMAK LSAAMAKQAQ YVAQLHVWAR REHPTYEDIV GLERLYAENP SARDQILPVY AEYQQRSEKV LTEYNNKAAL EPVNPPKPPP AIKIDPPPPP QEQGLIPGFL MPPSDGSGVT PGTGMPAAPM VPPTGSPGGG LPADTAAQLT SAGREAAALS GDVAVKAASL GGGGGGGVPS APLGSAIGGA ESVRPAGAGD IAGLGQGRAG GGAALGGGGM GMPMGAAHQG QGGAKSKGSQ QEDEALYTED RAWTEAVIGN RRRQDSKESK MSRAFIIDPT ISAIDGLYDL LGIGIPNQGG ILYSSLEYFE KALEELAAAF PGDGWLGSAA DKYAGKNRNH VNFFQELADL DRQLISLIHD QANAVQTTRD ILEGAKKGLE FVRPVAVDLT YIPVVGHALS AAFQAPFCAG AMAVVGGALA YLVVKTLINA TQLLKLLAKL AELVAAAIAD IISDVADIIK GTLGEVWEFI TNALNGLKEL WDKLTGWVTG LFSRGWSNLE SFFAGVPGLT GATSGLSQVT GLFGAAGLSA SSGLAHADSL ASSASLPALA GIGGGSGFGG LPSLAQVHAA STRQALRPRA DGPVGAAAEQ VGGQSQLVSA QGSQGMGGPV GMGGMHPSSG ASKGTTTKKY SEGAAAGTED AERAPVEADA GGGQKVLVRN VVMTENLTVQ PERLGVLASH HDNAAVDASS GVEAAAGLGE SVAITHGPYC SQFNDTLNVY LTAHNALGSS LHTAGVDLAK SLRIAAKIYS EADEAWRKAI DGLFTVESIT TLRDWTPDPG SIICWHASPT AKAKARQAPI SEVPPSYQQA QHLRRYRDHV ARGLDMSRLM IFTWDLPGRC NIRAMNYAIN AHLRRHDTYH SWFEFDNAEH IVRHTIADPA DIEVVQAEHQ NMTSAELRHH IATPQPLQWD CFLFGIIQSD DHFTFYASIA HLCVDPMIVG SALVGGDPPI ELPPAGRYDD HCVRQYADTA ALTLDSARVR RWVEFAANND GTLPHFPLPL GDLSVPHTGK LLTETLMDEQ QGERFEAACV AAGARFSGGV FACAALAERE LTNCETFDVV TTTDTRRTPT ELRTTGWFTG LVPITVPVAS GLFDSAARVA QISFDSGKDL ATVPFDRVLE LARPETGLRP PRPGNFVMSF LDASIAPLST VANSDLNFRI YDEGRVSHQV SMWVNRYQHQ TTVTVLFPDN PIASESVANY IAAMKSIYIR TADGTLATLK PGTMMQFYDD GVVQLDRAAL TLRRYHFPSG TAKVIPLDQI RGYQAESLGF LMARFNIWGR PDLRRWLPLD VYRPLKSTLV TLDVPGMRPK PACTPTRPKE FIALLDELLA LHRTMSLLDA HIPQLVASQS AFAAKAGLMR HTIGQAEQAA MSAQAFHQGE SSAAFQAAHA RFVAAAAKVN TLLDVAQANL GEAAGTYVAA DAAAASTYTG FMSQIMYNYP AMLGHAGDMA GYAGTLQSLG AEIAVEQAAL QSAWQGDTGI TYQAWQAQWN QAMEDLVRAY HAMSSTHEAN TMAMMARDTA EAAKWGG |
| 26 | FSRPGLPVEY LQVPSPSMGR DIKVQFQSGG NNSPAVYLLD GLRAQDDYNG WDINTPAFEW YYQSGLSIVM PVGGQSSFYS DWYSPACGKA GCQTYKWETF LTSELPQWLS ANRAVKPTGS AAIGLSMAGS SAMILAAYHP QQFIYAGSLS ALLDPSQGMG PSLIGLAMGD AGGYKAADMW GPSSDPAWER NDPTQQIPKL VANNTRLWVY CGNGTPNELG GANIPAEFLE NFVRSSNLKF QDAYNAAGGH NAVFNFPPNG THSWEYWGAQ LNAMKGDLQS SLGAGTEQQW NFAGIEAAAS AIQGNVTSIH SLLDEGKQSL |

-continued

| SEQ ID NO | Amino acid sequence | | | |
|---|---|---|---|---|
| | TKLAAAWGGS | GSEAYQGVQQ | KWDATATELN | NALQNLARTI |
| | SEAGQAMAST | EGNVTGMFAT | VTDDYLANNV | DYASGFKGPL |
| | PMPPSKHIAI | VACMDARLDV | YRMLGIKEGE | AHVIRNAGCV |
| | VTDDVIRSLA | ISQRLLGTRE | IILLHHTDCG | MLTFTDDDFK |
| | RAIQDETGIR | PTWSPESYPD | AVEDVRQSLR | RIEVNPFVTK |
| | HTSLRGFVFD | VATGKLNEVT | P | |

FIGURE LEGENDS

FIG. 1. Mycobacterial load in mice after preventive vaccination with single antigens. *M. tuberculosis* bacteria was enumerated in lungs of individual mice six weeks after aerosol challenge. Prior to challenge groups of mice were vaccinated with individual antigens or BCG and one group received saline injections. One way analysis of variance (ANOVA) in combination with Tukey's multiple comparisons test was used to statistical test if the bacterial number in vaccinated groups were significantly lower than in lungs of animals from the saline control group (***$p<0.01$) six weeks after challenge. The mean and standard error of mean (SEM) are shown for each group.

Figure 2:
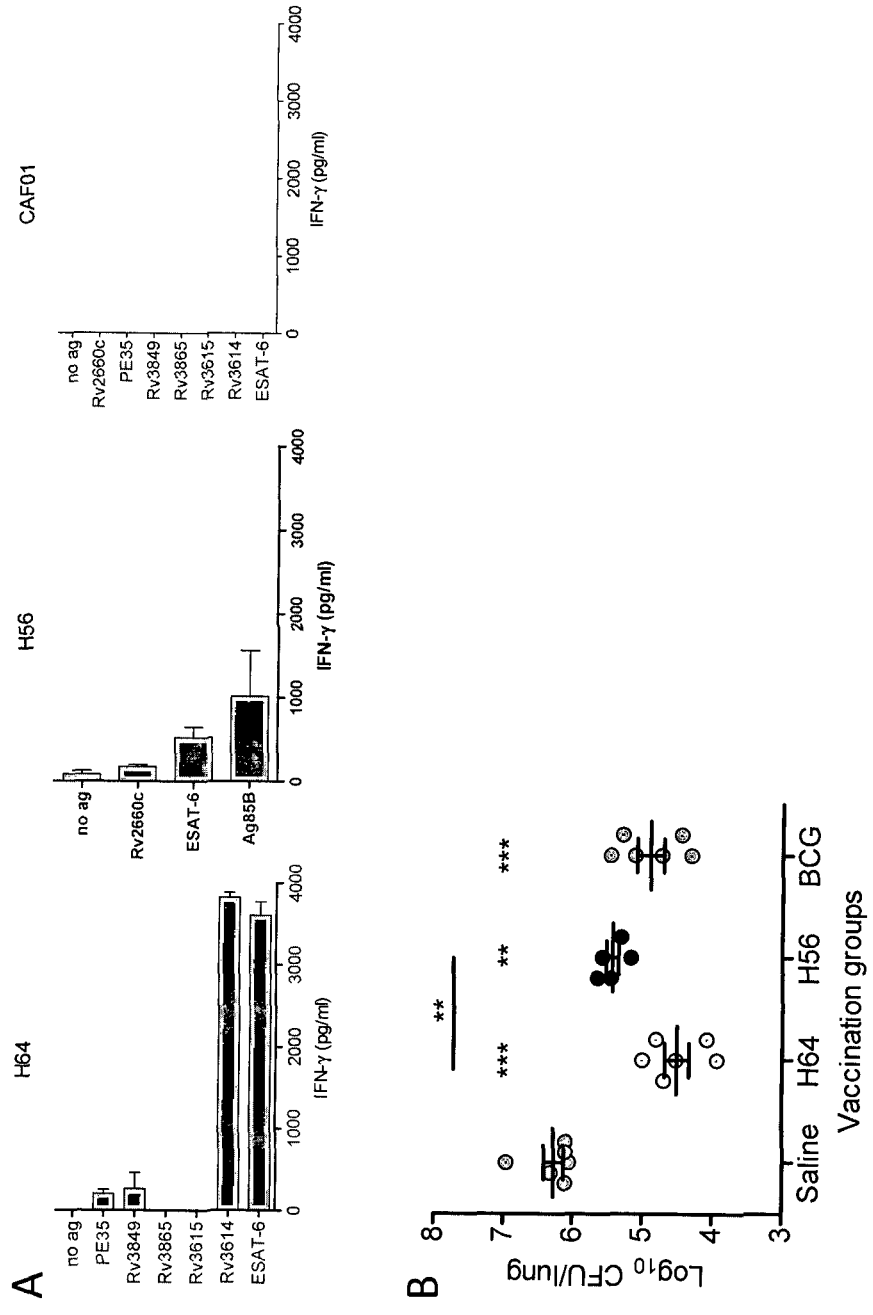

FIG. 2. Immune responses and mycobacteria load after H64 vaccination. After vaccination with the fusion proteins H64 or H56 (Ag85B-ESAT6-Rv2660c) in CAF01 adjuvant (DDA/TDB) the T cell response towards the individual proteins in the two fusions was tested (A). Readout was secreted IFN-g after three days of in vitro stimulation with single antigens. Six weeks after being challenge with *M. tb* the bacterial burden in the lung was measured and compared among the groups using one-way-ANOVA combined with Tukey's multiple comparisons test (*$p<0.01$ $p<0.05$. The mean and SEM are shown for each group.

Figure 3:
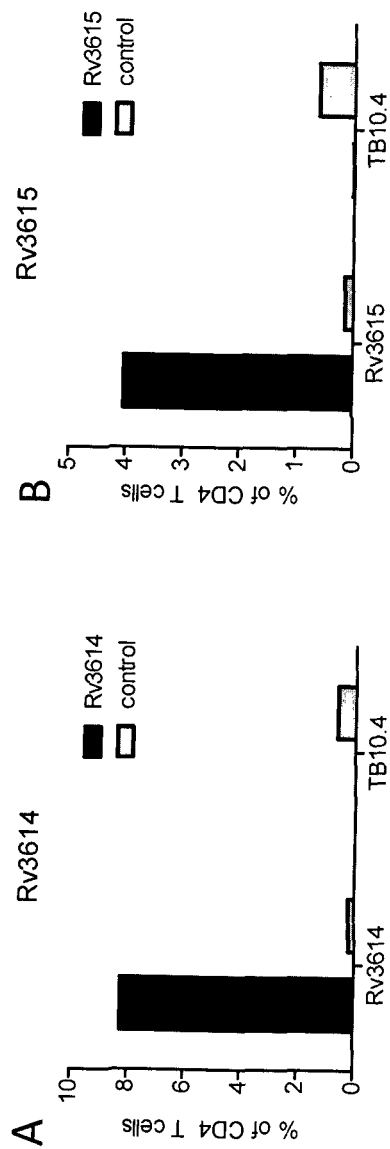

FIG. 3 Post-exposure vaccination with Rv3614 or Rv3615c resulted in significant vaccine specific immune responses. 1 week after vaccination lymphocytes obtained from the lung of the mice were used to evaluated vaccine-induced T cell immune response. Readout was frequency of cytokine positive CD4 T cells (expressing either IFN-$\gamma$, IL-2, TNF-$\alpha$ or any combination) in the cell culture after 5 hours of in vitro stimulation with the vaccine antigens i.e. (A) Rv3614 or (B) Rv3615c. TB10.4 was included as a control antigen for the infection driven immune response. Data shown as mean and represent a pool of 4 mice.

Figure 4:
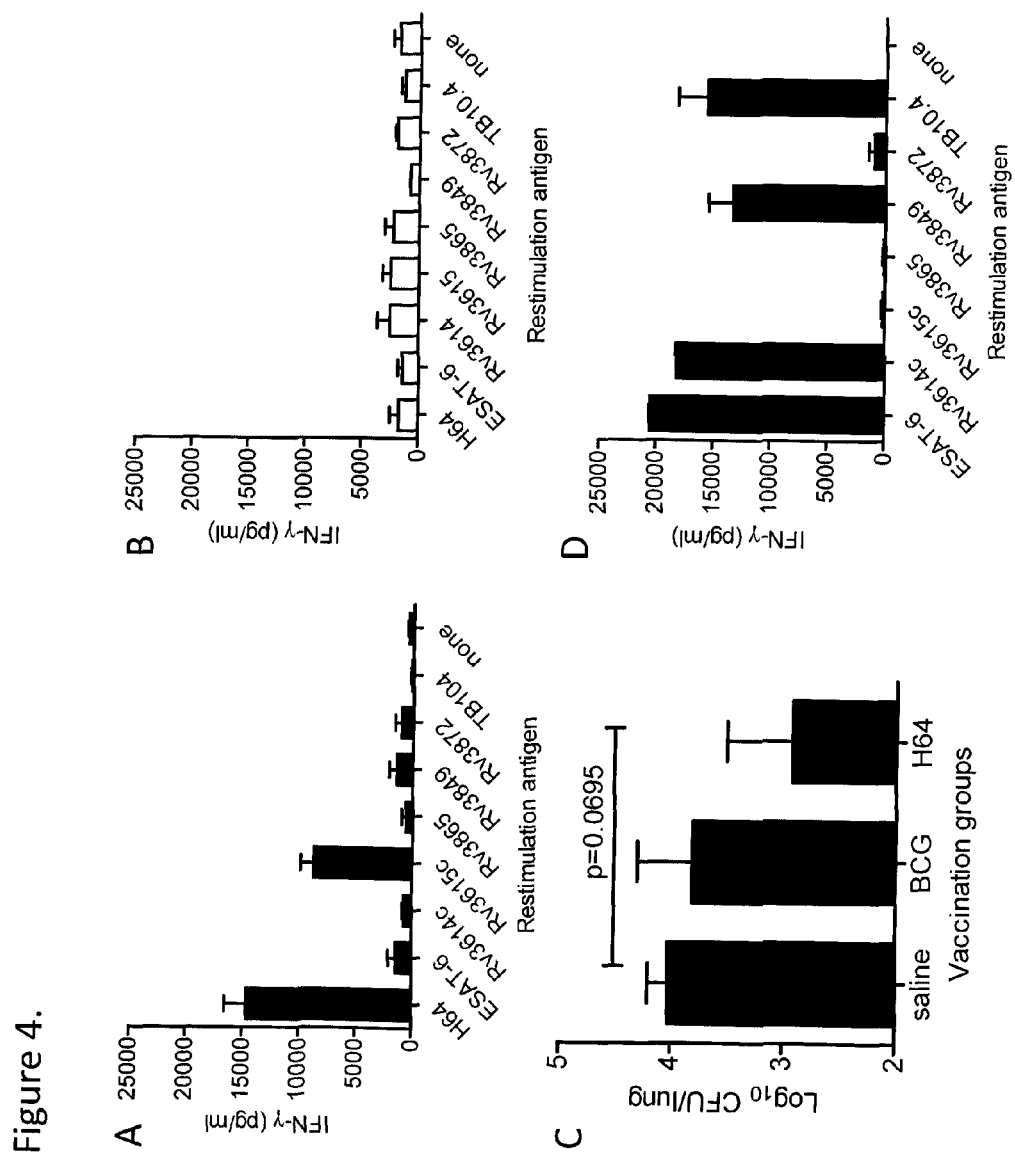

FIG. 4. Post-exposure vaccination with H64. Vaccine responses and protective efficacy. After post-exposure vaccination with H64 the T cell response towards the individual protein and/or the whole fusion was tested (A, B and D). Readout was IFN-$\gamma$ secretion after three days of in vitro stimulation with the single antigens or whole fusion-protein and was done for both vaccinated FvB (A) and CB6F1 mice (D) and control mice (B). (C) 37 weeks post *M. tb*. challenge (21 weeks post final vaccination) the bacterial burden in the lungs was measured and compared between the groups using one-way-ANOVA combined with Tukey's multiple comparisons test. The mean and SEM are shown for each group.

Figure 5:
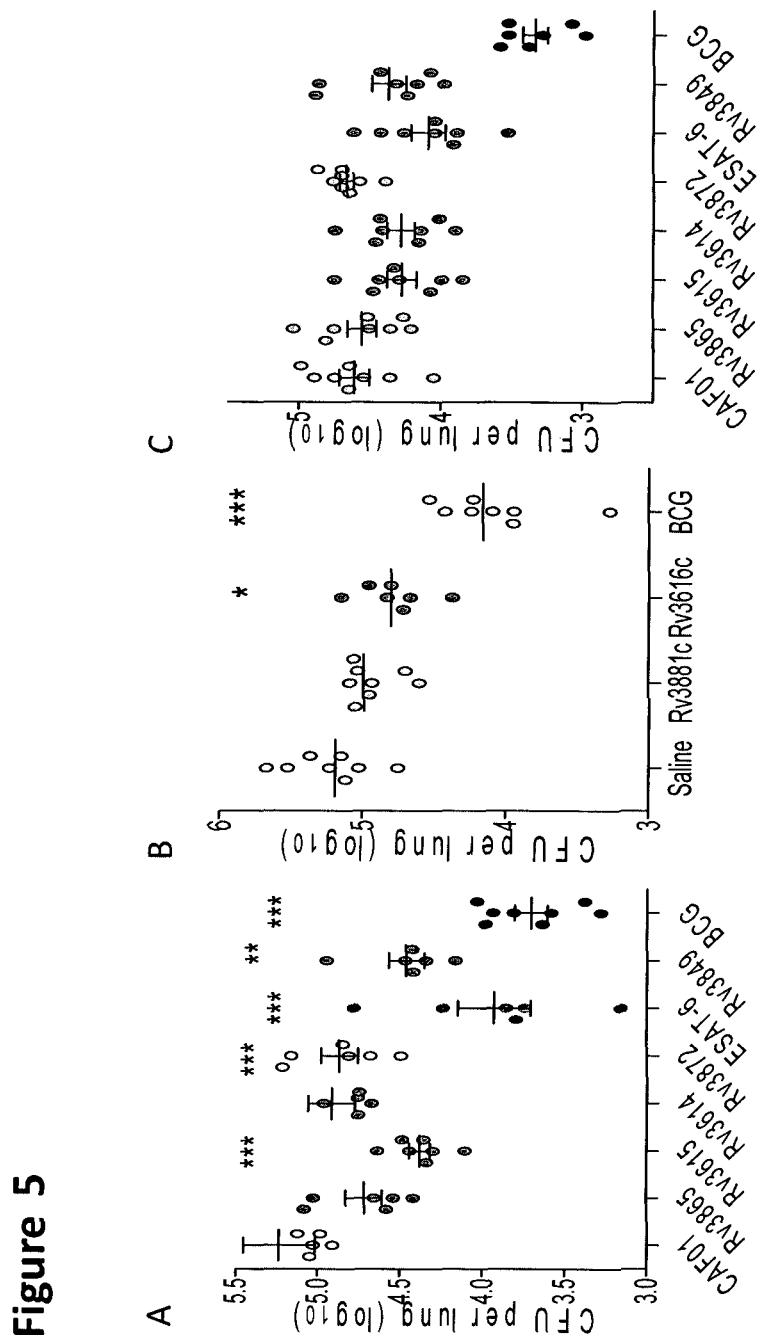

FIG. 5. Mycobacterial tuberculosis load in mice after preventive vaccination with single antigens. *M. tuberculosis* bacteria was enumerated in lungs of individual mice six weeks after aerosol challenge. Prior to challenge groups of mice were vaccinated with individual antigens or BCG and one group received three saline injections. In A and B the B6C3F1 mouse strain was used and in C the CB6F1 strain. One way analysis of variance (ANO-VA) in combination with Tukey's multiple comparisons test was used to statistical test if the bacterial number in vaccinated groups were significantly lower than in lungs of animals from the saline control group (***$p<0.01$) six weeks after challenge. The mean and standard error of mean (SEM) are shown for each group.

Figure 6:
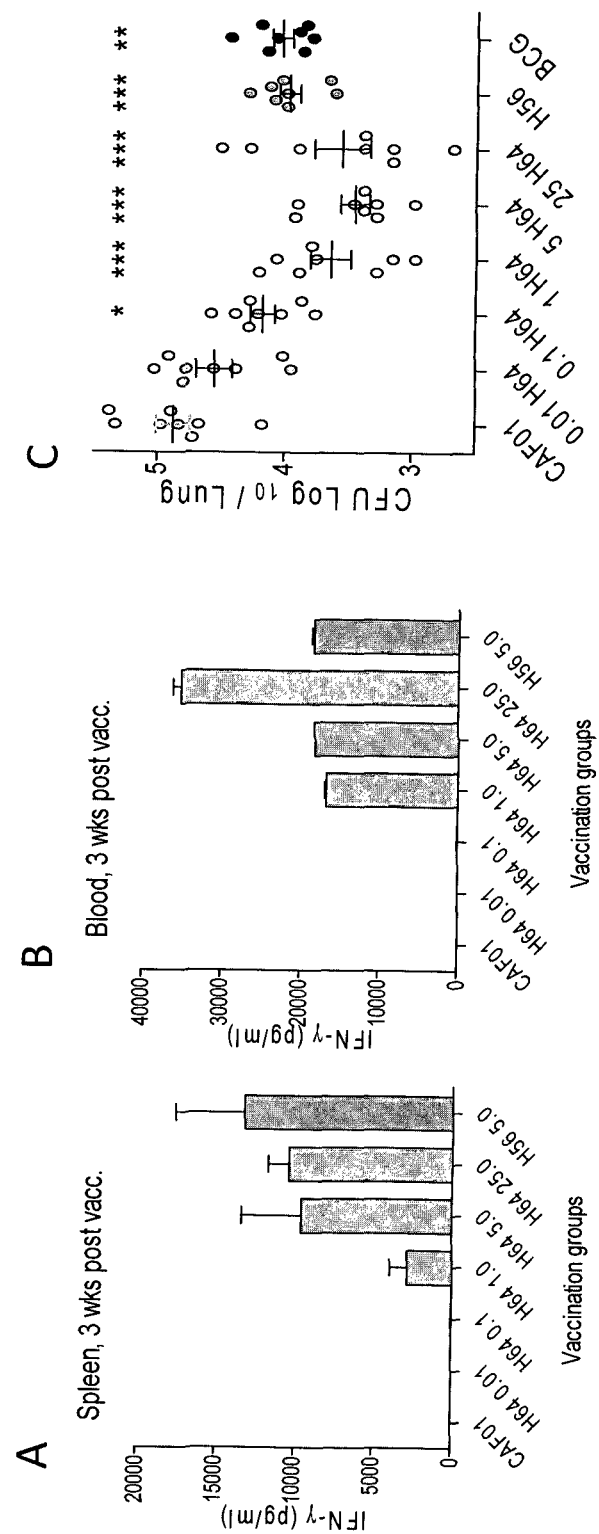

FIG. 6. Groups of CB6F1 mice were either vaccinated three times with H64 fusion protein using protein doses from 0.01 to 25 ug per animal per vaccination round or 5 ug of the H56 fusion protein. Three weeks after third vaccination the vaccine specific T cell response was measured in spleen (A)(n=3) and blood (B) by restimulation with vaccine antigens. Six weeks after vaccination all animals were aerosolly challenged with virulent *M. tb* strain Erdman. Six weeks after infection *M. tb* bacteria was enumerated in lungs of individual mice (C). ANOVA and Tukey's multiple comparisons test was used to statistical test if the bacterial number in vaccinated groups were significantly lower than in lungs of animals from the saline control group (*$p<0.001$; $p<0.01$; *$p<0.05$)

Figure 7:
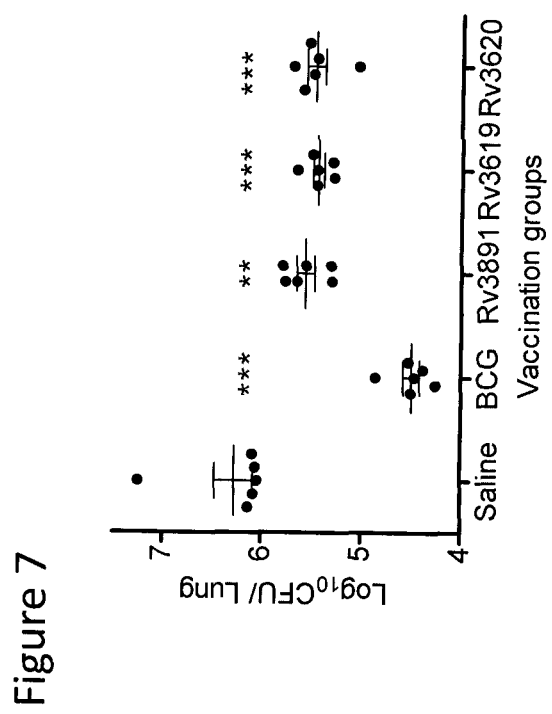

FIG. 7. Mycobacterial load in mice after preventive vaccination with single antigens. *M. tuberculosis* bacteria were enumerated in lungs of individual mice six weeks after aerosol challenge. Prior to challenge groups of mice were vaccinated with Rv3891, Rv3619, Rv3620 or BCG or received saline injections. One way analysis of variance (ANOVA) in combination with Tukey's multiple comparisons test was used to compare the bacterial burden among the groups (*$p<0.01$; $p<0.05$ relative to the saline group).

Figure 8:
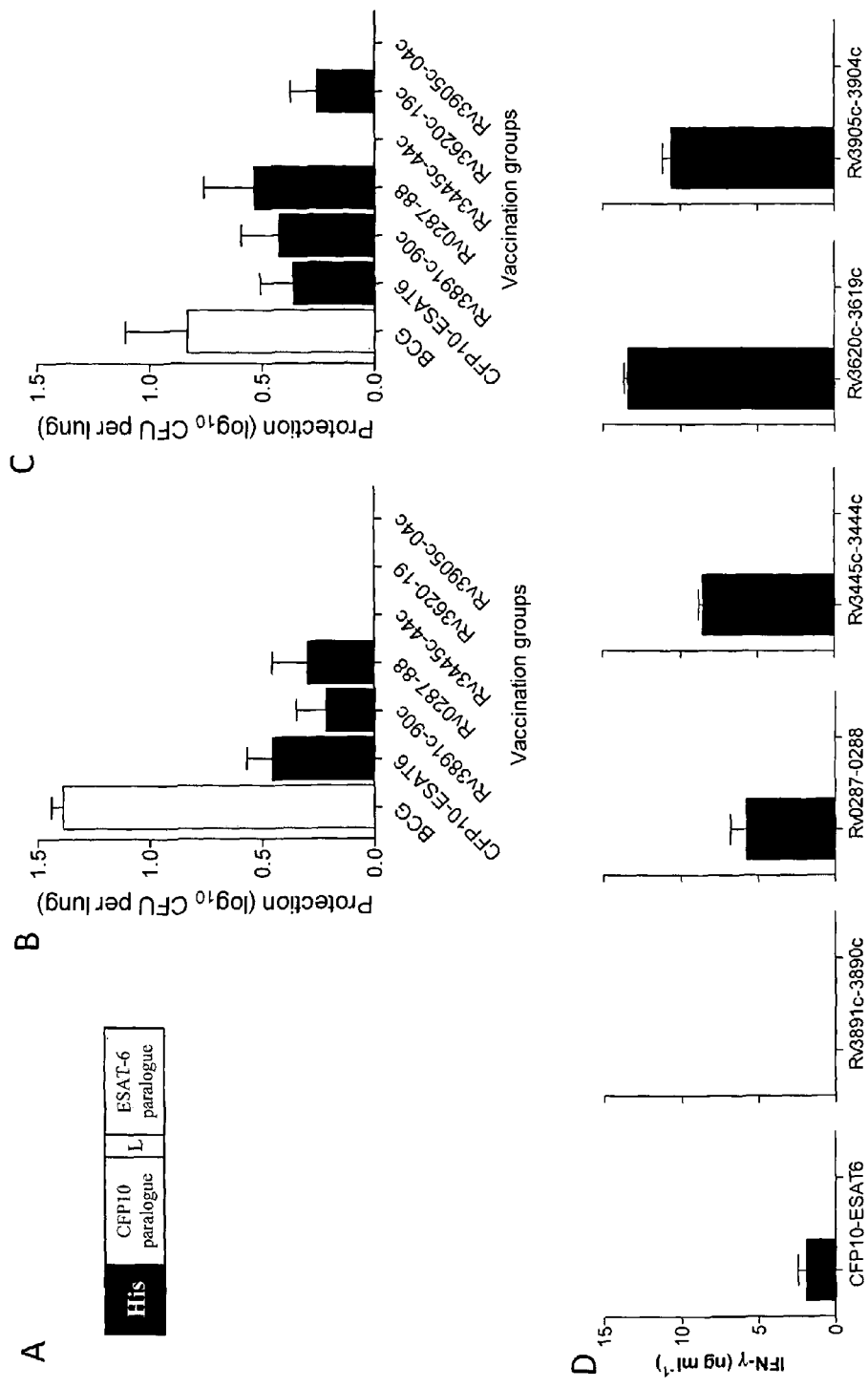

FIG. 8. Dimer fusions of ESAT-6 family proteins. Schematic representation of the six fusions (A). CFP10 paralogue is either Rv3891c, Rv0287, Rv3445c, Rv3620c, Rv3905c or CFP10. The ESAT-6 paralogue is either Rv3890c, Rv0288, Rv3444c, Rv3619c, Rv3904c or ESAT-6. The amino acid sequence for the linker is GLVPRGSTG in all six constructs. Protective efficacy was measured in lungs of individual mice six weeks after aerosol challenge in CB6F1 mice (B) and B6C3F1 mice (C). Vaccine induced responses were determined in B6C3F1 mice by stimulating PBMC's isolated 3 weeks after third vaccination (D). Each panel illustrate results from one vaccination group. PBMC's from each groups were either stimulated with the vaccine antigen or a control protein (BSA)

Figure 9:
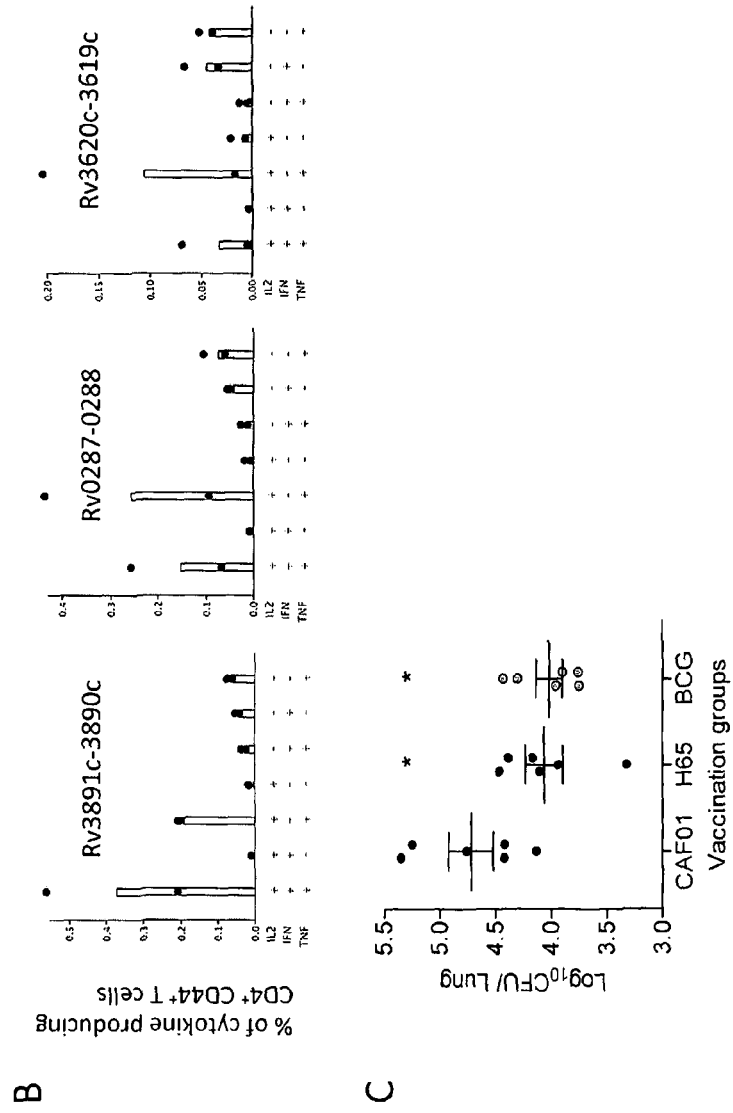

FIG. 9. Vaccination of B6C3F1 mice with H65. Schematic representation of the H65 fusion consisting of six ESAT-6 family proteins separated by either a 9 aa linker (L) or 20 aa linkers (LL1 and LL2) (A). The 9 aa linker is identical to the linker used for the dimer fusions (GLVPRGSTG). The sequence of the LL1 linker is LIGAHPRALNVVKFG-GAAFL and for the LL2 linker LGFGAGRLRGLFTNPG-SWRI. Cytokine responses measured by flowcytometri against each of the ESX-2 (Rv3891c-Rv3890c), ESX-3 (Rv0287-Rv0288) and ESX-5 (Rv3620c-Rv3619c) dimer substrates in splenocytes isolated three weeks after third H65 vaccinated (B). Mycobacterial load in B6C3F1 mice after preventive vaccination with H65 or BCG (C). *M. tuberculosis* bacteria were enumerated in lungs of individual mice six weeks after aerosol challenge. One-way-ANOVA in combination with Tukey's multiple comparisons test was used to compare the bacterial burden among the groups (*$p<0.1$ relative to the saline group).

Figure 10:
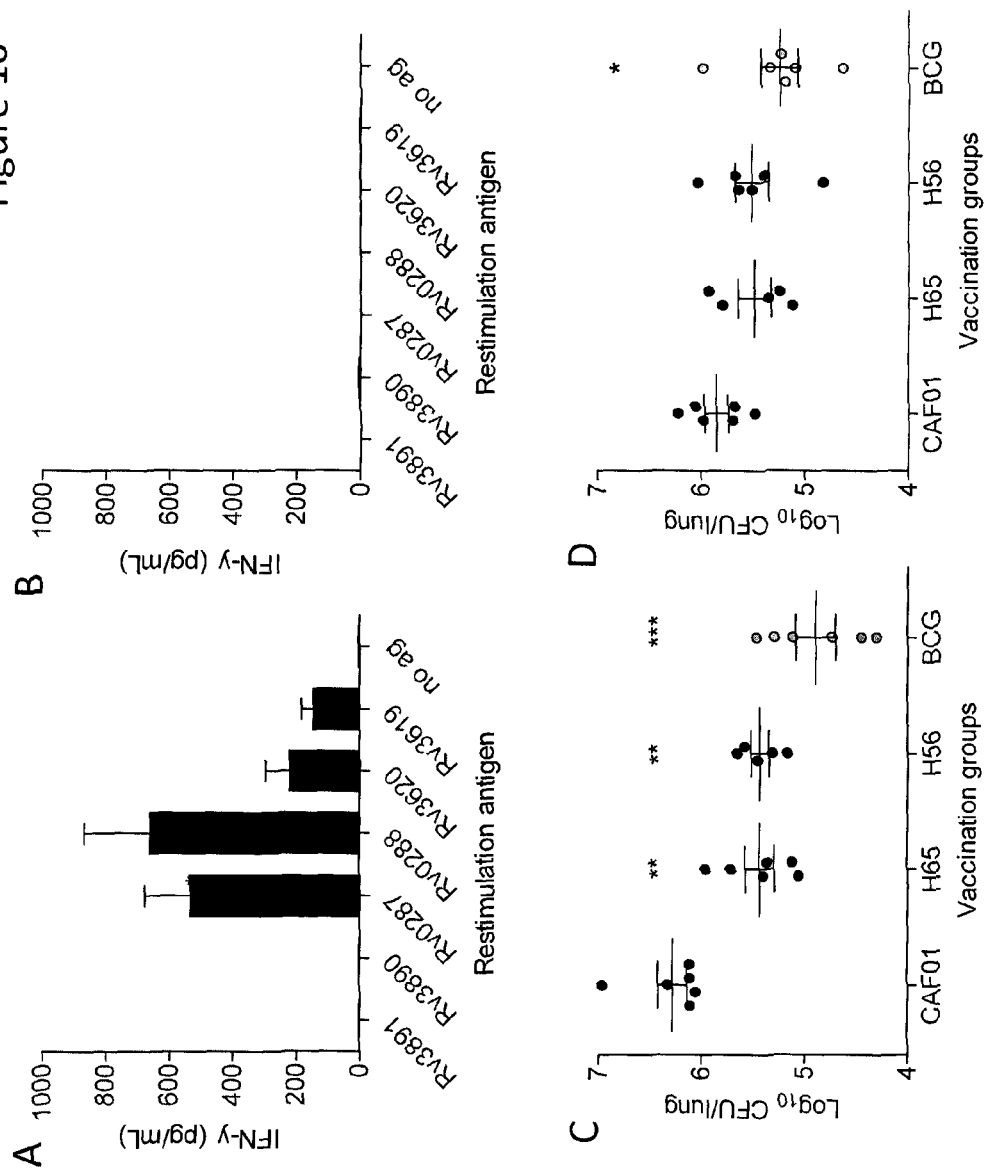

FIG. 10. H65 vaccination in CB6F1 mice—immune response and protective efficacy. Antigen specific secretion of the cytokine IFN-$\gamma$ by splenocytes isolated three weeks after third vaccination with H65/CAF01 (A) or third injection with saline (B). CFU in four groups of CB6F1 mice six (C) and twenty-four (D) weeks after challenge.

Figure 11:
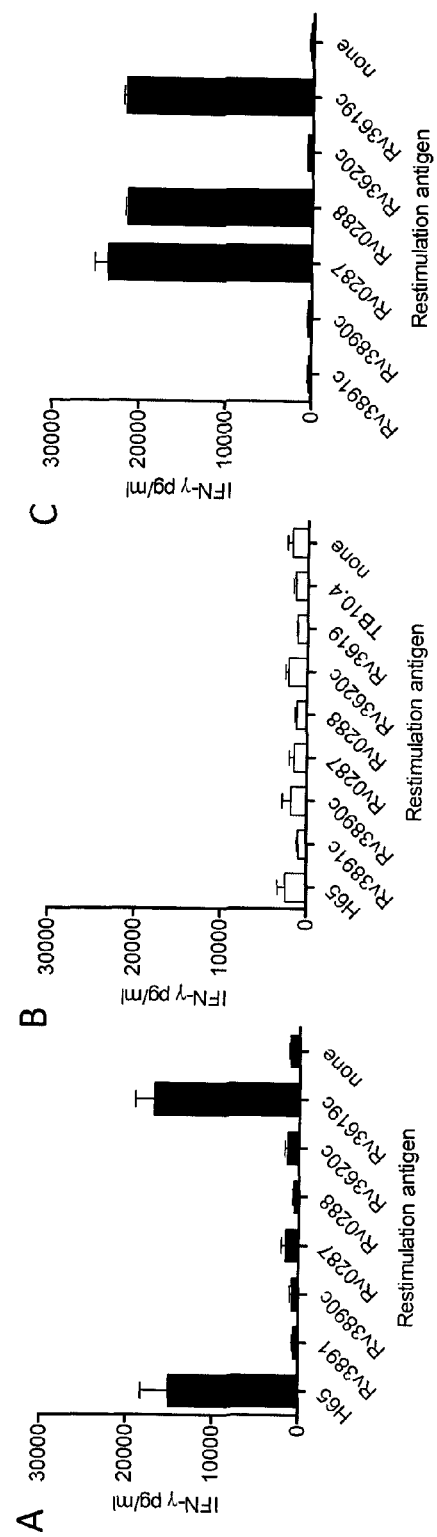

FIG. 11. Vaccine-induced immune response after post-exposure vaccination with H65. After post-exposure vaccination with H65 the T cell reponse towards the individual protein and/or the whole fusion was tested (A-C). Readout was IFN-γ secretion after three days of in vitro stimulation with the single antigens for the CB6F1 mouse strain (C) and both single antigens and whole fusion-protein in the FvB mouse strain (A: vaccinated and B: control).

Figure 12:
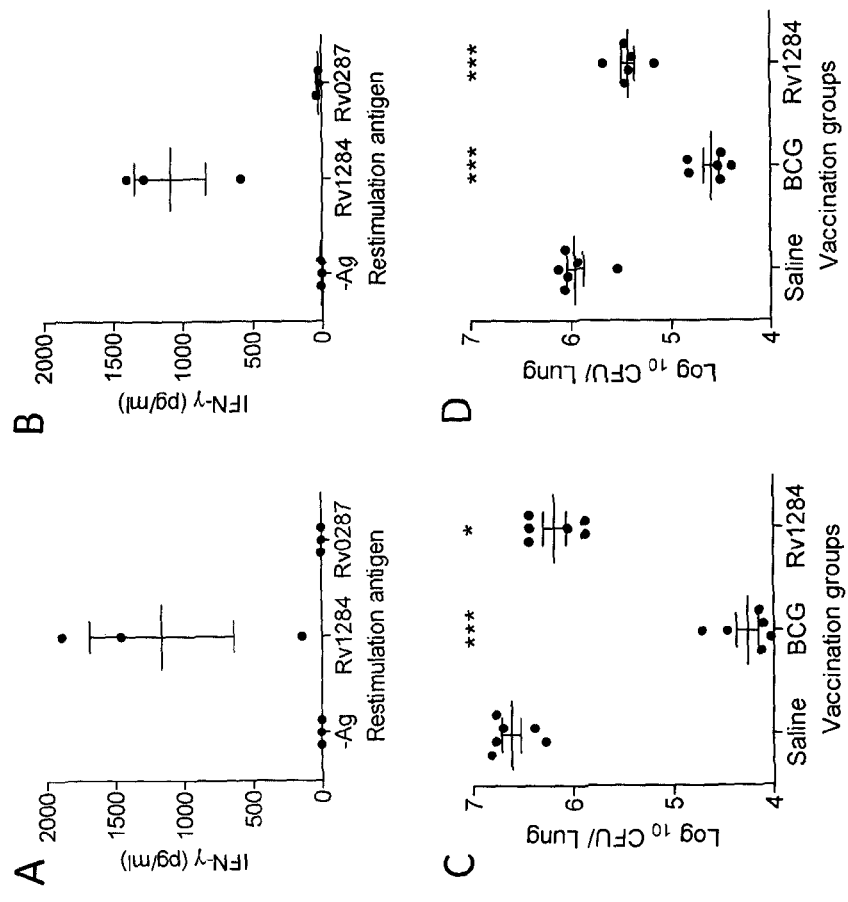

FIG. 12. Rv1284 (canA) vaccination in two mice strains. Secreted cytokine IFN-γ was measuren in cell medium after incubating PBMC's with either 2 µg of Rv1284 or Rv0287 or with buffer control for 72 hours. The PBMC's were isolated from CB6F1 mice (A) or B6C3F1 mice (B) two weeks after the third Rv1284/CAF01vaccination. Six weeks after Mtb challenge the number of mycobacteria was measured in CB6F1 mice (C) or B6C3F1 mice (D).

Figure 13:
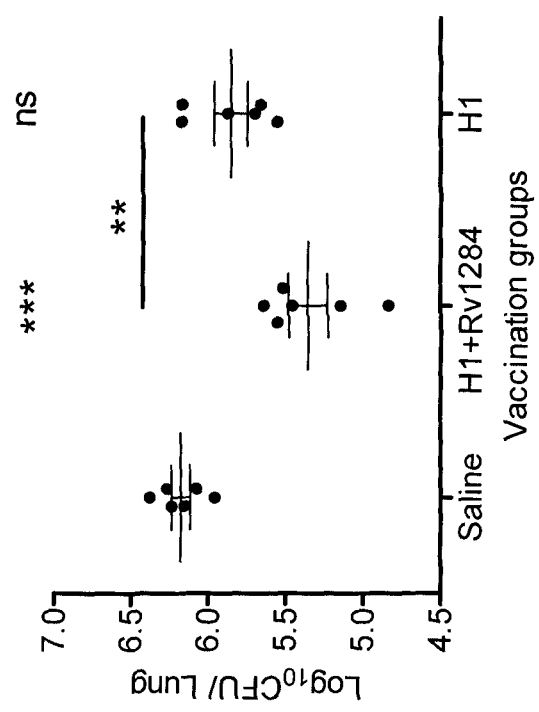

FIG. 13. H1+Rv1284 vaccination. Bacteria load (CFU) in groups of FVB mice six weeks after an aerosol Mtb challenge. The mice were either vaccinated three times with 5 µg H1(Ag85B-ESAT6)/CAF01, 5 µg (total) H1(Ag85B-ESAT6)+Rv1284 formulated in CAF01 or injected three times with saline (control group).

Figure 14:
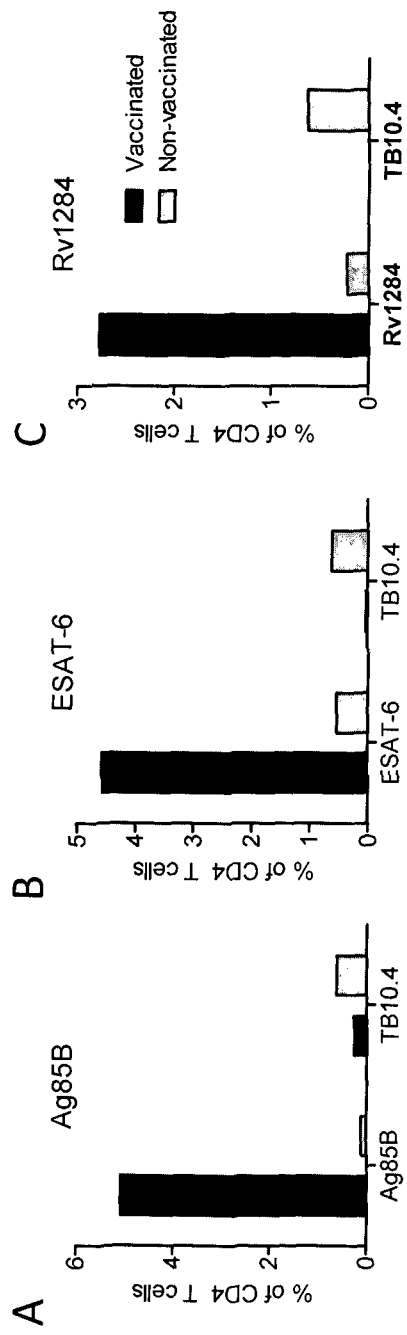

FIG. 14. Immune response following post-exposure vaccination with the antigens Ag85B, ESAT-6 or Rv1284. 1 week after vaccination lymphocytes obtained from the lung of the mice were used to evaluated vaccine-induced T cell immune response to either Ag85B, ESAT6- or Rv1284, all components of H67. Readout was frequency of cytokine positive CD4 T cells (expressing either IFN-γ, IL-2, TNF-α or any combination) in the cell culture after 5 hours of in vitro stimulation with the vaccine antigens and shown for (A) Ag85B, (B) ESAT6 and (C) Rv1284. TB10.4 was included as a control antigen for the infection driven immune response. Data shown as mean and represent a pool of 4 mice.

Figure 15:
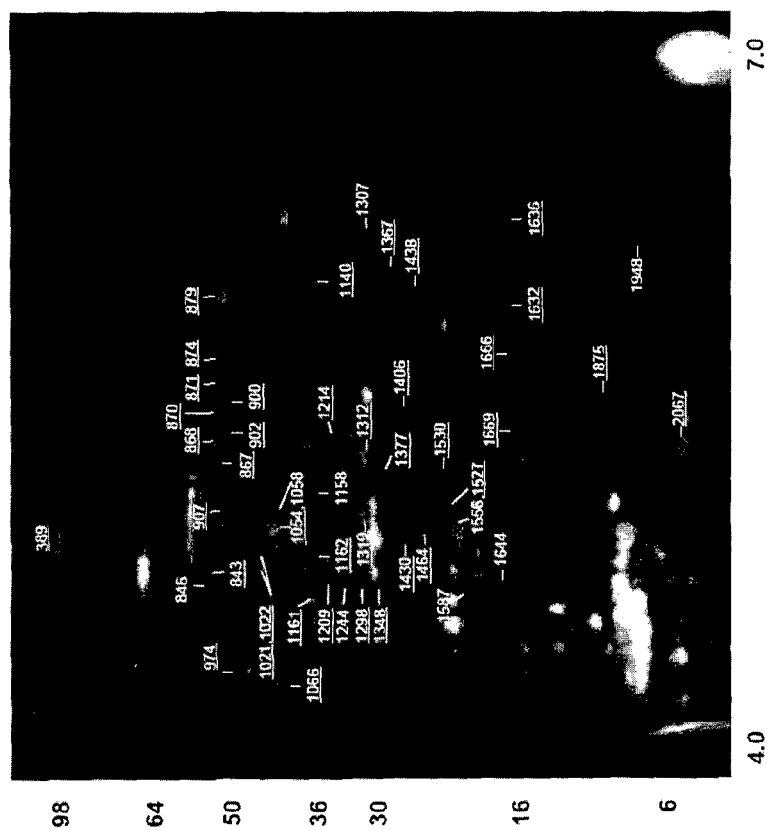

FIG. 15. 2D DIGE image of culture filtrate proteins from log phase and starvation conditions. The numbered protein spots were excised from 2D DIGE gels post-stained with silver and subjected to MS identification. Spots #1666 and 1669 were identified by PMF and MS/MS, respectively, as Rv1284.

EXAMPLES

Example 1

Single Protein and Protection in a Preventive TB Vaccination Model

Groups of CB6F1 mice were either vaccinated three times with 5 ug of one of the recombinant proteins formulated in the liposome based adjuvant CAF01, injected 3 times with an equal volume of saltwater (200 uL) or vaccinated once with BCG. Spacing between vaccination were 2 weeks and six weeks after third vaccination all animals were aerosolly challenge with virulent *M. tuberculosis* Erdman. Six weeks after challenge all mice were euthanized and the number of bacteria in lungs of individual animals was determined by plating dilutions of lung homogenate and counting the number of colonies (FIG. 1). Vaccination with the individual ESX-1 related proteins—Rv3615c, Rv3614c and Rv3849— induced comparable and significant protection against tuberculosis thus not at the level of BCG.

Example 2

The H64 Fusion Protein—Immune Responses and Protection in a Preventive TB Vaccination Model Groups of CB6F1 mice were either vaccinated three times with 5 ug of one of the fusion proteins H56 or H64 formulated in the liposome based adjuvant CAF01, injected 3 times with an equal volume of saltwater (200 uL) or vaccinated once with BCG. Spacing between vaccination were 2 weeks and. Three weeks after $3^{rd}$ vaccination animals were bleed, PBMC's isolated and the vaccine induced T cell responses were measured. 5×106 PMBC's were incubated with 2 ug of the individual proteins present in the two fusion proteins for three days and secreted IFN-g was measured in the media by ELISA (FIG. 2A). In the H56 vaccinated animals there is strong recognition of Ag85B and ESAT-6 and a weak recognition of the third protein, Rv2660c. H64 vaccinated animals have a strong response specific for ESAT-6 and Rv3614 and a moderate response towards PE35 (Rv3872) and Rv3849. In this inbred mice strain there is no response towards Rv3865 and Rv3615c. There is no response in the saline injected animals confirming the responses are vaccine specific.

Six weeks after third vaccination all animals were aerosolly challenge with virulent *M. tuberculosis* *H*37Rv (FIG. 2B) or *M. tuberculosis* Erdman (FIG. 2C). Six weeks after challenge all mice were euthanized and the number of bacteria in lungs of individual animals was determined by plating dilutions of lung homogenate and counting the number of colonies (FIGS. 2B and 2C).

In both experiments vaccination with either H64 or H56 induced significant protection compared to the saline control group. Furthermore, statistical comparison of the CFU's in H56 and H64 vaccinated animals revealed that H64 reduced the bacteria numbers significantly more than H56 did after H37Rv challenge (FIG. 2B).

Example 3

Rv3614c and Rv3615c Immune Responses after Vaccination in a Post-Exposure TB Vaccination Model In the post-exposure TB vaccination model mice are initially challenged with *M. tb.* via the aerosol route. To mimic the latent stage of infection mice are given antibiotics ad libitum in the drinking water from 6 to 12 weeks post-infection (p.i.). Groups of mice were vaccinated at week 10. 13 and 16 p.i. with either 5 µg of the recombinant proteins formulated in the liposome based adjuvant CAF01 or an equal volume of saltwater (200 µl). 1 week after the final vaccination (week 17 p.i.) vaccine-induced immune responses was assessed in the lung and determined by intracellular staining for cytokines following 6 hours of restimulation of lung lymphocytes with the vaccine-antigen or TB10.4 (FIG. 3). Vaccination with Rv3614c or Rv3615c induced a significant vaccine-specific immune response not measurable at comparable levels in the lungs of control mice.

Example 4

The H64 Fusion Protein—Immune Responses and Protection in a Post-Exposure TB Vaccination Model The post-exposure TB vaccination model was generated as described in example 3 and was used to evaluate the effect of post-exposure immunization with H64 fusion-protein. Groups of mice were either vaccinated three times with 5 ug H64 formulated in the liposome based adjuvant CAF01, injected 3 times with an equal volume of saltwater (200 uL) or vaccinated once with BCG. H64 immunogenicity was evaluated in both CB6F1 (C57BL/6×BALB/c) (FIG. A-C) and FvB mice (FIG. 4D). Following the three immunizations, lymphocytes were obtained from the lungs of the mice, and stimulated in vitro with the individual components and/or the fusion protein. At week 17 p.i. where vaccine-induced response was measured the infection-driven response was negligible as measured in the saline-injected control group (FIG. 4B). This is in contrast to the IFN-γ responses measured in the vaccinated group (FIGS. 4A and D). As expected the pattern of recognition did differ between the two distinct mouse strains FvB (FIG. 4A) and CB6F1 (FIG. 4D). H64 vaccination of FvB mice primarily led to an induction of a IFN-γ response directed towards Rv3615c whereas a response was induced to ESAT6, Rv3614c, Rv3849 and to a lesser extent Rv3872 in the CB6F1 mice. Thus, H64 is a highly immunogenic vaccine resulting in substantial amounts of IFN-γ production. At 37 weeks p.i. all mice were euthanized and the number of bacteria in the lungs of indivudal mice were determined by serial plating dilutings of lung homogenate and counting the number of colonies after 2-3 weeks of incubation at 37° C. At this timepoint the control animals had a mean bacterial load of 4.021 log 10 CFU comparable to the mean bacterial load following BCG vaccination (3.807 log 10 CFU), whereas the bacterial load of the H64 vaccinated was slightly lower (2.917 log 10 CFU) (FIG. 4C).

Example 5

Single Protein Protection of Seven ESX-1 Antigens Against Aerosol TB Challenge in Two Preventive TB Vaccination Models Groups of CB6F1 or B6C3F1 mice were either vaccinated three times with 5 ug of one of the recombinant proteins formulated in the liposome based adjuvant CAF01, injected 3 times with an equal volume of saltwater (200 uL) or vaccinated once with BCG. Spacing between vaccination were 2 weeks and six weeks after third vaccination all animals were aerosolly challenge with virulent *M. tuberculosis* Erdman. Six weeks after challenge all mice were euthanized and the number of bacteria in lungs of individual animals was determined by plating dilutions of lung homogenate and counting the number of colonies (FIG. 5A-C).

In the B6C3F1 strain (FIGS. 5A and B) vaccination with seven individual ESX-1 related proteins—Rv3616c, Rv3615c, Rv3614c Rv3865, ESAT-6, Rv3849, og Rv3872—induced variable degrees of protection ranging from 0.30 to 1.31 $\log_{10}$ reduction of the bacteria load in the lung of individual animals relative to the saline control group. None of the single proteins reached the 1.53 $\log_{10}$ reduction obtained after *M. bovis* BCG vaccination. In the CB6F1 mouse strain (FIG. 5C) vaccination with four of the seven proteins, Rv3615c, Rv3614c, ESAT-6 and Rv3849, induced a protective immune response resulting in a CFU reduction between 0.24 and 0.52 $\log_{10}$

Example 6

The Optimal Prophylactic Vaccination Dose of H64 for the CB6F1 Mice Strain is 5 ug of Protein in CAF01

Groups of CB6F1 or mice were either vaccinated three times with various doses of the recombinant H64 fusion protein formulated in the liposome based adjuvant CAF01, injected 3 times with an equal volume of saltwater (200 uL) or vaccinated once with BCG. Spacing between vaccination were 2 weeks and six weeks after third vaccination all animals were aerosolly challenge with virulent *M. tuberculosis* Erdman. Three weeks after immunization the potential vaccine specific T cell present in spleen (FIG. 6A) and blood (FIG. 6B) was measured by in vitro stimulation of isolated PBMC's and splenocytes. The general tendency being that the higher the vaccine dose the stronger T cell responses. Six weeks after challenge all mice were euthanized and the number of bacteria in lungs of individual animals was determined by plating dilutions of lung homogenate and counting the number of colonies (FIG. 6C). Immunization with 5 ug H64 resulted in the lowest number of bacteria and though the best protection.

Example 7

Single Protein and Protection in a Preventive TB Vaccination Model

Groups of CB6F1 mice were either vaccinated three times with 5 ug of one of the recombinant proteins formulated in the liposome based adjuvant CAF01, injected 3 times with an equal volume of saltwater (200 uL) or vaccinated once with BCG. Spacing between vaccination were 2 weeks and six weeks after third vaccination all animals were aerosolly challenge with virulent *M. tuberculosis* Erdman. Six weeks after challenge all mice were euthanized and the number of bacteria in lungs of individual animals was determined by plating dilutions of lung homogenate and counting the number of colonies (FIG. 7). Vaccination with the individual ESX-2 and ESX-5 secreted proteins—Rv3891, Rv3619 and Rv3620—induced comparable and significant protection against tuberculosis though not at the level of BCG.

Example 8

CFP10-ESAT6 Family Fusions—Immune Responses and Protection in a Preventive TB Vaccination Model Twelve of the paralogous ESAT-6 family proteins were fused as six protein dimers: CFP10-ESAT6, Rv3891c-3890c, Rv0287-0288, Rv3445c-3444c, Rv3620c-3619c and Rv3905c-3904c (FIG. 8A). In all construcs the two proteins were separated by a nine amino acid long spacer sequence (GLVPRGSTG). Groups of CB6F1 or B6C3F1 mice were either vaccinated three times with 5 ug of each of the recombinant dimer proteins formulated in the liposome based adjuvant CAF01, injected 3 times with an equal volume of saltwater (200 uL) or vaccinated once with BCG. Spacing between vaccination were 2 weeks and six weeks after third vaccination all animals were aerosolly challenged with virulent *M. tuberculosis* Erdman. Six weeks after challenge all mice were euthanized and the number of bacteria in lungs of individual animals was determined by plating dilutions of lung homogenate and counting the number of colonies (FIGS. 8B and C). In CB6F1 mice, vaccination with CFP10-ESAT6, Rv3891c-3891c or Rv0287-0288 resulted in a $\log_{10}$ reduction of the bacterial number in the lung between 0.25-0.45 (FIG. 8B). The same three dimer fusion plus Rv3620c-3619c protected B6C3F1 mice (FIG. 8C). In none of the two strains was the protective efficacy of the tested dimer fusions on level with the live vaccine BCG that induced a log 10 reduction of 1.4 and 0.85.

In B6C3F1 mice vaccine specific responses was found in blood 3 weeks post third vaccination in the CFP10-ESAT6, Rv0287-0288, Rv3445c-3444c, Rv3620c-3619c and Rv3905c-3904c vaccinated groups (FIG. 8D).

Example 9

The H65 Fusion Protein—Immune Responses and Protection in a Preventive TB Vaccination Model Groups of B6C3F1 mice were vaccinated three times with 5 ug of H65 (FIG. 9A) formulated in CAF01 adjuvant or once with the live vaccine M. bovis BCG. To confirm vaccine induced responses against each of the three ESX secreted dimers, splenocytes were isolated 3 weeks post third vaccination. $5 \times 10^6$ spenocytes were stimulated for 6 hours with 2 ug of either Rv3891c-Rv3890c, Rv0287-Rv0288 or Rv3620c-Rv3619c dimer fusion-protein. The CD4 T cell expression of IL-2, TNF-α and IFN-γ cytokines in response to antigen stimulation was measured by polychromatic flow cytometry (FIG. 9B). The ranking of response was Rv3891c-Rv3890c>Rv0287-Rv0288>Rv3620c-Rv3619c however for all three dimer proteins we observed vaccine specific polyfunctional T cells including IL-2$^+$, TNF-α$^+$, IFN-γ$^+$ and IL-2$^+$, TNF-α$^+$ CD4 T cells. Six weeks after third vaccination all animals were aerosolly challenged with virulent M. tuberculosis Erdman and euthanized six weeks later. The number of bacteria in lungs of individual animals was determined by plating dilutions of lung homogenate and counting the number of colonies (FIG. 9C). H65 and BCG both induced significant protection ($\log_{10}$ reduction ~0.7).

Groups of CB6F1 mice were vaccinated three times with 5 ug of H65 (FIG. 9A) or H56 (fusion of Ag85B-ESAT6 and Rv2660c) formulated in CAF01 adjuvant or once with the live vaccine M. bovis BCG. To establish which of the 6 antigens in H65 that are immunogenic in the CB6F1 inbred mice strain, spleniocytes were isolated 3 weeks post third vaccination. $5 \times 10^6$ spenocytes were stimulated for 72 hours with 2 ug of either Rv3891c, Rv3890c, Rv0287, Rv0288, Rv3620c or Rv3619c single protein (FIG. 10A). Significant amounts of IFN-γ was released to the medium from cells isolated from H65 vaccinated animals and stimulated with Rv0287, Rv0288, Rv3620c or Rv3619c, whereas there was no response towards Rv3891c or Rv3890c (FIG. 10A). In saline injected animals there was no response to any of the 6 antigens after stimulation (FIG. 10B).

Six weeks after third vaccination all animals were aerosolly challenged with virulent M. tuberculosis Erdman and euthanized six or twenty-four weeks later. The number of bacteria in lungs of individual animals was determined by plating dilutions of lung homogenate and counting the number of colonies (FIGS. 10C and D). At week six after challenge (FIG. 9C) H65 and H56 both resulted in similar and significant protection ($\log_{10}$ reduction ~0.8). At week 24 post challenge (FIG. 10D) vaccination with H65 or H56 still induced a comparable reduction of bacteria number in the lung but compared to the control group (CAF01) the difference was no longer statistical significant ($\log_{10}$ reduction=0.37 for H65 and 0.34 for H56).

Example 10

The H65 Fusion Protein—Immune Responses After Post-Exposure Vaccination in Two Mice Strains In the post-exposure TB vaccination model mice are initially challenged with M. tb. via the aerosol route. To mimic the latent stage of infection mice are given antibiotics ad libitum in the drinking water from 6 to 12 weeks post-infection (p.i.). Groups of FvB or CB6F1 mice were either vaccinated three times with 5 ug H65 formulated in the liposome based adjuvant CAF01 or injected 3 times with an equal volume of saltwater (200 uL).

Infection-driven immune responses specific for the components of H65 (Rv3891c, Rv3890c, Rv0287, Rv0288, Rv3620c, Rv3619c) at week 17 p.i. were measured in the lung of infected FvB mice and the responses were barely detectable (FIG. 11B). Following vaccination, we measured a pronounced response in the lungs directed towards Rv3619c in the FvB mouse strain (FIG. 11A). In the CB6F1 mouse strain there was in addition a response raised towards Rv0287 and Rv0288 (FIG. 11C). Hence, the H65 fusion-protein is highly immunogenic resulting in a robust induction of vaccine-specific IFN-γ release. After 37 weeks infection the number of bacteria was enumerated in individual mice (FIG. 10D). Comparison between H65 vaccinated and the negative control group shows a reduction of CFU's in H65 vaccinated animals. The protection level was comparable to the positive control (H56) and more pronounced than for the BCG vaccine.

Example 11

The Abundance of the Rv1284 Protein is Increased Under Nutrient Starvation

Rv1284 has previously been identified by proteomics in M. tuberculosis lysates[37]. To investigate the abundance of the protein under nutrient starvation, two-dimensional difference gel electrophoresis (2D DIGE) was applied to investigate the culture filtrate (CF) and lysate proteome of M. tuberculosis H37Rv bacteria in normal log phase growth and after six weeks of nutrient starvation.

Erlenmeyer flasks containing 200 ml of modified Sauton medium were inoculated with $2 \times 10^6$ bacteria per ml and placed in a standard shaking incubator at 37° C. After 7 days of growth to log phase, cultures were pelleted, washed twice with PBS, and resuspended in 200 ml PBS followed by incubation for six weeks without shaking. Control log phase cultures were obtained after 7 days of culturing in 200 ml modified Sauton medium in 500 ml flasks at 37° C. under shaking conditions. After harvesting of cultures, the bacterial pellet was washed twice in PBS, resuspended in 10 mM Tris, 250 mM sucrose buffer, pH 7.0, and broken with glass beads using a Mini-Beadbeater. The lysates were sterile filtered and protein concentration determined by the 2-D Quant kit (GE Healthcare). In addition, the culture medium was collected, sterile filtered and concentrated approx. 160 times in Centriprep-3 ultrafiltration units.

Lysate and CF samples were analysed in two separate experiments. Each 2D DIGE experiment included triplicate log phase and starvation samples. 50 µg of each sample was prepared for 2D DIGE by the 2D Clean-up kit (GE Healthcare) and resolubilized in 30 mM Tris, 7 M Urea, 2 M Thio-Urea, 4% CHAPS, pH 8.5. Cy2, Cy3 and Cy5 minimal labeling was performed with 125 pmol of each CyDye, followed by isoelectric focusing with pH 4-7 IPG strips. Cy2, Cy3 and Cy5 labeled samples were applied during the rehydration step in 8 M urea, 2% CHAPS, 0.5% IPG buffer, 18 mM DTT. The second dimension separation was performed in 10 to 20% Tris-glycine SDS-PAGE gradient gels. After electrophoresis, the gels were scanned by a Typhoon 9410 gel imager, and spot images were analyzed with the Image Master Platinum 2.0 software. Spots which displayed more than 1.5 fold difference in volume ratio, p<0.05 (student's t-test), were selected for identification. The 2D DIGE gels were silver stained and spots were excised for MALDI-TOF MS or MALDI-TOF MS/MS analysis. Two spots (#1666 and #1669 on FIG. 12) displayed increased abundance in CF from six week nutrient starved cultures compared to log phase cultures. These spots were identified by MALDI-TOF MS and MALDI-TOF MS/MS as Rv1284. In parallel, these spots were also selected as increased in lysates from nutrient starved cultures, and confirmed as Rv1284 by MS.

Example 12

Rv1284 Immune Responses and Protection in a Preventive TB Vaccination Model

Groups of CB6F1 and B5C3F1 mice were vaccinated three times with 5 ug of Rv1284 formulated in CAF01 adjuvant or once with the live vaccine *M. bovis* BCG. To measure vaccine induced responses blood was drawn from individual animals and PBMC's isolated 2 weeks after third vaccination. $5 \times 10^6$ PBMC's were stimulated for 72 hours with 2 ug of vaccine antigen (Rv1284) or a control antigen (Rv0287) and released IFN-γ was measured in the cell medium by ELISA (FIGS. 13A and B). In both mice strain vaccination with Rv1284 induced a significant antigen specific immune response.

Six weeks after third vaccination all animals were aerosolly challenge with virulent *M. tuberculosis* Erdman and euthanized six weeks later. The number of bacteria in lungs of individual animals was determined by plating dilutions of lung homogenate and counting the number of colonies (FIGS. 13C and D). Rv1284 vaccination reduced the number of bacteria significantly in both strains compared to the saline control group ($\log_{10}$ reduction=0.43 in CB6F1 and 0.54 in B6C3F1).

Example 13

The Protective Efficacy of H1+Rv1284 in a Preventive TB Vaccination Model

Groups of FVB (H2^q) mice were vaccinated three times with 5 ug of H1 fusion protein or H1+Rv1284 formulated in CAF01 adjuvant. The control group received three saline injections. Six weeks after third vaccination/injection all animals were aerosolly challenge with virulent *M. tuberculosis* Erdman and euthanized six weeks later. The number of bacteria in lungs of individual animals was determined by plating dilutions of lung homogenate and counting the number of colonies (FIG. 14). Vaccination of FVB mice with the H1 fusion protein only reduced the number of bacteria in half ($\log_{10}$ reduction=0.32) whereas the mixture of H1+Rv1284 reduced the bacteria number 6.6 times ($\log_{10}$ reduction=0.82). Statistically the H1+Rv1284 vaccinated animals had significantly lower bacteria load than both the saline injected and H1 vaccinated group.

Example 14

Immune Response of Ag85B, ESAT-6 and Rv1284 After Post Exposure Vaccination with Single Proteins Mice were infected, treated with antibiotics and vaccinated according to the protocol described in example 3. Here, groups of mice were vaccinated three times with either Ag85B. ESAT6 or Rv1284, all formulated in the liposome based adjuvant CAF01. The control mice were vaccinated in a similar way with saltwater. One week following the final vaccination lymphocytes were obtained from the lungs and used for 6 hour in vitro culture with the respective vaccine antigen i.e. Ag85B, ESAT6 or Rv1284 and TB10.4 as a measurement for infection-driven responses. Vaccine- or infection-driven responses were measured by staining for intracellular cytokines and cumulative frequency of CD4 T cell responders, expression either IFN-γ, IL-2, TNF-α or any combination of the three, were determined. Vaccination with Ag85B, ESAT-6 or Rv1284 all induced significant vaccine-specific CD4 T cell responses (FIG. 15) that could not be measured at comparable levels in the control animals. The TB10.4 infection-driven CD4 T cell response in comparison was low but this is expected given that at this particular timepoint the bacterial load is still relatively low.

REFERENCES

1. Cole, S. T., et al. Deciphering the biology of *Mycobacterium tuberculosis* from the complete genome sequence. *Nature* 393, 537-544 (1998).
2. Bold, T. D., Banaei, N., Wolf, A. J. & Ernst, J. D. Suboptimal activation of antigen-specific CD4+ effector cells enables persistence of *M. tuberculosis* in vivo. *PLoS Pathog* 7, e1002063 (2011).
3. Egen, J. G., et al. Intravital imaging reveals limited antigen presentation and T cell effector function in mycobacterial granulomas. *Immunity* 34, 807-819 (2011).
4. Pym, A. S., et al. Recombinant BCG exporting ESAT-6 confers enhanced protection against tuberculosis. *Nat Med* 9, 533-539 (2003).
5. Stanley, S. A., Raghavan, S., Hwang, W. W. & Cox, J. S. Acute infection and macrophage subversion by *Mycobacterium tuberculosis* require a specialized secretion system. *Proc Natl Acad Sci USA* 100, 13001-13006 (2003).
6. Abdallah, A. M., et al. Type VII secretion—mycobacteria show the way. *Nat Rev Microbiol* 5, 883-891 (2007).
7. Fortune, S. M., et al. Mutually dependent secretion of proteins required for mycobacterial virulence. *Proc Natl Acad Sci USA* 102, 10676-10681 (2005).
8. Gordon, S. V., et al. Identification of variable regions in the genomes of tubercle bacilli using bacterial artificial chromosome arrays. *Mol Microbiol* 32, 643-655 (1999).
9. Gao, L. Y., et al. A mycobacterial virulence gene cluster extending RD1 is required for cytolysis, bacterial spreading and ESAT-6 secretion. *Mol Microbiol* 53, 1677-1693 (2004).
10. MacGurn, J. A. & Cox, J. S. A genetic screen for *Mycobacterium tuberculosis* mutants defective for phagosome maturation arrest identifies components of the ESX-1 secretion system. *Infect Immun* 75, 2668-2678 (2007).
11. MacGurn, J. A., Raghavan, S., Stanley, S. A. & Cox, J. S. A non-RD1 gene cluster is required for Snm secretion in *Mycobacterium tuberculosis*. *Mol Microbiol* 57, 1653-1663 (2005).
12. Bahk, Y. Y., et al. Antigens secreted from *Mycobacterium tuberculosis*: identification by proteomics approach and test for diagnostic marker. *Proteomics* 4, 3299-3307 (2004).

13. Das, C., Ghosh, T. S. & Mande, S. S. Computational analysis of the ESX-1 region of *Mycobacterium tuberculosis*: insights into the mechanism of type VII secretion system. *PLoS ONE* 6, e27980 (2011).
14. Champion, P. A., Stanley, S. A., Champion, M. M., Brown, E. J. & Cox, J. S. C-terminal signal sequence promotes virulence factor secretion in *Mycobacterium tuberculosis*. *Science* 313, 1632-1636 (2006).
15. Raghavan, S., Manzanillo, P., Chan, K., Dovey, C. & Cox, J. S. Secreted transcription factor controls *Mycobacterium tuberculosis* virulence. *Nature* 454, 717-721 (2008).
16. Chen, J. M., et al. EspD is critical for the virulence-mediating ESX-1 secretion system in *Mycobacterium tuberculosis*. *J Bacteriol* 194, 884-893 (2012).
17. Brodin, P., et al. Dissection of ESAT-6 system 1 of *Mycobacterium tuberculosis* and impact on immunogenicity and virulence. *Infect Immun* 74, 88-98 (2006).
18. Ohol, Y. M., et al. *Mycobacterium tuberculosis* MycP1 protease plays a dual role in regulation of ESX-1 secretion and virulence. *Cell Host Microbe* 7, 210-220 (2010).

The invention claimed is:

1. A fusion protein which comprises the amino acid sequences selected from:
   (a) SEQ ID NO:1 (ESAT6), SEQ ID NO: 2 (Rv3614c), SEQ ID NO: 3 (Rv3615c), SEQ ID NO: 4 (Rv3865), SEQ ID NO: 5 (Rv3849) and SEQ ID NO: 6 (Rv3872);
   (b) SEQ ID NO: 2 (Rv3614c), SEQ ID NO: 3 (Rv3615c), SEQ ID NO: 4 (Rv3865), SEQ ID NO: 5 (Rv3849) and SEQ ID NO: 6 (Rv3872);
   (c) SEQ ID NO: 2 (Rv3614c), SEQ ID NO: 3 (Rv3615c), SEQ ID NO: 4 (Rv3865), SEQ ID NO: 5 (Rv3849), SEQ ID NO: 6 (Rv3872) and SEQ ID NO: 7 (Rv3616c);
   (d) SEQ ID NO: 2 (Rv3614c), SEQ ID NO: 3 (Rv3615c), SEQ ID NO: 4 (Rv3865), SEQ ID NO: 5 (Rv3849), SEQ ID NO: 6 (Rv3872), SEQ ID NO: 7 (Rv3616c) and SEQ ID NO: 8 (Rv3881c);
   (e) SEQ ID NO: 2 (Rv3614c), SEQ ID NO: 3 (Rv3615c), SEQ ID NO: 4 (Rv3865), SEQ ID NO: 5 (Rv3849), SEQ ID NO: 6 (Rv3872) and SEQ ID NO: 8 (Rv3881c); and
   (f) an amino acid sequence having at least 95% sequence identity to any one of (a)-(e) over the full sequences recited in any one of (a)-(e) and at the same time being immunogenic.

2. The fusion protein according to claim 1 wherein all cysteines in said fusion protein have been replaced by another amino acid to avoid sulphur-bridge formation and protein aggregation.

3. The fusion protein according to claim 2, wherein the cysteines have been replaced with serine.

4. The fusion protein according to claim 1, wherein the amino acid sequences of the fusion protein are linked with a linker molecule.

5. The fusion protein according to claim 4 with the amino acid sequence selected from SEQ ID NO: 18 (H64), SEQ ID NO: 19 (H68), SEQ ID NO: 20 (H69), SEQ ID NO: 21 (H70), and SEQ ID NO: 22 (H71).

6. A vaccine comprising a fusion protein according to claim 1 and a pharmaceutically acceptable carrier.

7. The vaccine according to claim 6 additionally comprising an adjuvant.

8. The vaccine according to claim 7 wherein the adjuvant is selected from the group consisting of cationic liposomes, Quil A, poly I:C, aluminium hydroxide, Freund's incomplete adjuvant, IFN-γ, IL-2, IL-12, monophosphoryl lipid A (MPL), Trehalose Dimycolate (TDM), Trehalose Dibehenate (TDB), Muramyl Dipeptide (MDP), and monomycolyl glycerol (MMG), or combinations hereof.

9. The vaccine according to claim 8, wherein said cationic liposomes are dimethyldioctadecylammonium bromide (DDA).

10. A fusion protein comprising the amino acid sequences SEQ ID NO:1 (ESAT6), SEQ ID NO: 2 (Rv3614c), SEQ ID NO: 3 (Rv3615c), SEQ ID NO: 4 (Rv3865), SEQ ID NO: 5 (Rv3849) and SEQ ID NO: 6 (Rv3872);
   or an amino acid sequence having at least 95% identity over the full sequences of SEQ ID NO:1 (ESAT6), SEQ ID NO: 2 (Rv3614c), SEQ ID NO: 3 (Rv3615c), SEQ ID NO: 4 (Rv3865), SEQ ID NO: 5 (Rv3849) and SEQ ID NO: 6 (Rv3872) and at the same time being immunogenic.

11. The fusion protein according to claim 10, comprising the amino acid sequences SEQ ID NO:1 (ESAT6), SEQ ID NO: 2 (Rv3614c), SEQ ID NO: 3 (Rv3615c), SEQ ID NO: 4 (Rv3865), SEQ ID NO: 5 (Rv3849) and SEQ ID NO: 6 (Rv3872).

12. The fusion protein according to claim 10 wherein all cysteines in said fusion protein have been replaced by another amino acid to avoid sulphur-bridge formation and protein aggregation.

13. The fusion protein according to claim 12, wherein the cysteines have been replaced with serine.

14. The fusion protein according to claim 10, wherein the amino acid sequences of the fusion protein are linked with a linker molecule.

15. A vaccine comprising a fusion protein according to claim 10 and a pharmaceutically acceptable carrier.

16. The vaccine according to claim 15 additionally comprising an adjuvant.

17. The vaccine according to claim 16 wherein the adjuvant is selected from the group consisting of cationic liposomes, Quil A, poly I:C, aluminium hydroxide, Freund's incomplete adjuvant, IFN-γ, IL-2, IL-12, monophosphoryl lipid A (MPL), Trehalose Dimycolate (TDM), Trehalose Dibehenate (TDB), Muramyl Dipeptide (MDP), and monomycolyl glycerol (MMG), or combinations hereof.

* * * * *

UNITED STATES PATENT AND TRADEMARK OFFICE
CERTIFICATE OF CORRECTION

PATENT NO. : 9,526,773 B2  
APPLICATION NO. : 14/437998  
DATED : December 27, 2016  
INVENTOR(S) : Claus Aagaard et al.

Page 1 of 1

It is certified that error appears in the above-identified patent and that said Letters Patent is hereby corrected as shown below:

In the Claims

Claim 6, first Line (Column 93, Line 48), replace "A vaccine" with --An immunogenic composition--.

Claim 7, first Line (Column 93, Line 50), replace "vaccine" with --immunogenic composition--.

Claim 8, first Line (Column 93, Line 52), replace "vaccine" with --immunogenic composition--.

Claim 9, first Line (Column 94, Line 15), replace "vaccine" with --immunogenic composition--.

Claim 15, first Line (Column 94, Line 42), replace "A vaccine" with --An immunogenic composition--.

Claim 16, first Line (Column 94, Line 44), replace "vaccine" with --immunogenic composition--.

Claim 17, first Line (Column 94, Line 46), replace "vaccine" with --immunogenic composition--.

Signed and Sealed this  
Twenty-first Day of March, 2017

Michelle K. Lee  
*Director of the United States Patent and Trademark Office*